United States Patent [19]

Theologis et al.

[11] Patent Number: 5,723,766
[45] Date of Patent: Mar. 3, 1998

[54] CONTROL OF FRUIT RIPENING THROUGH GENETIC CONTROL OF ACC SYNTHASE SYNTHESIS

[75] Inventors: Athanasios Theologis, Los Altos Hills, Calif.; Takahido Sato, Tokyo, Japan

[73] Assignee: The United States of America as represented by the Secretary of the Agriculture, Washington, D.C.

[21] Appl. No.: 481,171

[22] Filed: Jun. 7, 1995

Related U.S. Application Data

[62] Division of Ser. No. 378,313, Jan. 25, 1995, which is a continuation of Ser. No. 862,493, Apr. 2, 1992, abandoned, which is a continuation-in-part of Ser. No. 579,896, Sep. 10, 1990, abandoned.

[51] Int. Cl.$^6$ ............... A01H 4/00; C12N 15/82; C12N 5/14
[52] U.S. Cl. ............ 800/205; 435/320.1; 435/240.4; 435/172.3; 800/DIG. 44
[58] Field of Search ............... 435/320.1, 240.4, 435/172.3; 800/205, DIG. 44; 536/23.2

[56] References Cited

U.S. PATENT DOCUMENTS 5,512,466  4/1996  Klee et al. ............... 435/172.3

OTHER PUBLICATIONS

Abeles, F.B., "Ethylene in Plant Biology" (1983) Academic Press, New York.
Nakajima, N., et al., *Plant Cell Physiol* (1986) 27:969–980.
Mehta, A.M., et al., *Proc Natl Acad Sci Use* (1988) 85:8810–8814.
Nakajima, N., et al., *Plant Cell Physiol* (1988) 29:989–990.
Tsai, D.S., et al., *Arch Biochem Biphys* (1988) 264:632–640.
Bleecker, A.B., et al., *Proc Natl Acad Sci USA* (1986) 83:7755–7759.
Privale, L.S., et al., *Arch Biochem Biophys* (1987) 253:333–340.
Sato, S., et al., *Plant Physiol* (1988) 88:109–114.
Van Der Straeten, D., et al., *Eur J Biochem* (1989) 182:639–647.
Theologis, A., et al., UCLA Symposia on Molecular and Cellular Biology, Mar. 27–Apr. 7, 1989, in: *J Cell Biochem* (1989) Supp. 13D, p. 241.
Sato, T., et al., *Proc Natl Acad Sci USA* (1989) 86:6621–6625.
UCLA Symposium on Molecular and Cellular Biology, Mar. 31–Apr. 22, 1990, in: *J Cell Biochem* (1990) Supp. 14E, p. 358.
*Horticultural Biotechnology* (1990) Wiley–Liss, Inc., pp. 247–246.
*Plant Gene Transfer* (1990) Alan R. Liss, Inc., pp. 289–299.
Plant Molecular Biology Meeting, Nato Advanced Study Institute, Bavaria, May 14–23, 1990.
Third International Symposium of the Society of Chinese Bioscientists in America, Jun. 24–30, 1990.
Sato, T. et al., *J Biol Chem* (1991) 266:3752–3759.
Van Der Straeten, D., et al., *Proc Natl Acad Sci (1990)* 87:4859–4863.

*Primary Examiner*—Che S. Chereskin
*Attorney, Agent, or Firm*—Morrison & Foerster LLP

[57] ABSTRACT

ACC synthases of higher plants are coded by multigene families; only certain members of these families are responsible for various plant development characteristics effected by ethylene. Control of the processes in plants which are mediated by ACC synthase can be effected by controlling expression of the relevant ACC synthase gene. In addition, comparison of the amino acid and nucleotide sequence of the ACC synthases from cucumber and tomato provides consensus sequences that permit the design of PCR primers that permit the isolation of ACC synthases from a variety of higher plants.

14 Claims, 39 Drawing Sheets

```
caactttcaaATGGGGTTTCATCAAATCGACGAAAGGAACCAAGCTCTTC
          M  G  F  H  Q  I  D  E  R  N  Q  A  L
                                  E  R  N  Q  A  L
TCTCGAAGATCGCCCTCGACGATGGCCATGGCGAGAACTCCCCGTATTTC  100
 L  S  K  I  A  L  D  D  G  H  G  E  N  S  P  Y  F
 L  S  K  I  A  L  D  D  G  H  G  E  N  S  P  Y  F ←—pACC7
GATGGGTGGAAAGCTTACGATAACGATCCGTTTCACCCTGAGAATAATCC
 D  G  W  K  A  Y  D  N  D  P  F  H  P  E  N  N  P
 D  G  W  K  A  Y  D  N  D  P  F  H  P  E  N  N  P
TTTGGGTGTTATTCAAATGGGTTTAGCAGAAAATCAGCTTTCCTTTGATA  200
    L  G  V  I  Q  M  G  L  A  E  N  Q  L  S  F  D
    L  G  V  I  Q  M  G  L  A  E  N  Q  L  S  F  D
TGATTGTTGACTGGATTAGAAAACACCCTGAAGCTTCGATTTGTACACCG
 M  I  V  D  W  I  R  K  H  P  E  A  S  I  C  T  P
 M  I  V  D  W  I  R  K  H  P  E  A  S  I  C
GAAGGACTTGAGAGATTCAAAAGCATTGCCAACTTCCAAGATTACCACGG  300
  E  L  E  R  F  K  S  I  A  N  F  Q  D  Y  H  G
CTTACAGAGTTTCGAAATGCAATTGCAAATTTTATGGGGAAAGTAAGAG
    L  P  E  F  R  N  A  I  A  N  F  M  G  K  V  R
GTGGGAGGGTAAAATTCGACCCGAGTCGGATTGTGATGGGTGGCGGTGCG  400
 G  G  R  V  K  F  D  P  S  R  I  V  M  G  G  G  A
ACCGGAGCGAGCGAAACCGTCATCTTTTGTTTGGCGGATCCGGGGGATGC
 T  G  A  S  T  V  I  F  C  L  A  D  P  G  D  A
TTTTTTGGTTCCTTCTCCATATTATGCAGGATTTGATCGAGACTTGAAAT  500
   F  L  V  P  S  P  Y  Y  A  G  F  D  R  D  L  K
GGCGAACACGAGCACAAATAATTCGGGTCCATTGCAACGGCTCGAATAAC
 W  R  T  R  A  Q  I  I  R  V  H  C (N) G  S  N  N
TTCCAAGTCACAAAGGCAGCCTTAGAAATAGCCTACAAAAAGGCTCAAGA  600
  F  Q  V  T  K  A  A  L  E  I  A  Y  K  K  A  Q  E
GGCCAACATGAAAGTGAAGGGTGTTATAATCACCAATCCCTCAAATCCCT
    A  N  M  K  V  K  G  V  I  I  T  N  P  S  N  P
TAGGCACAACGTACGACCGTGACACTCTTAAAACCCTCGTCACCTTTGTG  700
  L  G  T  T  Y  D  R  D  T  L  K  T  L  V  T  F  V
AATCAACACGACATTCACTTAATATGCGATGAAATATACTCTGCCACTGT
 N  Q  H  D  I  H  L  I  C  D  E  I  Y  S  A  T  V
CTTCAAAGCCCCAACCTTCACCAGCATCGCTGAGATTGTTGAACAAATGG  800
  F  K  A  P  T  F  T  S  I  A  E  I  V  E  Q  M
```

FIG. 1B(i)

```
AGCATTGCAAGAAGGAGCTCATCCATATTCTTTATAGCTTGTCCAAAGAC
 E  H  C  K  K  E  L  I  H  I  L  Y  S  L  S  K  D
ATGGGCCTCCCTGGTTTTCGAGTTGGAATTATTTATTCTTACAACGATGT   900
 M  G  L  P  G  F  R  V  G  I  I  Y  S  Y  N  D  V
CGTCGTCCGCCGTGCTCGGCAGATGTCGAGCTTCGGCCTCGTCTCGTCCC
 V  V  R  R  A  R  Q  M  S  S  F  G  L  V  S  S
AGACTCAACATTTGCTCGCCGCCATGCTTTCCGACGAGGACTTTGTCGAC   1000
 Q  T  Q  H  L  L  A  A  M  L  S  D  E  D  F  V  D
AAATTTCTTGCCGAGAACTCGAAGCGTGTGGGCGAGAGGCATGCAAGGTT
 K  F  L  A  E  N  S  K  R  V  G  E  R  H  A  R  F
CACAAAAGAATTGGATAAAATGGGGATCACTTGCTTGAACAGCAATGCTG   1100
 T  K  E  L  D  K  M  G  I  T  C  L  N  S  N  A
GAGTTTTTGTGTGGATGGATCTACGGAGGCTATTAAAAGACCAAACCTTC
 G  V  F  V  W  M  D  L  R  R  L  L  K  D  Q  T  F
AAAGCTGAAATGGAGCTTTGGCGTGTGATTATCAATGAAGTCAAGCTCAA   1200
 K  A  E  M  E  L  W  R  V  I  I  N  E  V  K  L  N
TGTTTCTCCTGGCTCATCCTTTCATGTCACTGAGCCAGGTTGGTTTCGAG
 V  S  P  G  S  S  F  H  V  T  E  P  G  W  F  R
TTTGTTTCGCAAACATGGACGACAACACCGTTGACGTTGCTCTCAATAGA   1300
 V  C  F  A  N  M  D  D  N  T  V  D  V  A  L  N  R
ATCCATAGCTTTGTCGAAAACATCGACAAGAAGGAAGACAATACCGTTGC
 I  H  S  F  V  E  N  I  D  K  K  E  D  N  T  V  A
AATGCCATCGAAAACGAGGCATCGAGATAATAAGTTACGATTGAGCTTCT   1400
 M  P  S  K  T  R  H  R  D  N  K  L  R  L  S  F
CCTTCTCAGGGAGAAGATACGACGAGGGCAACGTTCTTAACTCACCGCAC
 S  F  S  G  R  R  Y  D  E  G  N  V  L  N  S  P  H
ACGATGTCGCCTCACTCGCCGTTAGTAATAGCAAAAAATTAAttaaaaac   1500
 T  M  S  P  H  S  P  L  V  I  A  K  N
atttttcaaaatattcataccattcatatagtttttttttttttttttt
tgggtcaatgttgactaaagttacgtatattttttccacagtggatatga   1600
tgtaaacttcatatttttggtgggatggtgatagatgtaatgtatttgg
tttttcccttagggaactcatacttatttattaatgaaatgattgtgatt   1700
tat
```

FIG. 1B(ii)

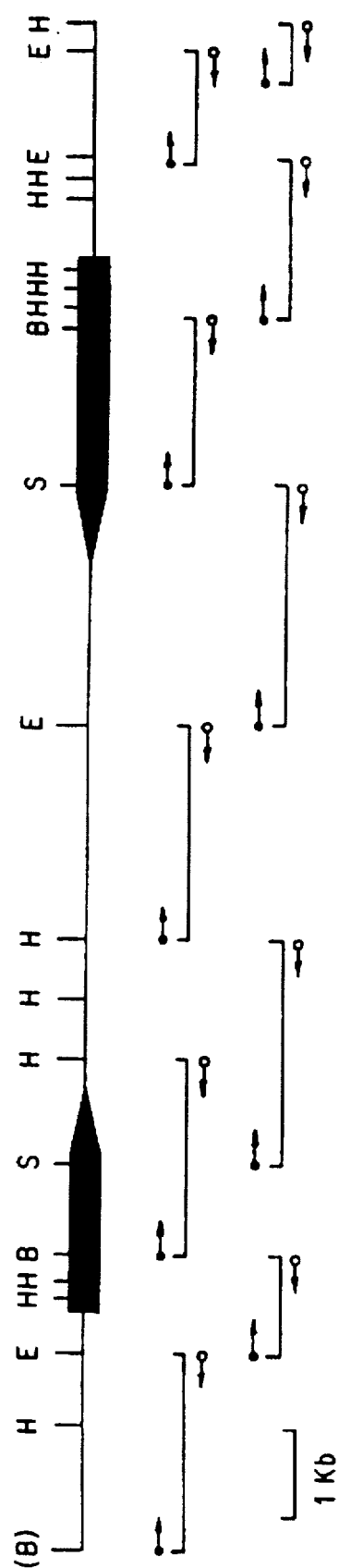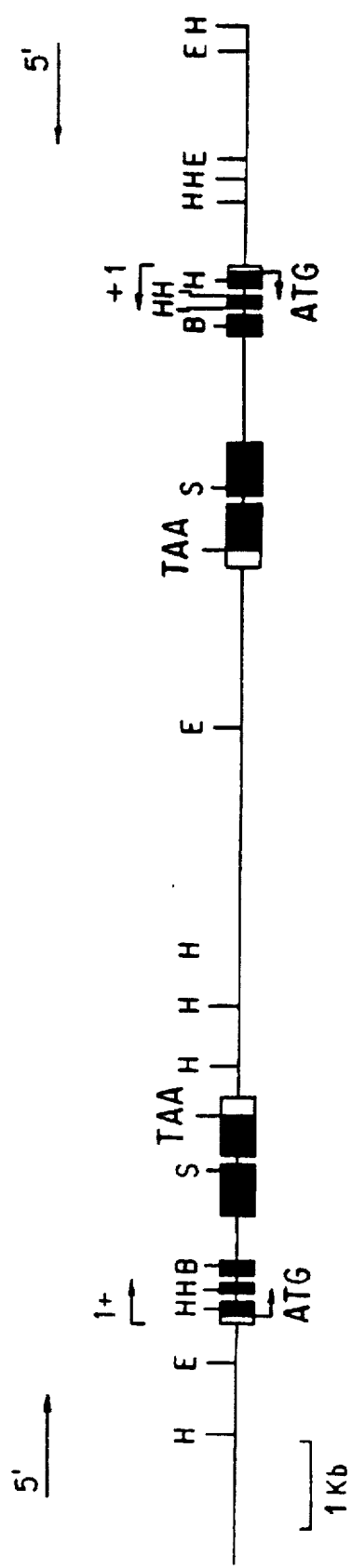

```
                10        20        30        40
                 .         .         .         .
                                                        ca
        cattggttggagagagagggaacgagtgcaacgaggatgctgggctctgaa
        aaggggtggattgtgagatcccacgaacgaaacattctttgtaagggtgt
        gaaaacctctccctagcatactcgttttaaaaacctcaaggagaagtaca      -2501
        aaaagaaaagccgaggaaggatttcaaaaagttagaacttcattaaaaat
        gaaagcacaaagaagagaattattagtaatgttcttgcacaagtataagt
        tgaaaaactaattctatcaagtgtgaatccacactcatctttcaaaatta
        agcaaacaaaacgagtcatgcttgccttctccaaattttatcactaatag
        tgtgacactcaatgtcccacttaccattcttggcccccacaaccacctcc
        aagaaacaataacttttactacccaaccccaattttggaacaaaaatga
        gtcaaatatatgaacaataacatcgtgtttcttcttaccgactcggttga
        atatgcaacgtttataatatacttcaagaaattttgagacattactcaaa
        taaagtctctcacaaaaatagaatatctttatactagtataatgaattgt
        ccacttcgatttaaatcctctaaagttcactttcgtaaatggcttaatga      -2001
        acagatttattaggatcaaattcaaaagttgaatgagactaaatagatat
        aataaaatctgattgttgcatgaagtatgcagctcaaagatgatgttttg
        cgaaaaaaatgcaaactaagcatgagtgcttctgtaaaaaaaaaatgaaa
        aagaaaaatatatatcgtactatcaaaaacattgtccttacttagacagc
        tcaaaacttttcatattcctatatttgtttatattgaaacttttccatt
        tcatttgtttaaatcatatttggttgtttaaataagaatactgtaacagt
        ccaagctcactgttagtagatattgtcttcttcggacttttccggcttct
        tctcaaggttttaaaatgtgtctactagggagagattttcacacacttat
        aaagaatgattcgttctcctcttcaactaatgtaaaatctcacaaatact
        aaacaattggaatttattaggatcagaatcaaaagttgagagatatagtg      -1501
        gaaacgaccgtcgagattaaatagatacaatcaagtttgatcattgtact
        aaataagtagctcggagatgtatacgagaaaagaaagcgcactataaaaa
        tgaggtaaaaagtggtcggagtagtatacaatgtgagaggtatgcaaata
        tacgtatttcctttaggtgaaaaagtccgaaaccacaccaaaaagcactc
        ttaaaaatgtgccaaaacggttctatcactcaatgtcaaatctttcaatt
        caaaagcatgtgggtattgattgctgcttccaacgaagcttcattctcct
        acttgttacacacacacaaactcgttgttcatgaccaattctatcccctt
        tcccatgtcatcctccaaacttttgacccttcaatttggtcccctaaccc
        ttttttcatcacatgggatgcaaccattttgatttagtctacgacattc
        ttttcatttatctacttacgccctccgagggaacagttggattgaaagtt      -1001
        cgacttcttagccttggagatgagagaaccggtacactccatgaattaca
        aaatttaaatctctaatcctaactttggagctacgtatgacctttgtatc
```

FIG. 3A

```
tttgtaagagcttttctcaatgctaacaaatattgtctatttcagctggt
tacgcattgtcgtctgcttcccgattttaaaatacgtctattaaggagag
gttttcacacccttactagaaacgtttcgttctccctctaaatgtgagat
ctcaccgtaactagctagagattaaaatgttattatagctagagattcaa
ccaaacataacacaaaaagataatcatagggatcaacaaaattcataact
agttcttataatatgcaataaaattcaaattaattatgcattagaagaaa
ataaaaaaacaattaagataacccaaaaattaatttccttctacctataa
atctataataagattcgagtattagattaaaattatcccaaatcaagaac    -501
ataaattaagatcataaacgtaatatattttaatcgagaacgtaaataca
ggacatacagattaagaattcaaatattttgaattataatatgaatttga
tagaaaataaaacaaaaactaaaaaataaacttagtaattatgatgagat
aaagaagattttgtgacatgatattttgttatgttccaaatctagagt
atgcctccacacatgcggggtcgggtcggctgtgtgtgtggctcgtctgc
ttgcttgaatcacaaccctccacgcatgcaattacgccctccttgactca
aaccccattttaactctctcttccattttattattttttctttaatttt
tttcatcactgtttttttttttttttttttcatggtttgaactttgaaa
agttgaattttctacacgtttgattttcctggtaagaacttgatcttgtt
ggatcttcctcactgcttataaattcactcaattctcttctttctttcct    -1
ATCTTACAACCCAAAACCTCTCATTTTTAGGCACATCTCAACAACTTTCA
AATGGGGTTTCATCAAATCGACGAAAGGAACCAAGCTCTTCTCTCGAAGA    100
  M  G  F  H  Q  I  D  E  R  N  Q  A  L  L  S  K
TCGCCCTCGACGATGGCCATGGCGAGAACTCCCCGTATTTCGATGGGTGG
  I  A  L  D  D  G  H  G  E  N  S  P  Y  F  D  G  W
AAAGCTTACGATAACGATCCGTTTCACCCTGAGAATAATCCTTTGGGTGT
  K  A  Y  D  N  D  P  F  H  P  E  N  N  P  L  G  V
TATTCAAATGGGTTTAGCAGAAAATCAGgtttggtatatcgtgttttcgt
  I  Q  M  G  L  A  E  N  Q
gttttcttatatgacttcacgtttgaaaatttcgctaactttgtttttt
tgtgaatttcgatagCTTTCCTTTGATATGATTGTTGACTGGATTAGAAA
               L  S  F  D  M  I  V  D  W  I  R  K
ACACCCTGAAGCTTCGATTTGTACACCGGAAGGACTTGAGAGATTCAAAA
  N  P  E  A  S  I  C  T  P  E  G  L  E  R  F  K
GCATTGCCAACTTCCAAGATTACCACGGCTTACCAGAGTTTCGAAATgta
  S  I  A  N  F  Q  D  Y  H  G  L  P  E  F  R  N
```

FIG. 3B

```
cgagatatgatatactcttaactatatctgaactcaaaaggttaagttga                                500
tgggttatgataaaatttctttcttgtcagGCAATTGCAAATTTTATGGG
                                A  I  A  M  F  M  G
GAAAGTAAGAGGTGGGAGGGTAAAATTCGACCCGAGTCGGATTGTGATGG
 K  V  R  G  G  R  V  K  F  D  P  S  R  I  V  M
GTGGCGGTGCGACCGGAGCGAGCGAAACCGTCATCTTTTGTTTGGCGGAT
 G  G  A  T  G  A  S  E  T  V  I  F  C  L  A  D
CCGGGGGATGCTTTTTTGGTTCCTTCTCCATATTATGCAGGgtgagttct
 P  G  D  A  F  L  V  P  S  P  Y  Y  A  G
tctttcatttccttttgttcacttttctttaagtcaatattccttagtcc
aacctggaaagagaaagaagagagagaaagaaaccatttgacaaattaat
aactctacaaattctctttgaaagtttgatgttttttttaaggtcaaaac
ttcaaccattctcttgcaaagaaaaaaaaagtcataattataatgaaga
aaaactaggccatccaagtcaaccttttaaatgctaataaagtcaata
tgctttgtaggtttaaaaaacaataaattgcttaatcatttcttaaattt                              1000
taattaaacccttttgactttatcattacccatttacataaattaacaat
ttattgctctttttgtagtaaaattaataaaaaaaaagttaggtgtaaac
gtacagtattatgttattgtaaaaatactgagaagtgttagtatgttgtt
tttcagATTTGATCGAGACTTGAAATGGCGAACACGAGCACAAATAATTC
       F  D  R  D  L  K  W  R  T  R  A  Q  I  I
GGGTCCATTGCAACCGCTCGAATAACTTCCAAGTCACAAAGGCAGCCTTA
 R  V  H  C  N  R  S  N  N  F  Q  V  T  K  A  A  L
GAAATAGCCTACAAAAAGGCTCAAGAGGCCAACATGAAAGTGAAGGGTGT
 E  I  A  Y  K  K  A  Q  E  A  N  M  K  V  K  G  V
TATAATCACCAATCCCTCAAATCCCTTAGGCACAACGTACGACCGTGACA
 I  I  T  N  P  S  N  P  L  G  T  T  Y  D  R  D
CTCTTAAAACCCTCGTCACCTTTGTGAATCAACACGACATTCACTTAATA
 T  L  K  T  L  V  T  F  V  N  Q  H  D  I  H  L  I
TGCGATGAAATATACTCTGCCACTGTCTTCAAAGCCCCAACCTTCACCAG
 C  D  E  I  Y  S  A  T  V  F  K  A  P  T  F  T  S
CATCGCTGAGATTGTTGAACAAATGGAGCATTGCAAGAAGGAGCTCATCC                               1500
 I  A  E  I  V  E  Q  M  E  H  C  K  K  E  L  I
ATATTCTTTATAGCTTGTCCAAAGACATGGGCCTCCCTGGTTTTCGAGTT
 H  I  L  Y  S  L  S  K  D  M  G  L  P  G  F  R  V
GGAATTATTTATTCTTACAACGATGTCGTCGTCCGCCGTGCTCGGCAGAT
 G  I  I  Y  S  Y  N  D  V  V  V  R  R  A  R  Q  M
GTCGAGCTTCGGCCTCGTCTCGTCCCAGACTCAACATTTGCTCGCCGCCA
 S  S  F  G  L  V  S  S  Q  T  Q  N  L  L  A  A
```

FIG. 3C

```
TGCTTTCCGACGAGGACTTTGTCGACAAATTTCTTGCCGAGAACTCGAAG
 M  L  S  D  E  D  F  V  D  K  F  L  A  E  N  S  K
CGTGTGGGCGAGAGGCATGCAAGgtttgttaaactacaccattattattt
 R  V  G  E  R  H  A  R
gtgggattgaaaaagcattacttttttgcaattaatttaagaatgtattaat
caaattcagGTTCACAAAAGAATTGGATAAAATGGGGATCACTTGCTTGA
          F  T  K  E  L  D  K  M  G  I  T  C  L
ACAGCAATGCTGGAGTTTTTGTGTGGATGGATCTACGGAGGCTATTAAAA
 N  S  N  A  G  V  F  V  W  M  D  L  R  R  L  L  K
GACCAAACCTTCAAAGCTGAAATGGAGCTTTGGCGTGTGATTATCAATGA
 D  Q  T  F  K  A  E  M  E  L  W  R  V  I  I  N  E
AGTCAAGCTCAATGTTTCTCCTGGCTCATCCTTTCATGTCACTGAGCCAG    2000
 V  K  L  N  V  S  P  G  S  S  F  H  V  T  E  P
GTTGGTTTCGAGTTTGTTTCGCAAACATGGACGACAACACCGTTGACGTT
 G  W  F  R  V  C  F  A  N  M  D  D  N  T  V  D  V
GCTCTCAATAGAATCCATAGCTTTGTCGAAAACATCGACAAGAAGGAAGA
 A  L  N  R  I  H  S  F  V  E  N  I  D  K  K  E  D
CAATACCGTTGCAATGCCATCGAAAACGAGGCATCGAGATAATAAGTTAC
 N  T  V  A  M  P  S  K  T  R  H  R  D  N  K  L
GATTGAGCTTCTCCTTCTCAGGGAGAAGATACGACGAGGGCAACGTTCTT
 R  L  S  F  S  F  S  G  R  R  Y  D  E  G  N  V  L
AACTCACCGCACACGATGTCGCCTCACTCGCCGTTAGTAATAGCAAAAAA
 N  S  P  H  T  M  S  P  H  S  P  L  V  I  A  K  N
TTAATTAAAAACATTTTTCAAAATATTCATACCATTCATATAGTTTTTTT
    *
TTTTTTTTTTTTTGGGTCAATGTTGACTAAAGTTACGTATATTTTTTCC
ACAGTGGATATGATGTAAACTTCATATTTTTGGTGGGATGGTGATAGAT
GTAATGTATTTGGTTTTTCCCTTAGGGAACTCATACTTATTTATTAATGA
AATGATTGTGATTTATGAattataattgtatattttttctttaaaagtatt    2500
ttattgcaaaaataaataagtattatgaggaattgtaattgaatggaaaa
ggtatagagtcaaagggaataaacatatattttatttttttcttatggaag
ttttgttcatacttaaaatgtattatatttatggaaactttattgactttt
aaagatttgggacaaagggtatgatatgttcaagtttattacgtttgttg
gattagtcacttcattgacattgatgttttttgttgtcatattttgtcatt
attaccacacttttttttgtctaaaagcaagcttatattcaatgaggatgc
aaaaatactttataaatggtttgtctatgtttgggtctcatagatgcacc
tttatacaaaaccgttcatacaaacaaccaaattatatatgtcgatccag
aaacgctatatacaaagtcaaatactttactgacaaactacgatcgttca
```

FIG. 3D

```
ccgtcctataacatcttttcgagtctaaccattcaatgttacatcgttt        3000
ttttttttgtttggtaaatacttttcttttgctttgttaaattataa
cttgggtttgttatgtgcaatttatctatttatatgcagttaacttagtt
agcttgtattgttctagtagtgaatgactagtatcttgagttgaggggct
acctcataaaatctagtaggacgacatgatagcgtggatctgaatattat
ttatggaaggttaattaacatactcttctacaagaccataaagtcatact
aaatttgggggagtgacctcgtgtacttgccagctagtaagttacgtgta
tggtccctcaccctccctcaccctctagtcatttcgactagataaagaca
catggttgccttgacgtgatatattatttggcccaggccaaacttgatgg
tacaactgttgtgctcctaccactaaaataactgatctaggtcacacatg
gctattaggtttgttaagctttcttaatcatccttggatgcttcgaggtt        3500
tattaggttttcaggatgtctagattgtttaaatctcgaactctcatttc
taggaactctggactgcacctctaggctaatctagtttataggagcacta
tggtcctgaccactgatcttcactcacgatcctagggtactcgttctaga
atgggtgttagagttagaacagtttcacgttgacctaggtcagaacgttt
tcattagaccgaacacgctaagatcgtgagcgacaatcaatggtcaagat
tatagtgctcctataaactagattagtcccaaggtgcagtccattgtgca
tagaaatgagagttggagatttaaacaacctagatgtcctaaaacctagt
aaacctcgaaggcatccaatgatgactaagaaatcttaacaaggctatta
gcagtgtgaacggtgtcatgagagcatttgcctcctatcttcttcggtac
gtcattagctctatcaatgacctaggtcagttctttagtggcgtgtcaa        4000
gtggtaggagcacaagagttgtaccatcaagcttggcctaggccaaatag
tatagcacgtcgaggaaaccatgtgtctttatccagtcaaaatgactagg
ggacttctaaaaaaggtctctgcaccataaactgatcccgagagagggtg
agggaccatacaggtaacttagtagctgacaagcacacgaggtcgctccc
ccaaatttagtgactttatggtcgtggagaagagtatgttagttaacctt
ccataaataatgttcacatccacgatatcatacggtcgtattagatttta
tcactattgtgtttgtatgcatggttttgcataaaggtagatctgtagca
gacagtttgcgtattggaatggcaccgccattgttaagaaggtggacacc
gtgtggccgaactctgatatgaacaaaatgaagacaagacaagtggacat
atataatcccatgaaccaggtttggacgtaaaacaatataatgcctgtcg       4500
ttttcagctgcccatttcgacaaacactcatctccattgtccagtgggtt
ctccttatattcaacaaaaatttgtttgaatgtttaaagataaaaatttg
acttttaaaccaaaaccgtgataacttaggatggtgtgataatatttaag
tcccaattttcatttgaattttaaaattgtttgaaaaaaacatatatatt
ttttattaaaataaaagatgaaggttgacatcgaaatcttacgagataat
ccttatcggcgttctaacgaaattaatactatcatggtcttattctaaaa
gtctatgtcttttatgtattgtttaatcaaatatgaattacttggaaaat
```

FIG. 3E

```
gggatcttgtgtgtttgacttgagtttgaacaattgtcaaaatgttagct
gtaaagtagtcgcccttctcatccatttagtttaaaggatgtttcgagtt
taaattttcttctctcactccaagggagaatcatctatgtcattatatat        5000
gcaagggtggtttgattatgatagatagatgtacatttaacctgttaagt
aggggtcatgcggatcagagatctactttaaatggcgtagaaaatcctgt
ttaaacagggtcgggaataaggattatcatactctaccctgctcacttct
tatgtataaatatagatagaataaatgagaaattttatggaaatgaaaat
tgaagtaggaggaaggcgcagggacgggtaagacttccccgttctcacgc
ttccccataaacatcatacttcaactttgatgaagtatgaaattttgttt
ggtggatatccaataagtctcattgcactaaacaaagccagggaagagtt
cataaataagacgtaaagttgtggtctccaacacgtaaaacatagttact
cctcttgatttcccatgtaattgagaatttagagctttagtgtgtttaga
cgaggaagattgctttcactgaacactgagttgttccctaaatctatttg        5500
ttacaacgaggtttatcactgcttaagtgatgtaatttaggttttaattt
ctagaaaacgtgactatgtgtaatgtcagacttgttaggactttgagcat
aagctctcatgtctttgatttgaactttcttaaaaagtttcataccaatg
gagatgtattcctcgtttataaactcaagatcattcgctaacgtgggact
tccttccgataatcctcaacaaaactcagtattaacttcagtttgtttgg
tgaagtgttagacccttttctttaatcacatgcaatcatggtgagatttgt
cttttcataaaatattatggccttatattctatttccagtctgaacaga
gttgaatgagttgtacttctctacaatcagcccatgcacacatacgagaa
cccaccagacggactcatgtctaaacaaaagggaagaatcacattagagg
gtgaagaagaaacattttacacaagtgctcggagcaacaatacgtcattt        6000
accaaacatggatataaaaatggtgacaaaggaagaagctatcaagcaca
atcagggagagctcagaagaacgacaacaataactctcaagtgaagagat
tttggggtatttactacaactgcggaaaaagggctacatgtccagagatg
gttggtctaagaaaattttttgttgaaagcaatgtggcaacatccaaaaag
gagatggaagataaatgggatgcagaggcaatatgtgtcgtagaagaaga
cgagctagcacttatggtaataaagagagaacatattgattatgaggatg
actgaatcattgattcaggatgcttaaaccacatgattaacaatcagagt
ggaacaattggatgcggagtggccctcagagaatgaagtatttcaaggct
tggaattc
```

FIG. 3F

```
           10        20        30        40
                               aagcttaatgactacgaatcaa
      gctacttatcatccattaatcatttaatatacctcaatacgtctaactca    -2501
      atcatgttctcatcatattttttgacgtttaactgttcgtggggttggattg
      ggttgaattgaaacggttcttagatctaactaaattgttcgagtttcaac
      tttgattaaataatgaactcaactcaacccaaccgaatcataaagttttg
      gattgaacttgtttgggtaacctaattctatacaagcaagttcgtaatcc
      aaatgaaactatatatattgagttaagctgatcgaattttttcgaattcaa
      attttgttgattatcttctcattgttctatcaacctttgtatagttcttt
      gtcacaaaaacaaatcctcaccgaccatactattaattgtgatctaacgt
      aaaaaaaacgtttgtttatgtaacactttaatgatcatatttctagattc
      actaaaaagatcatgtacaaacaaaatagtcgatcacaaagactatattc
      agaagccaattttttattttaattcgactcgttttgaatctgtgtttttt    -2001
      ttttttttttttttgaatctagacgaagaataacaaaaatctctccaaaatt
      cgatctccattgacttttttggtaccgatccattaatgaacgtgggtttga
      ttttagaagccctattgaattttcttgtttgaatttattaatcttctttg
      attgcgattgaccaattgatttggttgagactcaaaatcccaaaacatac
      aaaagtcttaatgtaacaacgaactcatgaacatatcgttaatgcataca
      tatcacaaaagcgtttcaacacatttgagtaaaagtgacgaaaagctgaa
      ctttttttaaaacaaacttcgaaccttttaacttttttatatgaattgaaca
      taacaacaaaatgttaacattgtattgacatcattatatttaacaatttt
      ccaccgaccatactactaattgtactcttaaatggaagttcttattttcg
      ttctcaaatattctaatcgttttttattcattcatcgttcaacagctactc    -1500
      ttatgcattattttcttccgtttatcaatttacatttctagatccactaa
      aagttcataaacaaacaaaatagtcgatcccagtcgatcccaccgaccat
      cttcctatagaagccaattttttattttaattcgactcattttgaaattat
      gttatttccccaaaattcatctccttcaactttttggtgccaatccatta
      atgaacgtgagggttggtttagaagtccattgggttttgttgtatgattta
      attattttctttgccaacttttttcgtggtcaagcccatcgatttaaatat
      ttattatttgtttcttatcattttcttatcggctaatacgatagttttct
      atttgagcgagaaaaagcgtgctaggagattcatattggtttgtgggatt
      gtctaaacgtgaccatttgtaggagatgcaagggaataatgagacataca
      tgtgctgaattcagattcagaattgtttcaaattccgagcatggatactt    -1001
      cgtaaaagttgaaaaaccatgcacacctcgaacgagtgaacaataatatt
      gcctttctttcgccccatactcaagaaagcttgggacgctacataagaa
      gttaaattaggtatcattgaaataggatatatttgtacttgtatgatgta
      ttgtcatacttctcgacttcatctaattatagagtttcgaagttttcata
      ctttcccattttttgttgaaaatgtattattgcacgagtgcagttggatta
      aacatctgaaccccaacgagaattaattttctcgaatttttcatttacga
```

FIG. 4A

```
tcaagcttccagaattttattgaaaaccttagagatcgaatttaggaata
cagtagaagagaatgatgctcggaatgttttctagaagctcgaaaaaata
taaaataaaatcgtagaaaataaaaaaatgtgtggtcaaagtcaatagaa
ttttgcccctcctagtattttggagaccctcgaaaaacccgagtgaatga         -501
tcattttaggtttcggttttcctcaaaatctaaagtgtatgaagaaatta
gcatatgaaaatttagtatgttgatcttgtcatgatttcgcacattttttc
ttaaaagaacctgaagtcaaatcataacggaactaggagatcgaagaaga
cccaagaacggtataaacacataaatatgaaggttttgagaggggacgaa
agactacataagtagtatattgaggagctattattgtgtatggaggaagc
ccactctgagaggagatgagagactacaaaagtagatcagctgtgtctcg
aagcctaaaaaattgggttgtgacattgaaagttcgattttttcctaaggt
gacataaggggatctataacatcgtactctttgttttgttccaatttcct
acacacacgacttggtcggctgtttgtggcttgtcttttttacatggtttc
aacgtgaccctgggcttataaattcactcccattttgttctttctttcgt          -1
atcttaacaacccaaaagctctcattttttagggacacaaaaacaaacacc
tcaacaactttcaaATGGGGTTTCATCAAATTGACGAAAGGAACCAAGCT          100
              M  G  F  H  Q  I  D  E  R  N  Q  A
CTTCTCTCTAAGATCGCTATCGACGATGGCCATGGCGAGAACTCAGCCTA
 L  L  S  K  I  A  I  D  D  G  H  G  E  N  S  A  Y
TTTCGATGGGTGGAAAGCTTATGATAACAATCCGTTTCACCCCGAGAATA
  F  D  G  W  K  A  Y  D  N  N  P  F  H  P  E  N
ATCCTTTGGGTGTTATTCAAATGGGTTTAGCAGAAAATCAAgtttcgtat
 N  P  L  G  V  I  Q  M  G  L  A  E  N  Q
atagtgttttcatgttttctttatatcatttcacgtttgaaaatttcgct
aactttgtttctgtgtgaatttcgatagCTTTCTTTTGGTATGATTGTTG
                              L  S  F  G  M  I  V
ACTGGATTAGAAAACACCCCGAAGCTTCGATTTGTACACCTGAAGGACTT
 D  W  I  R  K  H  P  E  A  S  I  C  T  P  E  G  L
GAGAAATTCAAAAGCATTGCCAACTTTCAAGATTATCATGGCTTACAAGA
 E  K  F  K  S  I  A  N  F  Q  D  Y  H  G  L  Q  E
GTTTCGAAAAgtactagatatgatattctaactatatctaaactcagaag                                                                500
 F  R  K
cttaagtcgatggattatgatatatatatatatattttatttttcagGCG
                                                 A
ATGGCGAGTTTCATGGGGAAGGTAAGGGGTGGGAGGGTGAAATTCGACCC
 M  A  S  F  M  G  K  V  R  G  G  R  V  K  F  D  P
GAGTCGGATTGTGATGGGTGGCGGTGCGACCGGAGCGAGCGAAACCGTCA
  S  R  I  V  M  G  G  G  A  T  G  A  S  E  T  V
TCTTTTGTTTGGCGGATCCGGGGGATGCTTTTTTGGTTCCTTCTCCATAC
 I  F  C  L  A  D  P  G  D  A  F  L  V  P  S  P  Y
```

FIG. 4B

```
TATGCAGCgtaagttttttttttttttttttcttttaaatctctcctttt
 Y  A  A
cactttacatatagagagagaaaccatttgacaaattattaactctacaa
attctctttgaaagtcgtatgttttgggagggtccaaacttcaaccattc
taccaagtaaacaatccacctctttcatgcctcattgctggcatacctcc
tcgtcttctccctatactttctttctttgtattcttctccctaaccgatg
tgtaatttcacaatctactccttcgagctccagcattcttgttggcacac          1000
cactttgtgtccactcccttcgaggctcagccttctcgctagctcattg
ctcggtgtctggttctaatatcatttgtaacagtccaagtccaatgctag
tagatattgtcctcgctttgggctttccctctcggacattccatcaagtt
tttagaacacgtctgctaagaaaaagttttcacacccttataaataatgc
ttcgttctcctccctaaccgatatgggatctcactgaatattacccactt
gaataaactaataacttgtgctcttcgttcttgatatgaaaatcaacccg
atggaaagaactgatgtcaaatgataagaaaatcactataagggaagtaa
gattcggattaccttgttgatcgaatatctcaaggcaagaacacttgttt
gaaattcgaatcactccacaaccaagattgatcatgttgagcttgaatga
ttctgcatgcaatctaaactacatagaattacaaagaaacttagtcattg          1500
gctaaagaaagcacaaatgtttcttttactatattttccaagtcggctta
caaatacaacatacatgacttcgtataatctcaaaatgaaactatttaag
gcattataagagtggtaacattcataatttatgaccataattaaccatta
tgtaaatataatctaaggtaaataaaaagccttaaaacatattaatgaaa
tacaataactccaaattttctagattgtaatccacccaaaatttataaaa
atgaaacttcattcttcttcaatgtgacatgtggcatgaactgaaatatc
tattttcttcccatgttcatcgaaatatagtgtatgattgatgtctcttg
gttcatatcagttctttacatatattaataaccttttggtacgaggtgaa
caatgtcgtattattgtaaaaatactcaaaagtctttgtcctaacaatca
gtacgttgttttcagGTTTGATCGAGACCTAAAATGGCGAACACGAGCA          2000
                 F  D  R  D  L  K  W  R  T  R  A
CAAATAATTCCTGTTCATTGCAACAGCTCGAACAACTTCCAAGTCACAGA
 Q  I  I  P  V  H  C  N  S  S  N  N  F  Q  V  T  E
GGCAGCCTTAGAAATAGCCTATAAAAAGGCTCAAGAGGCCAACATGAAAG
  A  A  L  E  I  A  Y  K  K  A  Q  E  A  N  M  K
TGAAGGGTGTTATAATCACCAATCCCTCAAATCCCTTAGGCACAACGTAC
 V  K  G  V  I  I  T  N  P  S  N  P  L  G  T  T  Y
GACCGTGACACTCTTAAAACCCTCGTCACCTTTGTGAATCAACACGACAT
 D  R  D  T  L  K  T  L  V  T  F  V  N  Q  H  D  I
```

FIG. 4C

```
TCACTTAATATGCGATGAAATATACTCTGCCACTGTCTTCAAAGCCCCAA
  H  L  I  C  D  E  I  Y  S  A  T  V  F  K  A  P
CCTTCACCAGCATCGCTGAGATTGTTGAACAAATGGAGCATTGCAAGAAG
  T  F  T  S  I  A  E  I  V  E  Q  M  E  H  C  K  K
GAGCTCATCCATATTCTTTATAGCTTGTCCAAAGACATGGGCCTCCCTGG
  E  L  I  H  I  L  Y  S  L  S  K  D  M  G  L  P  G
TTTTCGAGTTGGAATTATTTATTCTTACAACGATGTCGTCGTCCGCCGTG
  F  R  V  G  I  I  Y  S  Y  N  D  V  V  V  R  R
CTCGGCAGATGTCGAGCTTCGGCCTCGTCTCGTCCCAGACTCAACATTTG
  A  R  Q  M  S  S  F  G  L  V  S  S  Q  T  Q  H  L
CTCGCCGCCATGCTTTCCGACGAGGACTTTGTCGACAAATTTCTTGCCGA        2500
  L  A  A  M  L  S  D  E  D  F  V  D  K  F  L  A  E
GAACTCGAAGCGCCTGGGCGAGAGGCATGCAAGgtttgttaaactacacc
  N  S  K  R  L  G  E  R  H  A  K
attattatttgtgggattgaaaagcattacaaaatgcaattaatttaaga
atgtattaatcaaattcagGTTCACAAAAGAATTGGATAAAAATGGGGATC
                      F  T  K  E  L  D  K  M  G  I
ACTTGCTTGAACAGCAATGCTGGAGTTTTTGTGTGGATGGATCTACGGAG
  T  C  L  N  S  N  A  G  V  F  V  W  M  D  L  R  R
GCTATTAAAAGACCAAACCTTCAAAGCTGAAATGGAGCTTTGGCGTGTGA
  A  I  K  R  P  N  L  Q  S  *  N  G  A  L  A  C (check)
TTATCAATGAAGTCAAGCTCAATGTTTCTCCTGGCTCATCCTTTCATGTC
  I  I  N  E  V  K  L  N  V  S  P  G  S  S  F  H  V
ACTGAGCCAGGTTGGTTTCGAGTTTGTTTCGCAAACATGGACGACAACAC
  T  E  P  G  W  F  R  V  C  F  A  N  M  D  D  N  T
CGTTGACGTTGCTCTCAATAGAATCCATAGCTTTGTCGAAAACATCGACA
  V  D  V  A  L  N  R  I  H  S  F  V  E  N  I  D
AGAAGGAAGACAATACCGTTGCAATGCCATCGAAAACGAGGCATCGAGAT
  K  K  E  D  N  T  V  A  M  P  S  K  T  R  H  R  D
AATAAGTTACGATTGAGCTTCTCCTTCTCCGGGAGAAGATACGACAAGGG        3000
  N  K  L  R  L  S  F  S  F  S  G  R  R  Y  D  K  G
CAACGTTCTTAACTCACCGCACACGATGTCGCCTCACTCGCCATTGGTAA
  N  V  L  N  S  P  H  T  M  S  P  H  S  P  L  V
GAGCCAGAACTTATTAAagatgagtttgagaagatattatcataagtttt
  R  A  R  T  Y  *
ttttagctcattaatgaatggatggatatttaaaactatgaagtgtagca
ctcatgctccgaaggaattaatttcttgattgctgaattttaagacgata
taaaagagaaaaaatgtttagaaaaatctaaaaaatgggagaaaaaaaag
```

FIG. 4D

```
aaaacaattaaaatttaaaaatcagtcaaaatcattaaagtagtacatat
agctcatactagaaggtgagacaagactctgaaatgattttatgatacg
tctttaactacgattgcatttcttgactggggttactgcatttcttgact
ggggttacttactaagtatttctagaaatactcaagtcacatgctactct
tattttcaggtaaaggcaatgtacctcttcacggacgatgacgtcgcggt
gacgccatgagattgaagctagggtagaagtattcatgttattttgtag
cccttaggttagatcaaaatatcgtcttattttattttatcaaa
attttacgtgatttgttttccattttaattgttcaataattttattatga
acatgtaagttcatggcacttttttaaaatattttaaaagttttttttt
tcgattcttaattaatttatgcatgtagtagcgagtttatcatagtcaag
gaggatgttttgtgaaatgttaagctgaatggttatgtgtaaaacggaga
gtctactaatgctattaagattttatgtaaacaagtcttccacttgatt
tctgtcttgatttgctacatctcgatttcttccgtcaagaatttctctct
aacgaaatgataatgcacctccacatgttttattctagcatgaaacatcg
aatttctgttaggcaaatcgcagattggttgttgtaatgaagtggtatt
ggatagtcaattttcttgtccgatctttcatcaagagtttcagtcatgt
actttcctaaactgctccaaccgctactctgtactctacttctctagttg
acaatgatactgttgattttcttttgctacactgagaagttgttctcgaa
ccgagcttgaacacatacctggtgcttgatcttcgggtattgtgatattc
tacatagtcagcatcacggtatctggataacttgtagtcttcgcttcttt
tatacaaacgatcataatgattgtgcctttgacatatctcaaggtccgtc
aagtcgcatccaaatgaggtttctttgcactttgtatgtactgactaatg
actccaactccgttctcaaatttcttcggttggttcatgtagatctctct
atttaactctccgtgcaagaaagcattcttcatatccatctgtcgtaatt
tccaatctttatttaccacaagtgctggaggaacctatatgatggtgatc
tttgccactgaactaaatgtttcatcatagtccatattgttgagagaacc
ctggagctacagtctgagttgtgtatctcactattcatccattcgggata
cactttattttgtaaatccacttgcaaaagatggatttgacatcttctgg
tctttgtactaattcccaggtttgatttatctcgaagggtataattttctt
cctccattgtctgctgccaagccgtattgcgtgatgcttctttatacgtc
tctagctctttactttgtcttctaaaatagttatattgaacatactttgg
atttggcttatggattctttctaaccatctaagtcgttgaggtgtcattt
ccttttcactaggttcgcttgattgagtcactccttgctcaccaacatta
gtgtcacttggatatttagacacatcagcatttaagaaaatgtgtacagt
tttctccccgtattctgtggaagaatttcttcagtttgctcccccgtct
tctgtggaagaattc
```

```
                    10         20         30         40
                    .          .          .          .
ptACCI→ tgtagttgtgtacattttattaatcttcatcttcttaattctcttcagtt
        tttaatttcttcacttctaaactcatttagtaaaaaaaaaaATGGGATTTG    100
                                                  M  G  F
        AGATTGCAAAGACCAACTCAATCTTATCAAAATTGGCTACTAATGAAGAG
         E  I  A  K  T  N  S  I  L  S  K  L  A  T  N  E  E
        CATGGCGAAAACTCGCCATATTTTGATGGGTGGAAAGCATACGATAGTGA    200
         H  G  E  N  S  P  Y  F  D  G  W  K  A  Y  D  S  D
        TCCTTTCCACCCTCTAAAAAACCCCAACGGAGTTATCCAAATGGGTCTTG
         P  F  H  P  L  K  N  P  N  G  V  I  Q  M  G  L
        CTGAAAATCAGCTTTGTTTAGACTTGATAGAAGATTGGATTAAGAGAAAC    300
         A  E  N  Q  L  C  L  D  L  I  E  D  W  I  K  R  N
        CCAAAAGGTTCAATTTGTTCTGAAGGAATCAAATCATTCAAGGCCATTGC
         P  K  G  S  I  C  S  E  G  I  K  S  F  K  A  I  A
        CAACTTTCAAGATTATCATGGCTTGCCTGAATTCAGAAAAGCGATTGCGA    400
         N  F  Q  D  Y  H  G  L  P  E  F  R  K  A  I  A
        AATTTATGGAGAAAACAAGAGGAGGAAGAGTTAGATTTGATCCAGAAAGA
         K  F  M  E  K  T  R  G  G  R  V  R  F  D  P  E  R
        GTTGTTATGGTTGGTGGTGCCACTGGAGCTAATGAGACAATTATATTTTG    500
         V  V  M  V  G  G  A  T  G  A (N) E  T  I  I  F  C
        TTTGGCTGATCCTGGCGATGCATTTTTAGTACCTTCACCATACTACCCAG
         L  A  D  P  G  D  A  F  L  V  P  S  P  Y  Y  P
        CATTTAACAGAGATTTAAGATGGAGAACTGGAGTACAACTTATTCCAATT    600
         A  F  N  R  D  L  R  W  R  T  G  V  Q  L  I  P  I
        CACTGTGAGAGCTCCAATAATTTCAAAATTACTTCAAAAGCAGTAAAAGA
         H  C  E  S  S  N  N  F  K  I  T  S  K  A  V  K  E
        AGCATATGAAAATGCACAAAAAATCAAACATCAAAGTAAAAGGTTTGATTT    700
         A  Y  E  N  A  Q  K  S  N  I  K  V  K  G  L  I
        TGACCAATCCATCAAATCCATTGGGCACCACTTTGGACAAAGACACACTG
         L  T  N  P  S  N  P  L  G  T  T  L  D  K  D  T  L
        AAAAGTGTCTTGAGTTTCACCAACCAACACAACATCCACCTTGTTTGTGA    800
         K  S  V  L  S  F  T  N  Q  H  N  I  H  L  V  C  D
        CGAAATCTACGCAGCCACTGTCTTTGACACGCCTCAATTCGTCAGTATAG
         E  I  Y  A  A  T  V  F  D  T  P  Q  F  V  S  I
```

FIG. 5A

```
CTGAAATCCTCGATGAACAGGAAATGACTTACTGCAACAAAGATTTAGTT    900
 A  E  I  L  D  E  Q  E  M  T  Y  C  N  K  D  L  V
CACATCGTCTACAGTCTTTCAAAAGACATGGGGTTACCAGGATTTAGAGT
 H  I  V  Y  S  L  S  K  D  M  G  L  P  G  F  R  V
CGGAATCATATATTCTTTTAACGACGATGTCGTTAATTGTGCTAGAAAAA    1000
  G  I  I  Y  S  F  N  D  D  V  V  N  C  A  R  K
TGTCGAGTTTCGGTTTAGTATCTACACAAACGCAATATTTTTTAGCGGCA
 M  S  S  F  G  L  V  S  T  Q  T  Q  Y  F  L  A  A
ATGCTATCGGACGAAAAATTCGTCGATAATTTTCTAAGAGAAAGCGCGAT    1100
 M  L  S  D  E  K  F  V  D  N  F  L  R  E  S  A  M
GAGGTTAGGTAAAAGGCACAAACATTTTACTAATGGACTTGAAGTAGTGG
 R  L  G  K  R  H  K  H  F  T  N  G  L  E  V  V
GAATTAAATGCTTGAAAAATAATGCGGGGCTTTTTTGTTGGATGGATTTG    1200
 G  I  K  C  L  K  N  N  A  G  L  F  C  W  M  D  L
CGTCCACTTTTAAGGGAATCGACTTTCGATAGCGAAATGTCGTTATGGAG
 R  P  L  L  R  E  S  T  F  D  S  E  M  S  L  W  R
AGTTATTATAAACGATGTTAAGCTTAACGTCTCGCCTGGATCTTCGTTTG    1300
  V  I  I  N  D  V  K  L  N  V  S  P  G  S  S  F
AATGTCAAGAGCCAGGGTGGTTCCGAGTTTGTTTTGCAAATATGGATGAT
  E  C  Q  E  P  G  W  F  R  V  C  F  A  N  M  D  D
GGAACGGTTGATATTGCGCTCGCGAGGATTCGGAGGTTCGTAGGTGTTGA    1400
  G  T  V  D  I  A  L  A  R  I  R  R  F  V  G  V  E
GAAAAGTGGAGATAAATCGAGTTCGATGGAAAAGAAGCAACAATGGAAGA
  K  S  G  D  K  S  S  S  M  E  K  K  Q  Q  W  K
AGAATAATTTGAGACTTAGTTTTTCGAAAAGAATGTATGATGAAAGTGTT    1500
  K  N  N  L  R  L  S  F  S  K  R  M  Y  D  E  S  V
TTGTCACCACTTTCGTCACCTATTCCTCCCTCACCATTAGTTCGTTAAga
  L  S  P  L  S  S  P  I  P  P  S  P  L  V  R  *
cttaattaaaagggaagaatttaatttatgttttttatattttgaaaaa      1600
aatttgtaagaataagattataatataggaaaagaaaataagtatgtaggat
gaggagtattttcagaaatagttgttagcgtatgtattgacaactggtct    1700
```

FIG. 5B ptACC1 —atgtacttagacatcataatttgtcttagctaattaacgaatgcaaaagt
        gaagttatgttatgactcttagaat
ptACC2 —atgtacttagacatcataatttgtcttagctaattaatgaatgcaaaagt
        gaagttatgttatgactcttagaatcttttgatttattggactttctcga    1800
ptACC3 —atgtacttagacatcataatttgtcttagctaattaatgaatgcaaaagt
        gaagttatgttatg(a)$_{19}$
ptACC4 —atgtacttagacatcataatttgtcttagctaattaatgaatgcaaaagt
        gaagttatgtt(a)$_{20}$
ptACC5 —atgtacttagacatcataatttgtcttagctaattaatgaatgcaaaagt
        gaagttatgtt(a)$_{19}$
ptACC6 —atgtacttagacatcataatttgtcttagctaatt(a)$_{58}$ ptACC2 —ttatat tgtt(a)$_8$

FIG. 5C

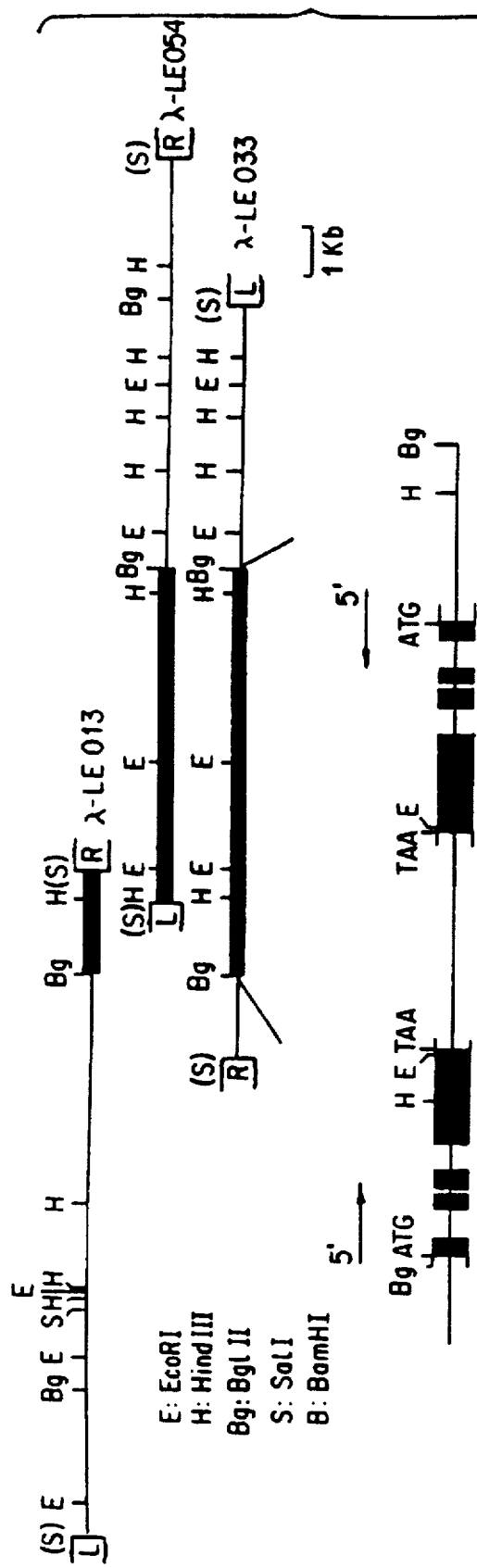
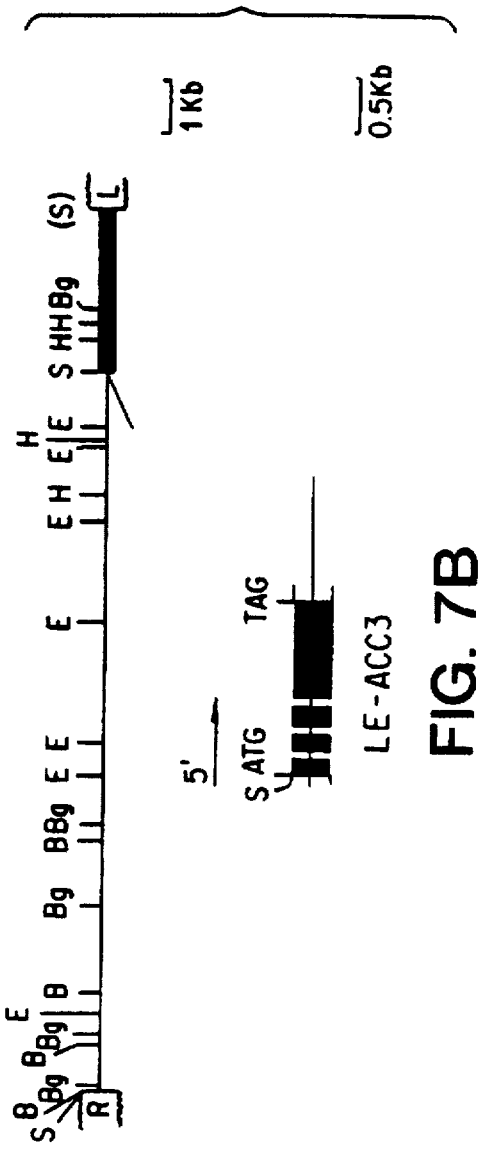
FIG. 7A
FIG. 7B

```
                         10        20        30        40
                         •         •         •         •
                             ggatcctcattacttgtctatggctaaagtgtt
           aaagaattattcacaatatctaacacatttaatgactattcaactaatag
           tgacgatcttttaaaataaaatgaagaacttaaaattttgaccaacttcc
           taacgatattaatgagggatacagatttgatttacgcaaaaaaaaaagaa
           aaaaagaaatgatattactcaattataaatttgattagagaatagctagg
           cctataattgttttacattatctattcctaagttatgatattatccttca
           atttacctgatagcgtaaaaattacaataatttgtacactaatgatgcac
           aaaacttaaattcattatatatacacatacaaggccgagggcttaataga   -2501
           atcgatgacctgaaatcatatttctattgtttagcaatagaaattagtta
           tggcttcaaatttagcgatgaattccatgggtgtttgcattgacttaaaa
           gatgatcaaatctactttgaagtccgttttttgaattttgaaagtgtttga
           taaatataaaaataactaaaaataagttaggaagtgtttgacaaagttaa
           atcttaaaataatttatcaaccaaaagtaggtctccctattcttttttt
           ttttggacttaaaagtcgtttaaacgtaatttgacttataaatttttaa
           agttaatttaaaccggctttgtaaaagaaattaacaattcatttggaatg
           ttaattattaaaagatccagatatgtacaaaataaaaataacctacctcc
           tatagtaaagattttcaaacaatattaagttaaacaaagtcaaaaagttg
           gtatattgaattttactagtcttgtataaaccaatacaattagcttcgaa   -2001
           aagtcattgatatattttctatgtgctgcttgttgggaaacttcctgta
           acacaaagaatgaatgaattctcccacattttttatttgtagatttaatt
           ccctatttgatatcaaaaatattctggagaaggaaggaatacgagcctaa
           ccaagactaggccaattaagcagcccatgataagcctccattcaaatgaa
           atatcaaaatcactgtattattataagatactttgagaatatatattgtt
           tggtcaaatagtttattaacatatatattatatataagtatgtgaaatga
           tgaagctagagttttatatgaacatataatttagattttaagttgtatat
           tttgctcataaatataaaattctatgaattgtaaaattatcaatatttac
           ttaattctttacgcaatcttactaaatatataaaagttaataactacaaa
           agtataatcatacgatcacaaacgagctattctaaaaaaagtatcacata   -1501
           tttaatataatcctcccacatagtacaaacaatcttctcatgttttgtaa
           taataaatgatgtaagggtttaaaggtggtgtgaataataattgcaacta
           aaaaatttatttacatctaaaataaataattaatacatataaaatcgtat
           gatcaaaatttaaaatttaaatcatgatatgtaattaatatgtccagac
           acctgcttaataaaaactatacactattaatgcagtatgcactttataca
           tattttgtaaattagataattaaatggccggctagagtaatgcaatacga
           tagaaaagctcgatcaaaattaatcacactcaatgtgcctagtaagatct
           tcaaatcaaaatcaattatgattatcatctgcggtccattgttctcgtcc
```

FIG. 9A cttcccaggaaagtaattatccctattatattttttatttatttatatana
ctacttgaaaaaggtaaaaagaataaatanataaattaccagtagtacca      -1001
ttgtattctcaacttttttctttctcacgtgtagcttctagcttgaacat
gaaatttcatataactatttagacgaaggcaattacgactaagggtatgt
tcgataagaaaagaaaatattttcttaaaaaataaataaatttttaattt
attttcatatttgattaataagcagaaaatattttgaggaagtatctt
ttttattttgagaaaatactttctatgaaaataattattgatgtgaaa
atcaatctcgataattgttgcaggaaacgactctgacaatcgaattagga
taaaacctcgatgacctttaaaatcgaccctaaaatctgatccaaaactc
gatccagacttccgatccaaaacttgattcaagtaaatattttttaaaaat
aaattcttttgacagggtggcgtaaaaataattttattttaaaatatga
tatagttttctaaaatatatttttttgtttggttattgggggttggttcg       -501
aggctagggataaaataattaaaacataagaaattttaaaagtttttaat
tgcatttttttttgtgttggggaggggcggattttgggttggataagaaaa
aatatttaaagataaaatagaattttggaaaatattttttcttaattttttg
aaggaaatcattttcttaaatttgagaaaaatgaattattcttaaaaa
aaatttccaaaaacatttaagctaccaaatatgaaaaaataaaaaatatt
tttttttcctaccaaatgcaccctaaattagtcaaatatccaacatttaaa
agagctatgaaaaaaaaaaagaagtaagaatcgtagatcttcttttaatg
cgtacttttattttccaagatttgaacaataaaatagacttttctattt
tattttctgatgtaattctttatatacgttagtcgacatgttctcattaca
tacttcagtctttccccttatatatatccctcacattccttaattctctt       -1
ACACCATAACACAACTACAACAAACACATAATACTTTTAATACAATTAGT
TATTTATTAGAAGTATTTAAAGTAAAGCACTTGTGAGTTGTGTACATTTT       100
ATTAATCTTCATCTTCTTAATTCTCTTCAGTTTTTAATTTCTTCACTTCT
AAACTCATTTAGTAAAAAAAAAAATGGGATTTGAGATTGCAAAGACCAACT
                                 M  G  F  E  I  A  K  T  N
CAATCTTATCAAAATTGGCTACTAATGAAGAGCATGGCGAAAACTCGCCA
 S  I  L  S  K  L  A  T  N  E  E  N  G  E  N  S  P
TATTTTGATGGGTGGAAAGCATACGATAGTGATCCTTTCCACCCTCTAAA
  Y  F  D  G  W  K  A  Y  D  S  D  P  F  N  P  L  K
AAACCCCAACGGAGTTATCCAAATGGGTCTTGCTGAAAATCAGgtaatta
  N  P  N  G  V  I  Q  M  G  L  A  E  N  Q
attatcctttatttatatattttgcagtttgaccaaacagactattataa
tttttttctgaaacctcgatggtgttaaatttcttttgtagCTTTGTTTA
                                             L  C  L
GACTTGATAGAAGATTGGATTAAGAGAAACCCAAAAGGTTCAATTTGTTC       500
  D  L  I  E  D  W  I  K  R  N  P  K  G  S  I  C  S

FIG. 9B

```
TGAAGGAATCAAATCATTCAAGGCCATTGCCAACTTTCAAGATTATCATG
  E  G  I  K  S  F  K  A  I  A  N  F  Q  D  Y  N
GCTTGCCTGAATTCAGAAAAgtacatatcgtactatagtcagttaaatta
  G  L  P  E  F  R  K
tattgatagtataaaaattcgttaatatatttaactaacgagtttattta
atcagGCGATTGCGAAATTTATGGAGAAAACAAGAGGAGGAAGAGTTAGA
       A  I  A  K  F  N  E  K  T  R  G  G  R  V  R
TTTGATCCAGAAAGAGTTGTTATGGCTGGTGGTGCCACTGGAGCTAATGA
  F  D  P  E  R  V  V  M  A  G  G  A  T  G  A  N  E
GACAATTATATTTTGTTTGGCTGATCCTGGCGATGCATTTTTAGTACCTT
  T  I  I  F  C  L  A  D  P  G  D  A  F  L  V  P
CACCATACTACCCAGCgtaagtatatttaattatatatgtgtaaaaaaaa
  S  P  Y  Y  P  A
ttaaaatcatcaaatcattttttttatttgtattaccaaataaattgtct
aattttcaagattgtaacacattcatcaaagtacctaataatataaacga
ttcagtatattaacgatgtatataatttaattcctttggcggatttgtct
ttttatgttgggccatcagaagaacattctggtgtattaattaattaatt
aattaataatagatgtgttg cattctttttttaagacagcgagagtttaa
ttagtcttaattactggattatcacgcaagctctttcttgaattttatta
ttcttatattaaacacatgatagcataatatctttcttttgtggaatcca
gcttgttcgtgaagctttgtattcacacttataaaacaacaaaaaataaa
atctggtggtaattgattaaagagagaaatataaaaaaataatagtcaaa
tagactaataaggaaagaaataaaaaatacacaaaatactaaaaaaaaag
aattaaggtatagtggtctattattgagaacttttttgaagaattgaacc
ccactttaatttcttgcttgacccgtgaccattgcttatcgaggtaaaat
aaaatttcaaacattgactatgacttgttagagagtaattaccacaagtc
aaaattttgttactctgtctcgttatttcattaggatcgataagataaca
tctaacatatatatcttttttattagtacttgtttattttttagtaaaagc
acgttatacattttacaatagtcaattgttgcatatattagtatatatat
tttgctaagtcctaactaacaatattttggcaattgactaatgcagATT
                                                F
TAACAGAGATTTAAGATGGAGAACTGGAGTACAACTTATTCCAATTCACT
  N  R  D  L  R  W  R  T  G  V  Q  L  I  P  I  N
GTGAGAGCTCCAATAATTTCAAAATTACTTCAAAAGCAGTAAAAGAAGCA
  C  E  S  S  N  N  F  K  I  T  S  K  A  V  K  E  A
TATGAAAATGCACAAAAAATCAAACATCAAAGTAAAAGGTTTGATTTTGAC
  Y  E  N  A  Q  K  S  N  I  K  V  K  G  L  I  L  T
CAATCCATCAAATCCATTGGGCACCACTTTGGACAAAGACACACTGAAAA
  N  P  S  N  P  L  G  T  T  L  D  K  D  T  L  K
```

FIG. 9C

```
GTGTCTTGAGTTTCACCAACCAACACAACATCCACCTTGTTTGTGACGAA
 S  V  L  S  F  T  N  Q  N  N  I  N  L  V  C  D  E
ATCTACGCAGCCACTGTCTTTGACACGCCTCAATTCGTCAGTATAGCTGA   2000
  I  Y  A  A  T  V  F  D  T  P  Q  F  V  S  I  A  E
AATCCTCGATGAACAGGAAATGACTTACTGCAACAAAGATTTAGTTCACA
   I  L  D  E  Q  E  M  T  Y  C  N  K  D  L  V  N
TCGTCTACAGTCTTTCAAAAGACATGGGGTTACCAGGATTTAGAGTCGGA
  I  V  Y  S  L  S  K  D  N  G  L  P  G  F  R  V  G
ATCATATATTCTTTTAACGACGATGTCGTTAATTGTGCTAGAAAAATGTC
   I  I  Y  S  F  N  D  D  V  V  N  C  A  R  K  M  S
GAGTTTCGGTTTAGTATCTACACAAACGCAATATTTTTTAGCGGCAATGC
   S  F  G  L  V  S  T  Q  T  Y  F  L  A  A  N
TATCGGACGAAAAATTCGTCGATAATTTTCTAAGAGAAAGCGCGATGAGG
   L  S  D  E  K  F  V  D  N  F  L  R  E  S  A  N  R
TTAGGTAAAAGGCACAAACATTTTACTAATGGACTTGAAGTAGTGGGAAT
   L  G  K  R  N  K  N  F  T  N  G  L  E  V  V  G  I
TAAATGCTTGAAAAATAATGCGGGGCTTTTTTGTTGGATGGATTTGCGTC
   K  C  L  K  N  N  A  G  L  F  C  W  M  D  L  R
CACTTTTAAGGGAATCGACTTTCGATAGCGAAATGTCGTTATGGAGAGTT
   P  L  L  R  E  S  T  F  D  S  E  M  S  L  W  R  V
ATTATAAACGATGTTAAGCTTAACGTCTCGCCTGGATCTTCGTTTGAATG
   I  I  N  D  V  K  L  N  V  S  P  G  S  S  F  E  C
TCAAGAGCCAGGGTGGTTCCGAGTTTGTTTTGCAAATATGGATGATGGAA   2500
   Q  E  P  G  W  F  R  V  C  F  A  N  N  D  D  G
CGGTTGATATTGCGCTCGCGAGGATTCGGAGGTTCGTAGGTGTTGAGAAA
   T  V  D  I  A  L  A  R  I  R  R  F  V  G  V  E  K
AGTGGAGATAAATCGAGTTCGATGGAAAAGAAGCAACAATGGAAGAAGAA
   S  G  D  K  S  S  S  M  R  K  K  Q  Q  W  K  K  N
TAATTTGAGACTTAGTTTTTCGAAAAGAATGTATGATGAAAGTGTTTTGT
   N  L  R  L  S  F  S  K  R  M  Y  D  E  S  V  L
CACCACTTTCGTCACCTATTCCTCCCTCACCATTAGTTCGTTAAGACTTA
   S  P  L  S  S  P  I  P  P  S  P  L  V  R  *
ATTAAAAGGGAAGAATTTAATTTATGTTTTTTTATATTTTGAAAAAAATT
TGTAAGAATAAGATTATAATAGGAAAAGAAAATAAGTATGTAGGATGAGG
AGTATTTTCAGAAATAGTTGTTAGCGTATGTATTGACAACTGGTCTATGT
ACTTAGACATCATAATTTGTCTTAGCTAATTAATGAATGCAAAAGTGAAG
TTATGTTATGACTCTTAGAATCTTTTGATTTATTGGACTTTCTCGATTAT
ATTGTTAttattaaatttcatatattttatatatttaaaaagtgtcgtaa   3000
```

FIG. 9D

```
gtcataataattgacaagatatatgaaaactttacgatcaaagataaatt
tgtttaaattttaaaatttaaagtgtgtcacataaattgagatggagaga
ttatggtgtttgtgtatattttaatggaaaaatacagtgcgtgtttgtgg
gggattgactccagatgatagagtagaaatggatctcctaatttttttat
ttatgttttactttatcgagggtctatcaaaaataatttatctatttttt
aaatagagataaagtctgacatactcttttacttgtatttatatgtcat
gattttgattaggagtttggattttctctacgttcaaatacaaattaaac
tataatgagttatttccctaaatttggagaaattatcatttggagatga
gtacacgataataatgtcctctaatcaattacatcaaacacaaaaacatt
attagaaattcacaatctacatgtttgtctaattaatcacatcttcatag        3500
ttgataagtagtacttatcatactttgtagtttatgatttcgaataactt
gacatatgattaattttgtaatactacattactgtttatcaaacttgttt
ttcgaattcatttctagtagtgtgtggcatgacttggacaagagaaatac
aaatattttgaatttattcctactatacattttatttattttaatctat
atataaaagaatatcgtacatatttattaatataaaattttgatatttac
tttttattatagaatttgatatccagtcaaaccgccacataaattgagcc
aatatgtaaatagaaaatgttgacaaaagaaatggatttattggaagaca
aactgacatagggtccaactgaaaagagttaaattgtcggacgactttat
aatattttagtcaaccccacccaaagccttttaaacttagataaatccaa
aagataataattttgattgatattttataatgtatcttttatcatattg        4000
acatgtagaaaaattataatttataatatttttatatagttttaaata
tttaaattttttatttaaaatattaaatgaatatattttaactttagtta
atcaatgacttttaaaaaacgtaatatgacaattaaatgaatagaaaaaa
tatcgattaataagacttttgagatgaaaatattgtctcatgtgaacgat
gctaacgatgtctccaacatggattttgcttccttggctttatttcatga
tttaatatttatattgaaatgactaaggtaagtaaaaaacaaatttcat
attaaagttttgtttgagttgaattcaagttttgattattttctattag
aaatcagatct
```

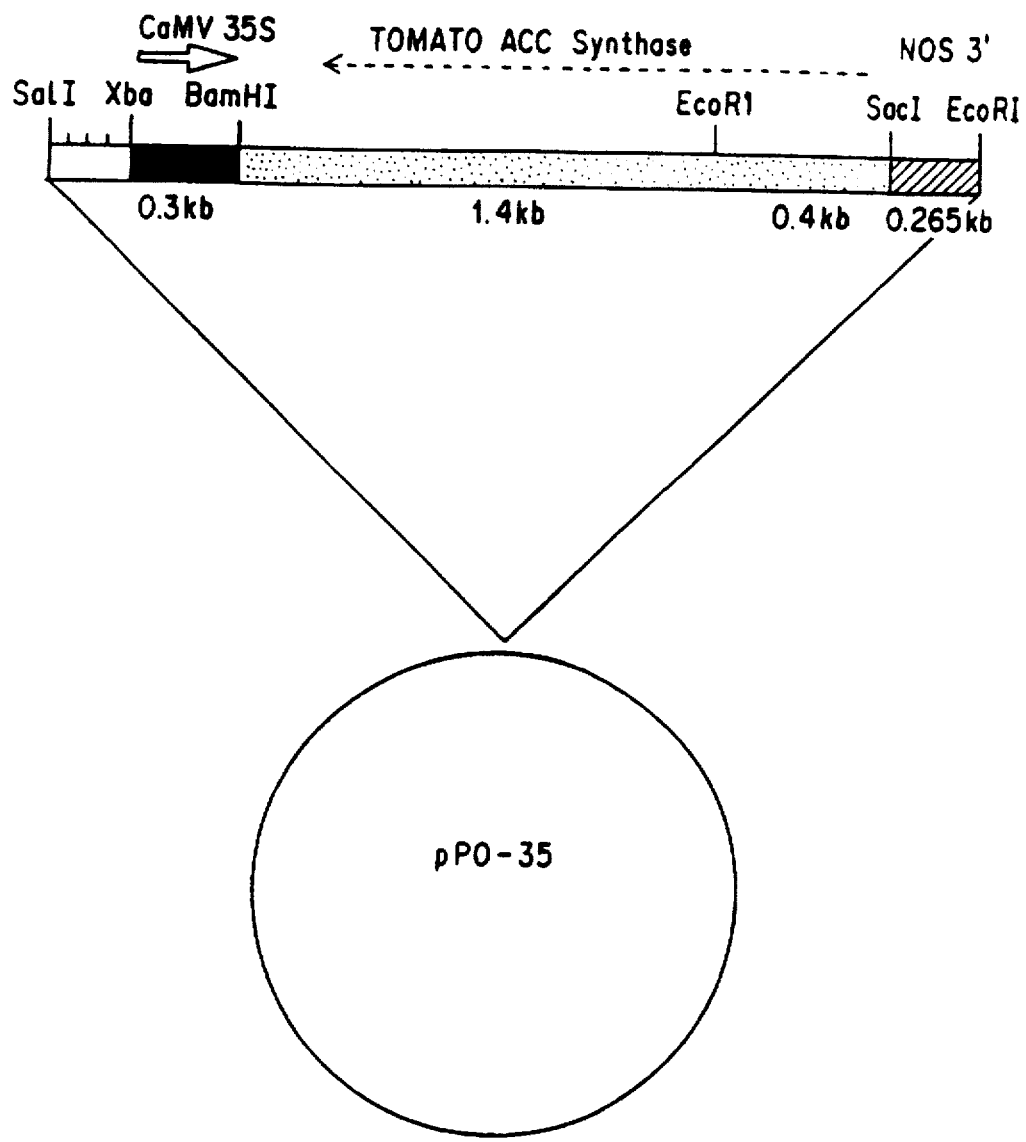
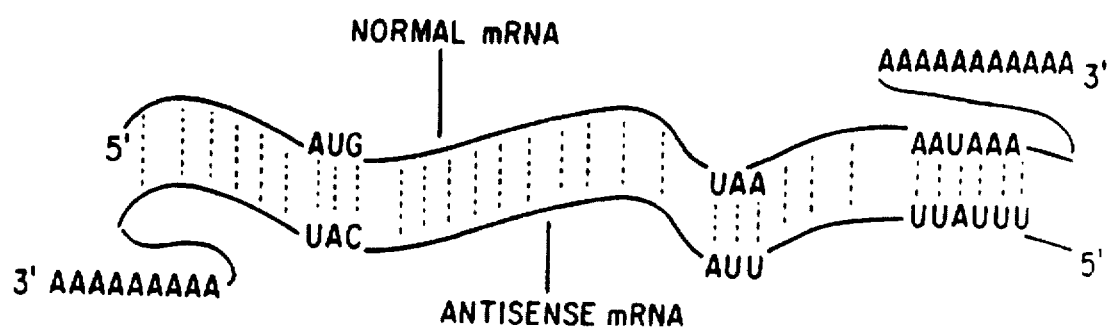
FIG. 14

CONTROL OF FRUIT RIPENING THROUGH GENETIC CONTROL OF ACC SYNTHASE SYNTHESIS

This application is a division of application Ser. No. 08/378,313, filed Jan. 25, 1995, which is a continuation of application Ser. No. 07/862,493, filed Apr. 2, 1992, now abandoned, which is a continuation-in-part of Ser. No. 07/579,896, filed Sep. 10, 1990, now abandoned.

FIELD OF THE INVENTION

The invention relates to the use of genetic materials related to the plant enzyme ACC synthase to control plant development, and in particular, senescence and ripening of fruit. ACC synthase is essential for the production of ethylene in higher plants; ethylene is a determinant of fruit ripening.

BACKGROUND ART

The enzyme ACC synthase is essential to the production of ethylene in higher plants. It is well known that ethylene is related to various events in plant growth and development including fruit ripening seed germination, abscission, and leaf and flower senescence. Ethylene production is strictly regulated by the plant and is induced by a variety of external factors, including the application of auxins, wounding, anaerobic conditions, viral infection, elicitor treatment, chilling, drought, and ions such as cadmium and lithium ions. A review of ethylene production and effects in plants my be found, for example, in Abeles, F. B., "Ethylene in Plant Biology" (1983) Academic Press, New York.

It is also known that the synthesis of ethylene in higher plants includes a rate limiting step which is the conversion of S-adenosyl methionine (AdoMet) to 1-aminocyclopropane-1-carboxylic acid (ACC). This conversion is catalyzed by the enzyme ACC synthase (EC4.4.1.14). This enzyme has been partially purified from several sources by Nakajima, N., et al., *Plant Cell Physiol* (1986) 27:969–980; Mehta, A. M., et al., *Proc Natl Acad Sci USA* (1988) 85:8810–8814; Nakajima, N., et al., *Plant Cell Physiol* (1988) 29:989–990; Tsai, D. S., et al., *Arch Biochem Biophys* (1988) 264:632–640; Bleecker, A. B., et al., *Proc Natl Acad Sci USA* (1986) 83:7755–7759; Privale, L. S., et al., *Arch Biochem Biophys* (1987) 253:333–340; Sato, S., et al., *Plant Physiol* (1988) 88:109–114; Van Der Straeten, D., et al., *Eur J Biochem* (1989) 182:639–647.

As the level of ACC synthase controls the production of ethylene, control of the level of this enzyme permits control of ethylene levels and thus regulation of the plant growth and development aspects that are controlled by ethylene. The availability of the relevant ACC synthase expression system and coding sequences permits control of ACC synthase expression and activity, as provided by the invention herein.

In an abstract published in connection with the UCLA Symposia on Molecular and Cellular Biology, held Mar. 27–Apr. 7, 1989, as published in *J Cell Biochem* (1989) Supp. 13D, page 241, Theologis, A., et al. disclosed that a cDNA sequence designated pACC1 from Cucurbita (zucchini) fruits had been isolated by screening a cDNA library in λgt11 with antiserum prepared by subtraction purification using proteins obtained from tissues that were induced and uninduced for ACC synthase. The pACC1 clone was reported to hybridize to a 1900 nucleotide mRNA that was induced by auxin and lithium ions. The abstract further reports that using the Cucurbita cDNA as a probe, cDNA and genomic clones encoding tomato ACC synthase were isolated, and that the authenticity of these clones had been confirmed by recovery of enzyme activity after expression in *E. coli*. An expanded version of the work described in this abstract was published by Sato, T. et al., *Proc Natl Acad Sci USA* (1989) 86:6621–6625. However, neither the abstract nor the paper disclosed the details of the purification of the native ACC synthase. An additional abstract further reporting this work and indicating that the ACC synthase in tomatoes was encoded by a single-copy gene was published in connection with the succeeding UCLA Symposium on Molecular and Cellular Biology in *J Cell Biochem* (1990) Supp. 14E, page 358. This symposium was held Mar. 31–Apr. 22, 1990.

Two additional accounts of the recovery of cDNA encoding the ACC synthase of Cucurbita fruit, and further indicating that the Cucurbita genome contains two linked ACC synthase genes which are transcribed in opposing directions were published in *Horticultural Biotechnol* (1990) Wiley-Liss, Inc., pp. 237–246 and in *Plant Gene Transfer* (1990) Alan R. Liss, Inc., pp. 289–299. A further summary was presented in an abstract published in connection with Plant Molecular Biology Meeting conducted by the NATO Advanced Study institute held in Bavaria on May 14–23, 1990 and at the Third International Symposium of the Society of Chinese Bioscientists in America, held Jun. 24–30, 1990. None of these publications disclosed the nucleotide sequences of either the coding or control regions for any of the ACC synthase genes.

Sato, T. et al., *J Biol Chem* (1991) 266:3752–3759 described the isolation, properties, and expression in *E. coli* of the 50 kd ACC synthase of Cucurbita as encoded by the cDNA prepared from messenger RNA present in fruits induced with auxin and lithium ion. The preparation of this cDNA and the complete deduced amino acid sequence thereof are described hereinbelow in Example 1 and FIG. 1.

Van der Straeten, D., et al. reported the cloning and sequences of cDNAs purportedly encoding ACC synthase from tomato (*Proc Natl Acad Sci USA* (1990) 87:4859–4863). Although the cDNA, which corresponded to an open reading frame of approximately 55 kd, produced a 55 kd peptide in *E. coli*, the authors were unable to show ACC synthase activity in the extracts of *E. coli* producing this protein. Comparison with the sequences described in the present invention shows that two amino acid residues that are invariant among the polypeptides found herein are miscoded in the vector reported by van der Straeten; specifically, Leu322 was changed to Pro322 and Pro399 was changed to Leu399. It is believed that these changes in the highly conserved regions lead to inactivated forms of this protein.

DISCLOSURE OF THE INVENTION

The invention provides recombinant materials and techniques which permit control of the level of ACC synthase in plants and portions thereof. The invention herein demonstrates that although ACC synthases in zucchini and tomato are encoded by a multigene family, only certain members of this family are expressed to produce the ACC synthase associated with ripening fruit. Thus, it is the expression of these specific members of the multigene family which must be controlled in order to influence the level of production of the relevant ACC synthase. Further, the provision of the sequences encoding ACC synthases of a large family of these enzymes permits designation of conserved regions so that primers suitable for polymerase chain reaction-based recovery of the corresponding genomic regions in other plants can be accomplished. This permits the control of plant development and activity in a wide variety of plant materials of commercial interest.

Accordingly, in one aspect, the invention is directed to methods to control ACC synthase production using the expression control and coding sequences for the relevant ACC synthase in either a sense or an antisense construct or by replacing the ACC synthase gene by a mutated form thereof.

The invention further includes materials useful in producing transgenic plants which are overproducers of or are deficient in ACC synthase and to the plants thus obtained. In another aspect, the invention is directed to methods to retrieve ACC synthase genes, including their control sequences, from higher plants using primers representing conserved regions of the ACC synthase genes in tomato and Cucurbita. The invention is also directed to primers useful in this technique. Finally, the invention is directed to recombinant materials related to ACC synthase and to isolated and purified ACC synthase per se.

BRIEF DESCRIPTION OF THE DRAWINGS

FIG. 1B (SEQ ID NO: 18 and SEQ ID NO:19) shows the nucleotide and deduced amino acid sequence of one of these clones, pACC1.

FIG. 2 shows a restriction map of genomic clones obtained by hybridization to the cDNA encoding zucchini ACC synthase. FIG. 2B shows a restriction map of the sequences on the genome; FIG. 2C shows the functional portions of the two zucchini ACC synthase genes CP-ACC 1A and CP-ACC 1B.

FIG. 3(A–F) (SEQ ID NO:20 and SEQ ID NO:21) shows the complete nucleotide sequence and deduced amino acid sequence of the genomic clone representing CP-ACC 1A. Both control regions and coding regions are shown.

FIG. 4(A–E) (SEQ ID NO:22 and SEQ ID NO:23) shows the complete nucleotide sequence and deduced amino acid sequence of the genomic clone representing CP-ACC 1B. Both control regions and coding regions are shown.

FIG. 5(A–C) (SEQ ID NO:24 and SEQ ID NO:25) shows the nucleotide and deduced amino acid sequence of a cDNA encoding the tomato ACC synthase.

FIG. 9(A–E) (SEQ ID NO:26 and SEQ ID NO:27) shows the complete genomic sequence and deduced amino acid sequence of LE-ACC 2, including the control sequences.

FIG. 10 shows a comparison of the deduced amino acid sequence from the two genomic zucchini clones and the four genomic tomato clones for ACC synthase (SEQ ID NO:28 through SEQ ID NO:34).

FIG. 14 shows the construction of an expression vector for the tomato ACC-synthase gene oriented in the antisense direction.

MODES OF CARRYING OUT THE INVENTION

Figure 1A:
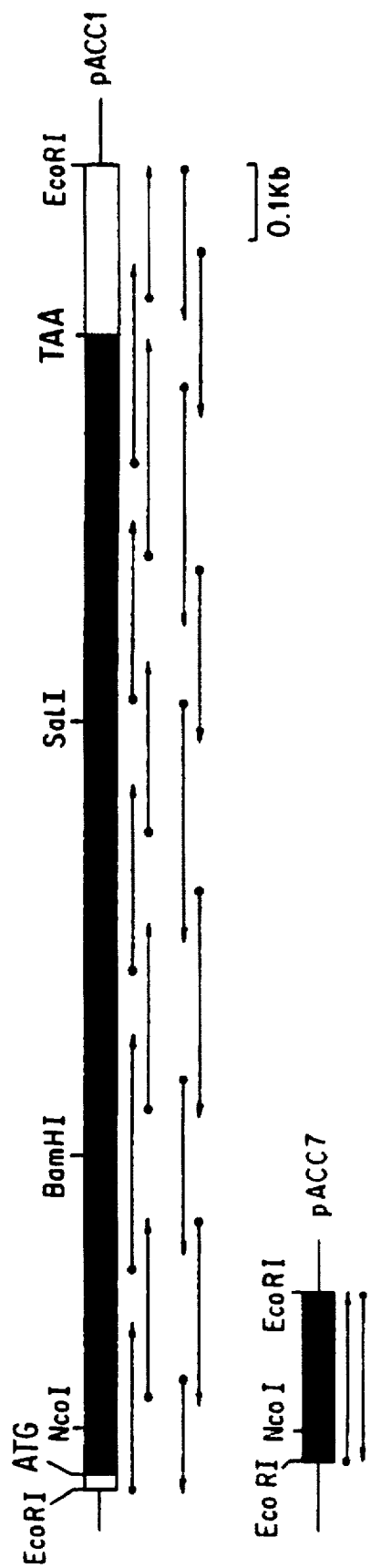
FIG. 1A shows a restriction map of two clones encoding the zucchini ACC synthase enzyme.

As shown herein, the genetic control of ACC synthase activity in higher plants is complex. The Cucurbita system contains at least two genomic regions encoding ACC synthases, ACC-1A and ACC-1B. The situation in tomato is even more complex wherein five independent ACC synthase regions are found in the genome, only one or two of which appear to be relevant to ripening of the fruit. While the coding regions of these various ACC synthases are highly homologous, the control regions responsible for their expression evidently are not.

The ripening of fruit is known to involve a complex series of reactions and interactions that is incompletely understood. A number of enzymes are known to be involved in the ripening process, including ACC synthase, the protein encoded by the TOM13 gene, and polygalactouronase. It is not clear to what extent the control of only one or a few of these enzymatic and other interactions would be successful in controlling ripening. Thus, it is not expected that the control of ACC synthase production, taken alone, would be adequate to control the ripening of fruit. However, as illustrated by the invention below, this is in fact the case.

While the various ACC synthases are generally active in a variety of plant tissues, the DNAs are not completely homologous, and therefore the use of the genetic materials for control of synthesis, for example, using an antisense strategy, does not translate across species.

The availability of a multiplicity of ACC synthases as provided by the invention permits comparison of their sequences to find conserved regions. These conserved regions are useful in the design of primers to mediate the recovery of ACC synthases in higher plants using the polymerase chain reaction.

Definitions and Abbreviations

The following abbreviations are used in the specification: ACC=1-aminocyclopropane-1-carboxylic acid; AdoMet= S-adenosyl methionine; CaMV=cauliflower mosaic virus; IPTG=the inducer isophosphothiogalactose; MTA=mehyl thioadenosine; CP=*Cucurbita pepo*; and LE=*Lycopersicon esculentum*.

As used herein, "recombinant" refers to a nucleic acid sequence which has been obtained by manipulation of genetic material using restriction enzymes, ligases, and similar recombinant techniques as described by, for example, Maniatis et al. "Recombinant," as used in the present application, does not refer to naturally-occurring genetic recombinations.

As defined herein, "ACC synthase" includes all enzymes which are capable of catalyzing the conversion of AdoMet to ACC and methyl thioadenosine (MTA). The amino acid sequence of the synthase may or may not be identical with the amino acid sequence which occurs natively in higher plants. An example of such native sequence is shown in FIG. 1 which occurs in the zucchini fruit (*Cucurbita pepo*). Naturally occurring allelic variants undoubtedly occur as well. Similar proteins are present in a wide variety of higher plants. In addition, artificially induced mutations are also included so long as they do not destroy activity. In general, conservative amino acid substitutions can be made for most of the amino acids in the primary structure as shown without affecting destruction of activity. Thus, the definition of ACC synthase used herein includes these variants which are derived by direct or indirect manipulation of the disclosed sequences.

It is also understood that the primary structure may be altered by post-translational processing or by subsequent chemical manipulation to result in a derivatized protein which contains, for example, glycosylation substituents, oxidized forms of, for example, cysteine or proline, conjugation to additional moieties, such as carriers, solid supports, and the like. These alterations do not remove the protein from the definition of ACC synthase so long as its capacity to convert AdoMet to ACC and MTA is maintained.

Thus, the identity of an enzyme as "ACC synthase" can be confirmed by its ability to effect the production of ethylene in an assay performed as follows: the enzyme to be tested is incubated with 200 µM AdoMet, 10 µM pyridoxal phosphate, 40 µg BSA in 200 mM Hepes buffer, pH 8.5 in a total volume of 600 µl at 30° C. for 30 minutes, and the amount of ACC formed is assayed by conversion to ethylene using hypochlorite as described, for example, by Lizada, C. C., et al., *Anal Biochem* (1979) 100:140–145. While alternative forms of assessment of ACC synthase can be devised, and variations on the above protocol are certainly permissible, the foregoing provides a definite criterion for the presence of ACC synthase activity and classification of a test protein as ACC synthase.

Figure 10A:
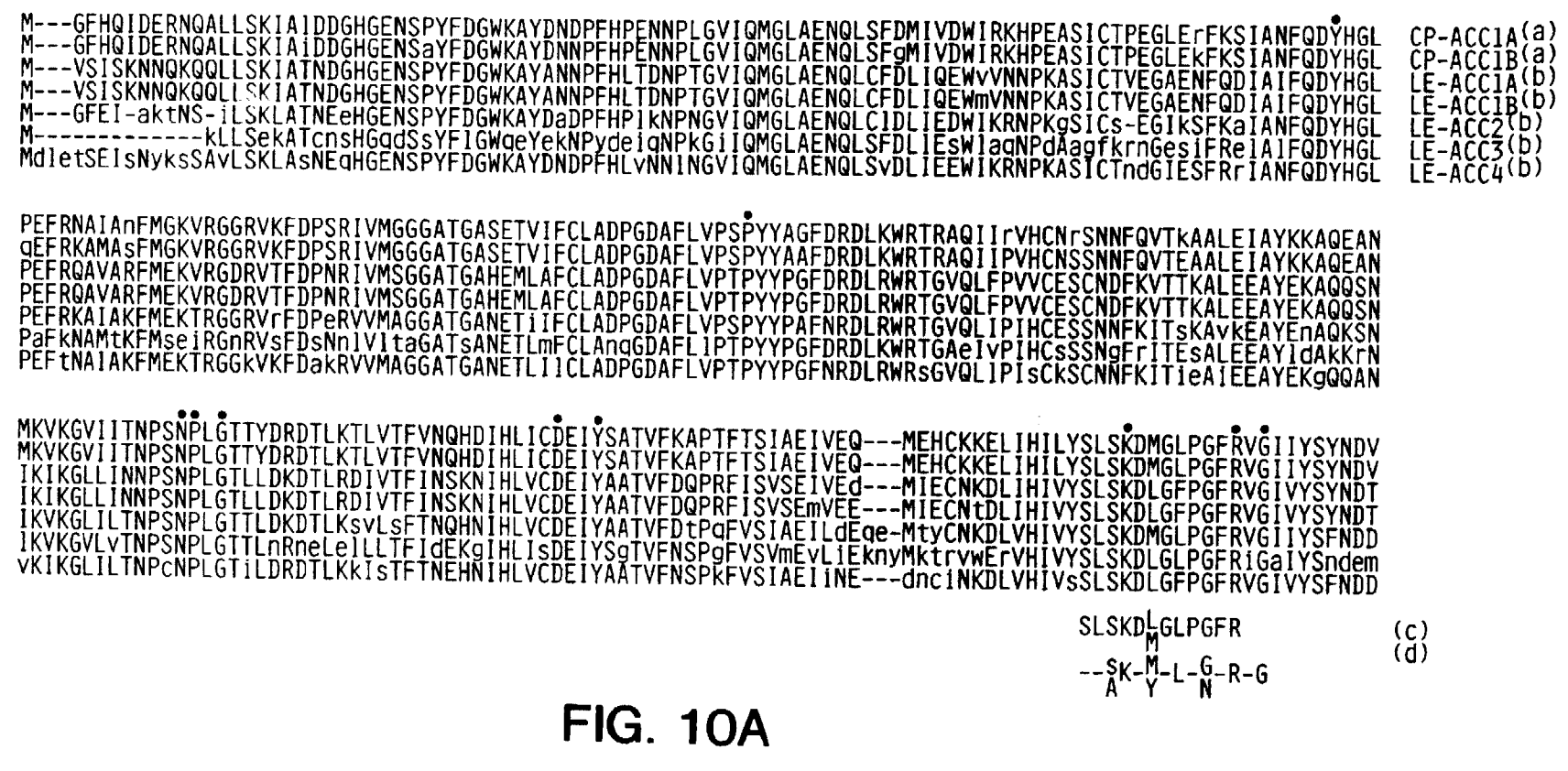
Figure 10B:
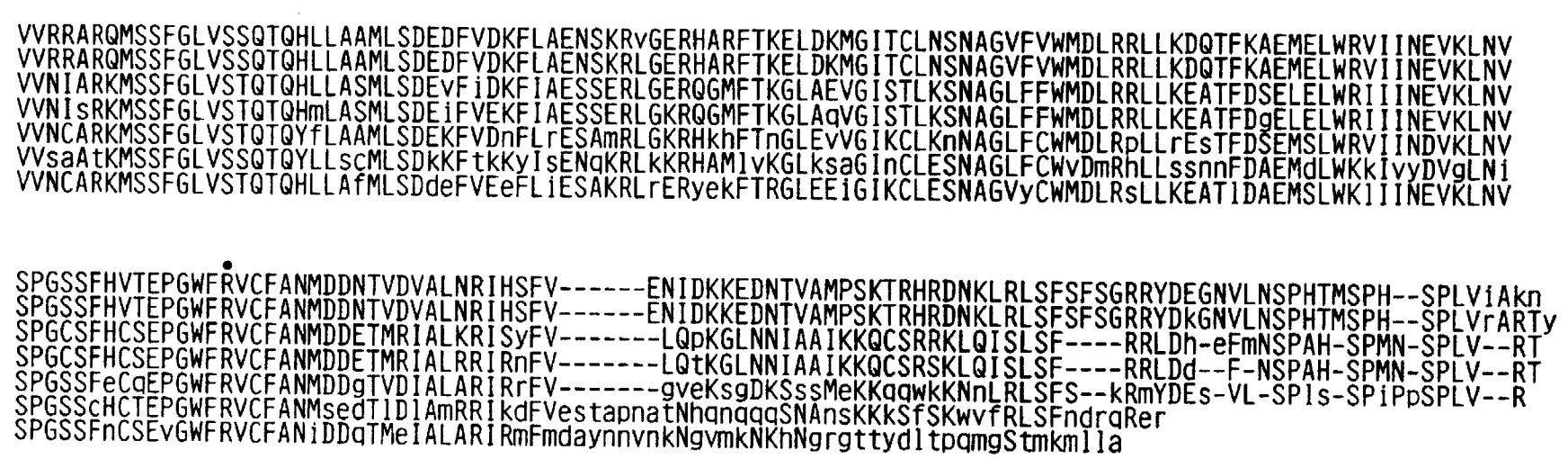

The amino acid sequences for several ACC synthases in tomato and zucchini are shown in FIG. 10 as published in Rottmann, W. H., et al., *J Mol Biol* (1991) 22.2:937–961. Preferred forms of the ACC synthases of the invention include those thus illustrated herein, and those derivable therefrom by systematic mutation of the genes. Such systematic mutation may be desirable to enhance the ACC synthase properties of the enzyme, to enhance the characteristics of the enzyme which are ancillary to its activity, such as stability, or shelf life, or may be desirable to provide inactive forms useful in the control of ACC activity in vivo, as further described below.

As described above, "ACC synthase" refers to a protein having the activity assessed by the assay set forth above; a "mutated ACC synthase" refers to a protein which does not necessarily have this activity, but which is derived by mutation of a DNA encoding an ACC synthase. By "derived from mutation" is meant both direct physical derivation from a DNA encoding the starting material ACC synthase using, for example, site specific mutagenesis or indirect derivation by synthesis of DNA having a sequence related to, but deliberately different from, that of the ACC synthase. As means for constructing oligonucleotides of the required length are available, such DNAs can be constructed wholly or partially from their individual constituent nucleotides.

As used herein, "higher plant" refers to those plants whose development and activity are controlled by ethylene. These include all common agricultural plants and various flowering species.

Derivation of Primers

FIG. 10 hereinbelow provides the comparative amino acid sequences of five ACC synthases encoded by the tomato genome and two encoded by the zucchini genome. The amino acid sequences are shown in a single-letter code in the order: CP-ACC 1A, CP-ACC 1B, LE-ACC 1A, LE-ACC 1B, LE-ACC2, LE-ACC3 and LE-ACC4. Completely conserved residues are indicated by shaded boxes; partially conserved residues are shown in capital letters; and residues not found in more than 1 polypeptide are shown as small letters. Gaps have been introduced to maximize matching. The sources of the sequences are: (a) zucchini (*Cucurbita pepo*); (b) tomato (*Lycopersicon esculentum*); (c) AdoMet- and pyridoxal phosphate-binding site in tomato ACC synthase, *Proc Natl Acad Sci USA* (1990) 87:7930–7934; and (d) consensus of the pyridoxal phosphate-binding site in aminotransferases (Mehta et al., *Eur J Biochem* (1989) 186:249–253). The filled circles indicate the 11 invariant amino acids conserved among ACC synthase and various aminotransferases.

As shown in FIG. 10, there are a number of conserved sequences in these proteins. Among these sequences are:

QMGLAENQ (L);

FQDYHG (L);

FMEK (V/T);

(K/A) A (L/V) E (E/D)AY;

GDAFL (V/I) P;

NPLGT;

SLSKD;

PGFR (V/I) G;

RVCFANMD;

MSSFGLVS; and

GWFRVCFAN (M/I).

These conserved amino acid sequences can be used to design degenerate consensus primers for amplification of the relevant genes in other higher plants. It has been shown by the inventors herein that these same regions are conserved in rice and in arabidopsis. Methods to design such degenerate primers using information related to codon preference and the like are well known in the art. The primers can then be used to conduct amplification by the polymerase chain reaction of the desired regions of the gene or cDNA extracted from other higher plants in order to isolate relevant ACC synthase encoding DNA.

Particularly useful are combinations of primers wherein the 5'→5' primer encodes MGLAENQ (SEQ ID NO:12) and the 3'→5' encodes FQDYRGL (SEQ ID NO:2); or wherein the 5'→3' primer encodes FQDYHG positions 1–6 of (SEQ ID NO:2) and the 3'→5' primer encodes FMER (V/T) R (SEQ ID NO:13); or wherein the 5'→3' primer encodes KA (L/V) EEAY (SEQ ID NO:14) and the 3'→5' primer encodes FPGFRVG (SEQ ID NO:15); or wherein the 5'→3' primer encodes KALEEAY (SEQ ID NO:16) and the 3'→5' primer encodes RVCFANMD (SEQ ID NO:9). In the foregoing, the amino acid sequences encoded are given in the N→C direction, regardless of whether the primer complements the 5'→3' region of the coding strand or is the complement in the corresponding 3'→5' region of the noncoding strand. Reference can be had to the gene sequences shown, for example, in FIGS. 3–5 and 9, which provide the complete coding sequence for various ACC genes to select the appropriate codons for the construction of primers.

Expression Systems

The coding sequence for ACC synthase and the DNA which represents the reverse transcript of the mRNA that is subsequently translated into ACC synthase can be included in expression systems suitable for higher plants. In at least three such expression systems, the changes in fruit associated with ethylene production can be retarded.

In one approach, a mutated form of the ACC synthase is supplied in an expression system to provide an alternative inactive monomer for coupling to the natively produced ACC synthase to effect dimer formation. As the ACC synthase is active as a dimer, inclusion of a mutated, inactivated form in the dimer destroys the effectiveness of the protein.

In a second approach, transformation of plants with a recombinant expression system for the relevant ACC synthase or a truncated form thereof may result, through an unknown mechanism, in suppression of the native production of ACC synthase, and may thus provide a means to inhibit, for example, the ripening of fruit in such plants. It has been shown previously that attempts to overexpress chalcone synthase in pigmented petunia petals by introducing the recombinant gene resulted in a suppression of the homologous native genes, thus resulting in a block in anthocyanine biosynthesis (Napoli, C., et al., *The Plant Cell* (1990) 2:279–289). These results were confirmed and extended to transformation with genes encoding dihydroflavonol-4-reductase genes in petunias by van der Krol, A. R., et al., *The Plant Cell* (1990) 2:291–299. It has also been found that transformation of a partial nopaline synthase gene into tobacco suppresses the expression of the endogenous corresponding gene, as reported by Goring, D. R., et al., *Proc Natl Acad Sci USA* (1991) 88:1770–1774. Similar results were described for the expression of a truncated tomato polygalactonuronase gene in transgenic tomatoes by Smith, C. J. S., et al., *Mol Gen Genet* (1990) 224:477–481. Elkind, Y., et al., *Proc Natl Acad Sci USA* (1990) 87:9057–9061, reported similar results in tobacco containing a heterologous phenylalanine ammonia-lyase gene. In general, it appears that supplying a truncated form of the relevant gene in the "sense" orientation suppresses the endogenous expression of the native gene, thus lowering the level of the gene product, despite the presence of the additional transformation system.

Alternatively, a DNA which is transcribed into the complement of mRNA that is translated by the host plant into ACC synthase can be provided to effect an antisense retardation of expression of the native gene. The following discussion describes control sequences and procedures which are useful in effecting expression in higher plants.

Especially useful in connection with the ACC synthase genes of the present invention are expression systems which are operable in plants. These include systems which are under control of a tissue-specific promoter, as well as those which involve promoters that are operable in all plant tissues.

Transcription initiation regions, for example, include the various opine initiation regions, such as octopine, mannopine, nopaline and the like. Plant viral promoters can also be used, such as the cauliflower mosaic virus 35S promoter. In addition, plant promoters such as ribulose-1,3-diphosphate carboxylase, fruit-specific promoters, heat shock promoters, seed-specific promoters, etc. can also be used.

The cauliflower mosaic virus (CaMV) 35S promoter has been shown to be highly active in many plant organs and during many stages of development when integrated into the genome of transgenic plants including tobacco and petunia, and has been shown to confer expression in protoplasts of both dicots and monocots.

The CaMV 35S promoter has been demonstrated to be active in at least the following monocot and dicot plants with edible parts: blackberry, *Rubus*; blackberry/raspberry hybrid, *Rubus*, and red raspberry; carrot, *Daucus carota*; maize; potato, *Solanum tuberosum*; rice, *Oryza sativa*; strawberry, *Fragaria x ananassa*; and tomato, *Lycopersicon esculentum*.

The nopaline synthase (Nos) promoter has been shown to be active in at least the following monocot and dicot plants with edible parts: apple, *Malus pumila*; cauliflower, *Brassica oleracea*; celery, *Apium graveolens*; cucumber, *Cucumis sativus*; eggplant, *Solanum melongena*; lettuce, *Lactuca sativa*; potato, *Solanum tuberosum*; rye, *Secale cereale*; strawberry, *Fragaria x ananassa*; tomato, *Lycopersicon esculentum*; and walnut, *Juglans regia*.

Organ-specific promoters are also well known. For example, the E8 promoter is only transcriptionally activated during tomato fruit ripening, and can be used to target gene expression in ripening tomato fruit (Deikman and Fischer, *EMBO J* (1988) 7:3315; Giovannoni et al., *The Plant Cell* (1989) 1:53). The activity of the E8 promoter is not limited to tomato fruit, but is thought to be compatible with any system wherein ethylene activates biological processes.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans R Soc London* (1986) B314:343.

These mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

A somewhat more sophisticated procedure was described in *Molecular Biology of the Cell*, Second Edition (1989) pages 261–262, edited by Alberts et al., Garland Publishing Incorporated, New York. In this procedure, mRNAs enriched for organ-specific nucleic acid sequences were used to construct the cDNA library. This method was also applied to tomato by Lincoln et al., *Proc Natl Acad Sci* (1987) 84:2793, and resulted in the production of an E8 cDNA clone.

The gene that encodes the organ-specific mRNA is then isolated by constructing a library of DNA genomic sequences from the plant. The genome library is screened with the organ-specific cDNA clone, and the sequence is determined. The promoter is then isolated. These procedures are now considered to be routine and are described in detail in Sambrook et al., *Molecular Cloning: A Laboratory Manual*, Second Edition (1989) Cold Spring Harbor Laboratory Press, Cold Spring Harbor.

Either a constitutive promoter or a desired organ-specific promoter is then ligated to the gene encoding ACC synthase or a mutated form thereof using standard techniques now common in the art. The expression system may be further optimized by employing supplemental elements such as transcription terminators and/or enhancer elements.

Thus, for expression in plants, the recombinant expression cassette will contain in addition to the ACC synthase-encoding sequence, a plant promoter region, a transcription initiation site (if the coding sequence to be transcribed lacks one), and a transcription termination sequence. Unique restriction enzyme sites at the 5' and 3' ends of the cassette are typically included to allow for easy insertion into a pre-existing vector.

Sequences controlling eucaryotic gene expression have been extensively studied. Promoter sequence elements include the TATA box consensus sequence (TATAAT) (SEQ ID NO:17), which is usually 20 to 30 base pairs (bp) upstream of the transcription start site. In most instances the TATA box is required for accurate transcription initiation. By convention, the start site is called +1. Sequences extending in the 5' (upstream) direction are given negative numbers and sequences extending in the 3' (downstream) direction are given positive numbers.

In plants, further upstream from the TATA box, at positions −80 to −100, there is typically a promoter element with a series of adenines surrounding the trinucleotide G (or T) NG (Messing, j. et al., in *Genetic Engineering in Plants*, Kosage, Meredith and Hollaender, eds. (1983) pp. 221-227). Other sequences conferring tissue specificity, response to environmental signals, or maximum efficiency of transcription may also be found in the promoter region. Such sequences are often found within 400 bp of the transcription initiation site, but may extend as far as 2000 bp or more.

In the construction of heterologous promoter/structural gene combinations, the promoter is preferably positioned about the same distance from the heterologous transcription start site as it is from the transcription start site in its natural setting. As is known in the art, however, some variation in this distance can be accommodated without loss of promoter function.

As stated above, any of a number of promoters which direct transcription in plant cells is suitable. The promoter can be either constitutive or inducible. Promoters of bacterial origin include the octopine synthase promoter, the nopaline synthase promoter and other promoters derived from native Ti plasmids (Herrera-Estrella et al., *Nature* (1983) 303:209-213). Viral promoters include the 35S and 19S RNA promoters of cauliflower mosaic virus (O'Dell et al., *Nature* (1985) 313:810-812). Plant promoters include the ribulose-1,3-disphosphate carboxylase small subunit promoter and the phaseolin promoter. The promoter sequence from the E8 gene and other genes in which expression is induced by ethylene may also be used. The isolation and sequence of the E8 promoter is described in detail in Deikman and Fischer, *EMBO J* (1988) 7:3315-3320 which is incorporated herein by reference.

In addition to a promoter sequence, the expression cassette should also contain a transcription termination region downstream of the structural gene to provide for efficient termination. The termination region may be obtained from the same gene as the promoter sequence or may be obtained from different genes.

If the mRNA encoded by the structural gene is to be efficiently processed, DNA sequences which direct polyadenylation of the RNA are also commonly added to the vector construct (Alber and Kawasaki, *Mol and Appl Genet*, (1982) 1:419-434). Polyadenylation is of importance for expression of the ACC synthase-encoding RNA in plant cells. Polyadenylation sequences include, but are not limited to the Agrobacterium octopine synthase signal (Gielen et al., *EMBO J*, (1984) 3:835-846) or the nopaline synthase signal (Depicker et al., *Mol and Appl Genet* (1982) 1:561-573).

For in situ production of the antisense mRNA of ACC synthase, those regions of the ACC synthase gene which are transcribed into ACC synthase mRNA, including the untranslated regions thereof, are inserted into the expression vector under control of the promoter system in a reverse orientation. The resulting transcribed mRNA is then complementary to that normally produced by the plant. The presence of the antisense mRNA, as shown hereinbelow, effectively retards the activity of the native ACC synthase and, thus, the ripening of the fruit.

The resulting expression system or cassette is ligated into or otherwise constructed to be included in a recombinant vector which is appropriate for higher plant transformation. The vector will also typically contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range procaryotic origin of replication is included. A selectable marker for bacteria should also be included to allow selection of bacterial cells bearing the desired construct. Suitable procaryotic selectable markers also include resistance to antibiotics such as kanamycin or tetracycline.

Other DNA sequences encoding additional functions may also be present in the vector, as is known in the art. For instance, in the case of Agrobacterium transformations, T-DNA sequences will also be included for subsequent transfer to plant chromosomes.

In addition, vectors can also be constructed that contain in-frame ligations between the sequence encoding the ACC synthase protein and sequences encoding other molecules of interest resulting in fusion proteins, by techniques well known in the art.

When an appropriate vector is obtained, transgenic plants are prepared which contain the desired expression system. A number of techniques are available for transformation of plants or plant cells. All types of plants are appropriate subjects for "direct" transformation; in general, only dicots can be transformed using Agrobacterium-mediated infection.

In one form of direct transformation, the vector is microinjected directly into plant cells by use of micropipettes to mechanically transfer the recombinant DNA (Crossway, *Mol Gen Genetics* (1985) 202:179-185). In another form, the genetic material is transferred into the plant cell using polyethylene glycol (Krens, et al., *Nature* (1982) 296:72-74), or high velocity ballistic penetration by small particles with the nucleic acid either within the matrix of small beads or particles, or on the surface, is used (Klein, et al., *Nature* (1987) 327:70-73). In still another method protoplasts are fused with other entities which contain the DNA whose introduction is desired. These entities are minicells, cells, lysosomes or other fusible lipid-surfaced bodies (Fraley, et al., *Proc Natl Acad Sci USA* (1982) 79:1859-1863).

DNA may also be introduced into the plant cells by electroporation (Fromm et al., *Proc Natl Acad Sci USA* (1985) 82:5824). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another approach for DNA introduction into plant cells is by electroporation of pollen grains and subsequent in vivo fertilization, ultimately yielding transformed seed. This technique is described by Matthews et al., *Sex Plant Reprod* (1990) 3:147–151; and by Abdul-Baki et al., *Plant Science* (1990) 70:181–190.

For transformation mediated by bacterial infection, a plant cell is infected with *Agrobacterium tumefaciens* or *A. rhizogenes* previously transformed with the DNA to be introduced. Agrobacterium is a representative genus of the gram-negative family Rhizobiaceae. Its species are responsible for crown 9all (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome (Schell, J., *Science* (1987) 237:1176–1183). Ti and Ri plasmids contain two regions essential for the production of transformed cells. One of these, named transferred DNA (T-DNA), is transferred to plant nuclei and induces tumor or root formation. The other, termed the virulence (vir) region, is essential for the transfer of the T-DNA but is not itself transferred. The T-DNA will be transferred into a plant cell even if the vir region is on a different plasmid (Hoekema, et al., *Nature* (1983) 303:179–189). The transferred DNA region can be increased in size by the insertion of heterologous DNA without its ability to be transferred being affected. Thus a modified Ti or Ri plasmid, in which the disease-causing genes have been deleted, can be used as a vector for the transfer of the gene constructs of this invention into an appropriate plant cell.

Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to "shuttle vectors," (Ruvkum and Ausubel, *Nature* (1981) 298:85–88), promoters (Lawton et al., *Plant Mol Biol* (1987) 9:315–324) and structural genes for antibiotic resistance as a selection factor (Fraley et al., *Proc Natl Acad Sci* (1983) 80:4803–4807).

There are two classes of recombinant Ti and Ri plasmid vector systems now in use. In one class, called "cointegrate," the shuttle vector containing the gene of interest is inserted by genetic recombination into a non-oncogenic Ti plasmid that contains both the cis-acting and trans-acting elements required for plant transformation as, for example, in the pMLJ1 shuttle vector of DeBlock et al., *EMBO J* (1984) 3:1681–1689 and the non-oncogenic Ti plasmid pGV3850 described by Zambryski et al., *EMBO J* (1983) 2:2143–2150. In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* (1984) 12:8711–8721 and the non-oncogenic Ti plasmid PAL4404 described by Hoekema, et al., *Nature* (1983) 303:179–180. Some of these vectors are commercially available.

There are two common ways to transform plant cells with Agrobacterium: co-cultivation of Agrobacterium with cultured isolated protoplasts, or transformation of intact cells or tissues with Agrobacterium. The first requires an established culture system that allows for culturing protoplasts and subsequent plant regeneration from cultured protoplasts. The second method requires (a) that the intact plant tissues, such as cotyledons, can be transformed by Agrobacterium and (b) that the transformed cells or tissues can be induced to regenerate into whole plants.

Most dicot species can be transformed by Agrobacterium as all species which are a natural plant host for Agrobacterium are transformable in vitro. Monocotyledonous plants, and in particular, cereals, are not natural hosts to Agrobacterium. Attempts to transform them using Agrobacterium have been unsuccessful until recently (Hooykas-Van Slogteren et al., *Nature* (1984) 311:763–764). However, there is growing evidence now that certain monocots can be transformed by Agrobacterium. Using novel experimental approaches cereal species such as rye (de la Pena et al., *Nature* (1987) 325:274–276), maize (Rhodes et al., *Science* (1988) 240:204–207), and rice (Shimamoto et al., *Nature* (1989) 338:274–276) may now be transformed.

Identification of transformed cells or plants is generally accomplished by including a selectable marker in the transforming vector, or by obtaining evidence of successful bacterial infection.

Plant cells which have been transformed can also be regenerated using known techniques.

Plant regeneration from cultured protoplasts is described in Evans et al., *Handbook of Plant Cell Cultures*, Vol. 1: (MacMillan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugarcane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants. For example, regeneration has been shown for dicots as follows: apple, *Malus pumila*; blackberry, *Rubus*, Blackberry/raspberry hybrid, *Rubus*, red raspberry, *Rubus*; carrot, *Daucus carota*; cauliflower, *Brassica oleracea*; celery, *Apium graveolens*; cucumber, *Cucumis sativus*; eggplant, *Solanum melongena*; lettuce, *Lactuca sativa*; potato, *Solanum tuberosum*; rape, *Brassica napus*; soybean (wild), *Glycine canescens*; strawberry, *Fragaria x ananassa*; tomato, *Lycopersicon esculentum*; walnut,

*Juglans regia*; melon, *Cucumis melo*; grape, *Vitis vinifera*; mango, *Mangifera indica*;

and for the following monocots: rice, *Oryza sativa*; rye, *Secale cereale*; and maize.

In addition, regeneration of whole plants from cells (not necessarily transformed) has been observed in: apricot, *Prunus armeniaca*; asparagus, *Asparagus officinalis*; banana, hybrid Musa; bean, *Phaseolus vulgaris*; cherry, hybrid Prunus; grape, *Vitis vinifera*; mango, *Mangifera indica*; melon, *Cucumis melo*; ochra, *Abelmoschus esculentus*; onion, hybrid Allium; orange, *Citrus sinensis*; papaya, *Carrica papaya*; peach, *Prunus persica* and plum, *Prunus domestica*; pear, *Pyrus communis*; pineapple, *Ananas comosus*; watermelon, *Citrullus vulgaris*; and wheat, *Triticum aestivum*.

The regenerated plants are transferred to standard soil conditions and cultivated in a conventional manner.

After the expression cassette is stably incorporated into regenerated transgenic plants, it can be transferred to other plants by sexual crossing. Any of a number of standard breeding techniques can be used, depending upon the species to be crossed.

The plants are grown and harvested using conventional procedures.

Antisense Expression

When the ACC synthase coding sequence is placed in correct orientation in the expression systems described above, the ACC synthase protein is produced. However, when the portion of the ACC synthase gene that is transcribed into mRNA is placed in the expression vector in the opposite orientation, the expression vector produces an antisense mRNA which can interfere with the indigenous production of this enzyme. Antisense technology can work at a variety of levels including hybridization to a messenger RNA encoding the ACC synthase, hybridization to single-stranded intermediates in the production of this mRNA, or triplex formation with the DNA duplex which contains the ACC synthase genes. All of these modalities can be employed in effecting antisense control of ACC synthase production.

As shown in Example 7 below, ripening of tomato fruit can be controlled and inhibited by suitable antisense expression of the ACC synthase coding sequence supplied in a vector under the control of the cauliflower 35S promoter. Other properties which are controlled by ethylene can also be influenced by appropriate choice of control systems and/or the particular ACC synthase encoded.

it is further shown below that the active form of ACC synthase in higher plants is a dimer. By supplying a mutated form of ACC synthase monomer, a decoy can be produced to obtain inactive monomer and thereby regulate the levels of ACC synthase in the plant. An additional embodiment of the invention involves the mutated ACC synthase and expression systems therefor.

The following examples are intended to illustrate but not to limit the invention.

EXAMPLE 1

Recovery of Zucchini ACC Synthase cDNA

A cDNA encoding ACC synthase in zucchini fruit was recovered as follows:

Slices 1 mm thick were prepared from zucchini fruits of the species *Cucurbita pepo*. To induce production of ACC synthase, slices were incubated for 18–24 hours in induction medium (50 µM potassium phosphate buffer, pH 6.8; 0.5 mM indole acetic acid (IAA); 0.1 mM benzyl adenine (BA); 50 mM LiCl; 0.6 mM aminooxyacetic acid (AOA); and 50 µg/ml chloramphenicol. (Uninduced tissue was prepared in a similar manner in 50 mM phosphate buffer, pH 6.8.)

Poly($A^+$) RNA (mRNA) was isolated from 18-hr tissue prepared as described above, and in vitro translated in a wheat germ lysate as described by Theologis, A., et al., *J Mol Biol* (1985) 183:53–68, in the presence of labeled methionine (greater than 1,000 Ci/µmol) to verify the presence of ACC synthase encoding mRNA. A cDNA library was prepared in λgt11 as described by Huynh, T. V., et al., in "DNA Cloning Techniques," Glover, E., ed. (1985) IRL Press, Oxford, 1:49–88. The insert sizes were 200–500 bp. The library was screened with purified ACC synthase antiserum prepared as follows:

The antisera were prepared to 1500-fold purified ACC synthase preparations. Purified ACC synthase can be prepared from tissue homogenates sequentially bound to and eluted from Butyl Toyopearl (Toyo Soda Tokyo), SP-Sephadex, and QAE-Sephadex. (Higher purification can be obtained by subsequent chromatography sequentially through columns containing Butyl Toyopearl, Sephacryl S-300, Bio Gel-HT, and finally FPLC mono-Q. The application of all of the foregoing steps results in approximately a 6000-fold purification.) The antibodies are prepared in New Zealand white rabbits by immunization protocols involving four immunizations at three-week intervals with 5000 nmol of ACC synthase activity/hr (specific activity 1500 nmol of ACC/hr/mg protein obtained from the Bio Gel-HT column). Crude antiserum (2 ml) was purified by incubation with 10 ml Sepharose 4B coupled with soluble proteins from intact noninduced Cucurbita fruit. This step removed antibodies immunoreactive with protein other than ACC synthase.)

Sixty-six immunoreactive clones were isolated by screening $1.4 \times 10^5$ λgt11 recombinant clones with the purified antiserum. Upon rescreening, only 30 were, in fact, positive. Southern analysis showed that 19 clones represented the ACC synthase mRNA. One selected clone, pACC1, has an open reading frame encoding a 55.8 kd polypeptide. Another intensely immunoreactive clone, pACC7, was much shorter. FIG. 1A shows a restriction map of pACC1 and pACC7; FIG. 1B shows the complete nucleotide sequence and deduced amino acid sequence for pACC1.

As shown in FIG. 1, pACC7 is identical to a portion of the sequence of pACC1. The open reading frame encodes a protein of 493 amino acids, corresponding to a 55.779 kd polypeptide.

The positive clones from the λgt11 library could also be used to prepare further purified antiserum for immunoblotting as follows:

The positive clones from the expression library were plated on *E. coli* strain Y1090 to obtain $10^5$ plaque-forming units per 90-mm plate. Dry nitrocellulose filters presoaked in 10 mM isopropyl β-D-thiogalacto-pyranoside (IPTG) were laid on the lawn after incubation for two hours at 42° C. and then incubated for an additional four hours at 37° C.

The filters were then soaked for 30 minutes in TBST (50 mM Tris HCl, pH 8.0; 0.14M NaCl; 0.05% Tween 20); 2% milk protein and then tested for ACC synthase expression by treating with 5 ml of diluted (1:500) purified ACC synthase antiserum (see below) per filter for two hours.

After washing five times at 10 minutes each with TBST, bound antibody was eluted by shaking for three minutes at room temperature with 0.2M glycine hydrochloride buffer, pH 2.3, containing 1% milk protein. The antibody solution was neutralized and used for immunoblotting.

EXAMPLE 2

Isolation of Zucchini Genomic Clones Encoding ACC Synthase

Four-day-old etiolated frozen zucchini seedlings were homogenized in 15% sucrose, 50mM Tris-HCl, pH 8.5, 50 mM EDTA-Na₃, 0.25M NaCl. The nuclei were pelleted by centrifugation at 4,000 rpm for 10 min at 4° C. and nuclear DNA was isolated by CsCl ethidium bromide equilibrium density gradient centrifugation. The recovered DNA was partially digested with Sau3A and electrophoretically separated on 0.5% low melting agarose.

DNA corresponding to 20 kb in size was ligated into EcoRI/BamHI cut EMBL 3λ (Frischauf, A. M., et al., *J Mol Biol* (1983) 170:827–842; Raleigh, E. A., et al., *Proc Natl Acad Sci USA* (1986) 83:9070–9074; Maniatis, T., et al., *Molecular Cloning* (1982) Cold Spring Harbor Laboratory, Cold Spring Harbor, N.Y.). The ligation mixture was packaged and the library was screened without amplification by plating on *E. coli* strain K802 and screening with nick translated ACC1 cDNA (the full length zucchini cDNA clone) as described by Benton, D., et al, *Science* (1977) 196:179–183. The isolated genomic sequences were mapped with restriction endonucleases and the appropriate DNA fragments which hybridize to the ACC1 cDNA were subcloned into the pUC18 and pUC19 plasmids.

Figure 2A:
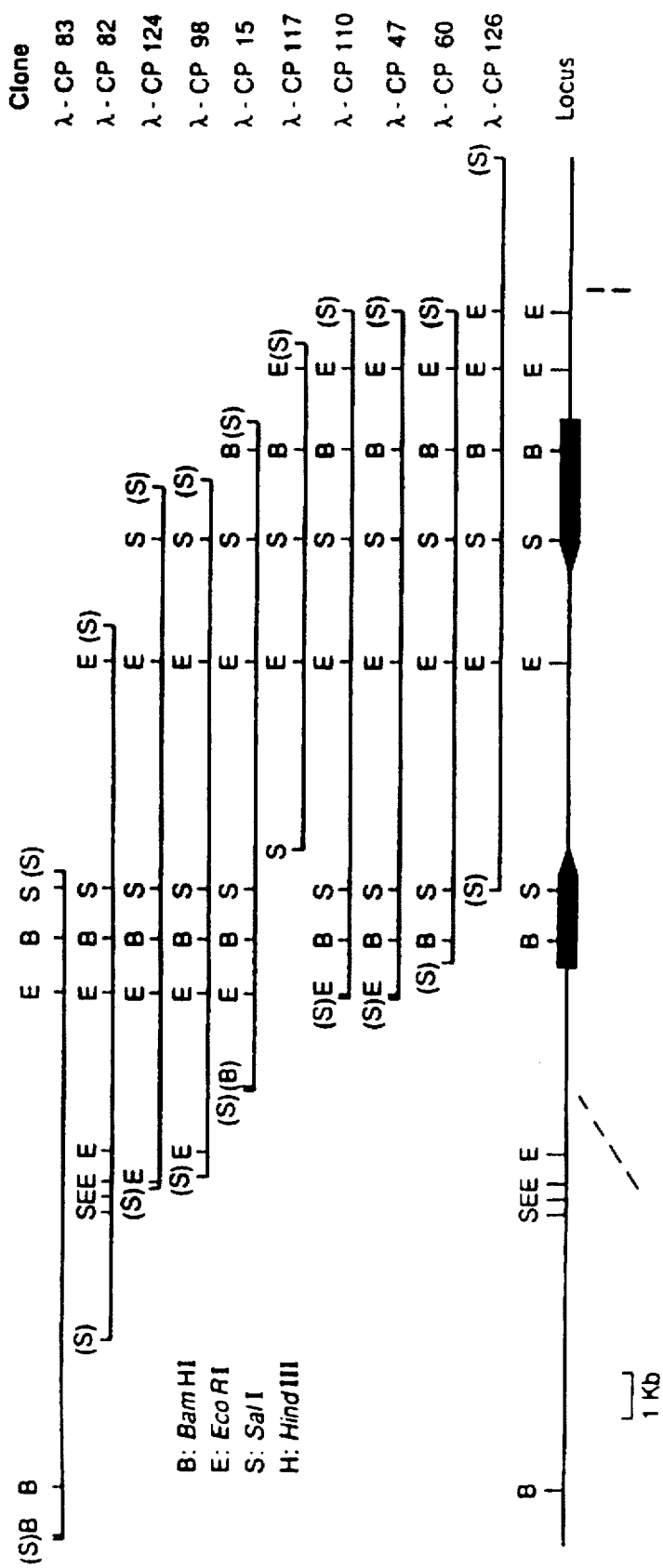
FIG. 2A shows the alignment of the retrieved clones with the position of the coding sequences on the genome.

The results after restriction analysis of the various genomic clones recovered is shown in FIG. 2A–C. As shown in the figure, two genomic clones reside on the same DNA strand, but are oriented in opposite directions. CP-ACC 1A and CP-ACC 1B each contain four introns. The complete genomic sequences of these clones are shown in FIGS. 3 and 4 respectively. As shown, the entire upstream regulatory sequences are included in the clones.

An alternative description for the isolation of the genomic sequences encoding ACC synthase in zucchini is set forth in Huang, P. L. et al., *Proc Natl Acad Sci USA* (1991) 88:7021–7025.

EXAMPLE 3

Retrieval of Tomato cDNA Encoding ACC Synthase

*Lycopersicon esculentum* c.v. Rutgers was grown from seeds throughout the year in a greenhouse using protocols to ensure freedom from tobacco mosaic virus. The fruit was frozen and total RNA was isolated from a ripe, wounded tomato fruit using the procedure of Chomczynski, P., et al. *Anal Biochem* (1987) 162:156–159. Approximately 5 gm of powdered frozen fruit tissue were used. Poly (A)⁺ RNA was isolated using oligo (dT) cellulose chromatography as described by Theologis, A., et al. *J Mol Biol* (1985) 183:53–58, and a cDNA library was constructed into λgt10 as described by Huynh, T. V., et al. *cDNA Cloning Techniques: A Practical Approach* (1985) (Glover, D. M. ed.), IRL Press, London, 49–78. cDNAs greater than 500 bp were inserted into the EcoRI site of the C1 repressor gene. The packaged DNA was plated on C600 HFL, a derivative of C600, to select for phage-containing inserts.

Approximately 10⁶ plaque forming units of the λgt10 recombinant phage were plated to a density of 1×10⁴ per 85 mm petri dish using C600. After transferring to nitrocellulose filters as described above, prehybridization and hybridization were performed at 37° C. with gentle agitation in 30% formamide, 5×SSPE (1×SSPE is 0.18M NaCl, 10 mM sodium phosphate, pH 7.0, 1 mM sodium EDTA), 5×BFP (1×BFP is 0.02% w/v bovine serum albumin, 0.02% polyvinyl pyrrolidone (M$_r$=360 kd), 0.02% Ficoll (M$_r$=400 kd), 100 mg/ml heat denatured salmon sperm DNA, and 0.1% SDS).

The gel purified 1.7 kb EcoRI fragment of the zucchini pACC1 prepared in Preparation A was labeled to a specific activity of 2×10⁸ cpm/mg using random hexamer priming and α-32P dCTP as described by Feinberg, A. P., et al., *Anal Biochem* (1983) 132:6–13. The labeled probe was separated from starting material and used to probe the λgt10 library.

The probe was denatured with 0.25 volumes 1M NaOH for 10 minutes at room temperature and neutralized with 0.25 volume 2M Tris HCl, pH 7.2 and then added to the hybridization mixture at 1×10⁶ cpm/ml.

After 24 hr hybridization, the filters were washed once in 30% formamide, 5×SSPE, 0.1% SDS at 37° C. for 20 min and then four times in 2×SSPE, 0.1% SDS at 37° C. for 20 min. The final wash was in 2×SSPE at 50° C. for 10 min.

After washing, the filters were air dried, covered with Saran wrap and exposed at −70° C. to X-ray film.

Using this hybridization, a full length cDNA encoding an ACC synthase from tomato was recovered and subcloned into the EcoRI site of pUC18 and was designated ptACC2. The complete cDNA sequence of the LE-ACC2 of tomato is shown in FIG. 5.

Figure 6:
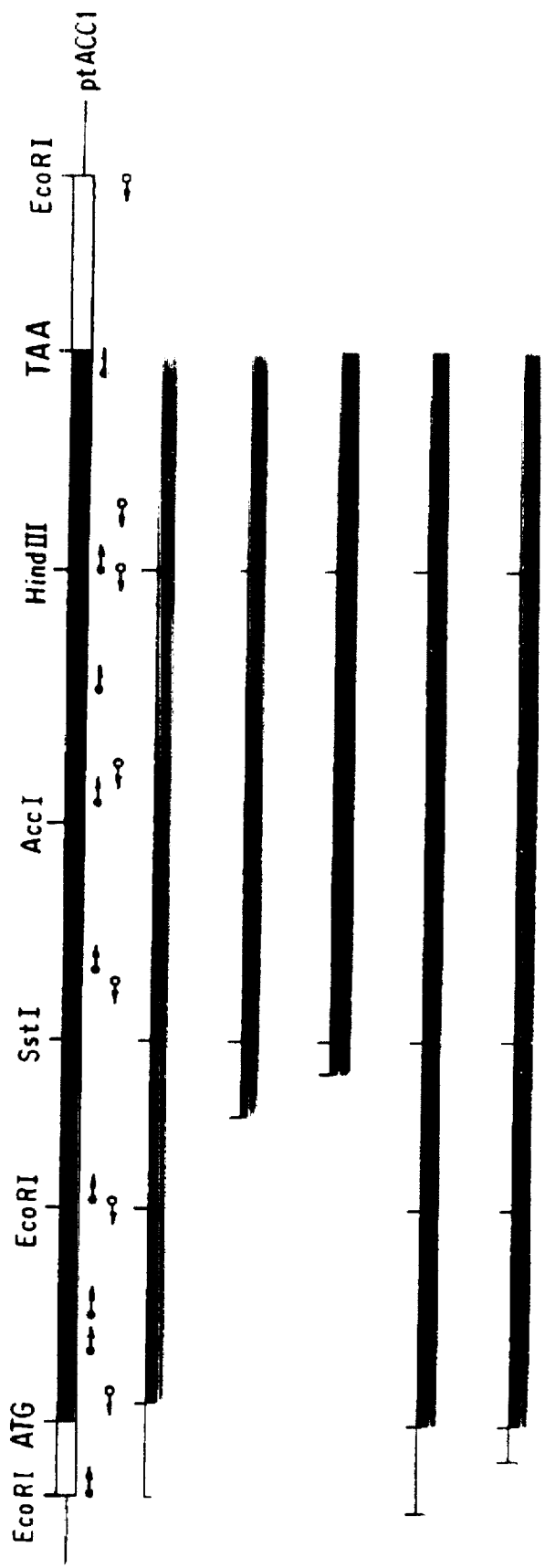
FIG. 6 shows a diagram and restriction map of several clones of the cDNA encoding tomato ACC synthase.

An additional clone was recovered using 2×10⁶ cpm of the labeled 0.55 kb HindIII/EcoRI fragment at the 3' end of ptACC2. Hybridization conditions were employed using 2×10⁵ pfu of the λgt10 library on C600 wherein nitrocellulose platelets were prehybridized at 42° C. and 50% formamide, 5×SSPE, 5×BFP, 500 mg/ml heat denatured salmon sperm DNA for 12 h. The filters were then hybridized for 18 hr at 42° C. with probe in 50% formamide, 5×SSPE, 1×BFP, 100 mg/ml heat denatured salmon sperm DNA with this probe. The filters were washed at 42° C. twice for 30 min in 50% formamide, 5×SSPE, 0.2% SDS, and then twice for 30 min in 0.1×SSPE at 42° C. Additional clones were retrieved using the above-referenced portion of ptACC2 as shown in FIG. 6.

A comparison of the amino acid sequences of the zucchini and tomato cDNA-encoded ACC synthases is shown in FIG. 10. As shown, considerable homology exists between these sequences, but they are not identical.

An alternative description of the retrieval of the insert of pt ACC2 and an additional clone designated ACC4 which is also obtainable from cDNA prepared from ripening tomato fruit is set forth in Rottmann, W. H. et al., *J Mol Biol* (1991) 222:937–961, incorporated herein by reference.

EXAMPLE 4

Recovery of Tomato Genomic DNA Encoding ACC Synthase

Genomic DNA was isolated from etiolated *Lycopersicon esculentum* c.v. Rutgers seedlings using a modification of the method described by Davis, R. W., et al. *Meth Enzymol* (1980) 65:404–411. Briefly, seedlings were grown on moist filter paper in the dark for 5 days at 22° C. Fifty g frozen hypocotyl and cotyledon tissue, seed coat removed, was ground in a coffee grinder. The powdered tissue was added to 200 ml of ice cold extraction buffer (50 mM Tris-HCl, pH 8.0, 50 mM NaEDTA, 0.25 M NaCl, 15% sucrose (w/v)) and homogenized on ice using a hand held glass-glass homogenizer. The nuclei were pelleted at 2000×g for 10 min at 4° C. The crude nuclei were resuspended in 100 ml of cold extraction buffer without the salt. To lyse the nuclei, 10 ml of 10% "Nasarcosine" was added, the suspension was gently inverted and incubated on ice for 10 min, then 120 g of CsCl was added and dissolved by gently shaking. To remove debris the solution was centrifuged at 26,000×g for 20 min at 4° C. and the supernatant was decanted through "Miracloth".

Ethidium bromide (10 mg/ml) was added to a final concentration of 0.4 mg/ml and the density of the solution was adjusted to 1.55 g/ml. Equilibrium centrifugation was carried out in a Beckman Ti70 rotor at 40,000 rpm for 48 hr at 20° C. The DNA was further purified by a second round of equilibrium centrifugation in a VTi65 rotor at 50,000 rpm for 16 hr at 20° C. Ethidium bromide was extracted from the DNA with isopropanol saturated with water containing 5 M NaCl and the DNA was dialyzed twice against 5000 volumes of TE (pH 7.5) to remove the CsCl. The typical yield was 15 µg/g fresh weight tissue.

Two genomic libraries were constructed, one with 15–23 kb Sau3A partially digested DNA in λEMBL3 and another with 6–8 kb DNA after complete HindIII digestion into λ2001. For the library constructed in λEMBL3, 100 µg of genomic DNA was digested with 1.5 units of Sau3A at 37° C. in 300 µl of medium salt buffer (MSB) plus 2 mM dithiothreitol (DTT) (1×MSB is 10 mM Tris-HCl, pH 7.5, 50 mM NaCl, 10 mM $MgSO_4$). One third of the reaction was removed at 7.5 min, at 10 min and at 12.5 min. At each time point digestion was stopped by adding 0.1 volume 0.5 M NaEDTA, pH 8.0 and storing on ice. The DNA was size fractionated in a 0.5% low melting temperature agarose gel by electrophoresis at 0.8 volts/cm for 24 h. The agarose gel electrophoresis buffer was 1×TAE, 40 mM Tris-HOAc, pH 8.0, 2 mM NaEDTA. The gel was soaked at room temperature for 3 hr in 1×TAE buffer containing 0.3 M NaCl. DNA was visualized with 365 nm ultraviolet light and the 15–23 kb size range was excised. The agarose was melted at 65° C. for 15 min and extracted twice with TE (pH 7.5)-saturated phenol, prewarmed to 37° C. The aqueous phase was extracted three times with ether and two volumes of EtOH were added. After overnight at −20° C. the DNA was collected by centrifugation and dissolved in TE, pH 7.5. Two µg of EMBL3 arms and 2 µg size selected DNA were combined in a final volume of 6 µl, 1 µl of 10×ligase buffer (1×ligase buffer is 66 mM Tris-HCl, pH 7.5, 5 mM $MgCl_2$) was added and the cohesive ends annealed at 42° C. for 15 min. The mixture was quickly cooled on ice and 1 µl each of 10 mM ATP and 50 mM DTT was added. The reaction was initiated with 1 µl (8 units) of T4 DNA ligase and incubated overnight at 14° C. One third of the ligation mix was packaged with Gigapak Gold (Stratagene) according to the manufacturer. Approximately $1 \times 10^6$ pfu were obtained when titered on C600.

For the HindIII library, 200 µg of genomic DNA was digested in 3.6 ml 1×MSB with 400 units of enzyme for 4 hr at 37° C. The DNA was separated on a 0.8% low melting temperature agarose gel and DNA in the 6–8 kb size range was isolated as described above. One µg of this DNA was ligated to 0.5 µg of λ2001 arms as described above in a final volume of 10 µl. One third of this ligation was packaged with Gigapak Gold and $5 \times 10^4$ pfu were obtained when plated on K802.

A BglII complete digest library and an MboI partial digest library of genomic DNA from tomato cultivar VF36, both in EMBL4, were provided by C. Corr and B. Baker. These libraries and the HindIII complete digest library in λ2001 were plated on the host K802 and probed at high stringency with the ptACC1 cDNA as described above to obtain clones corresponding to the cDNA. Clones corresponding to other genes were obtained by probing the Sau3A partial digest library in EMBL3 with the cDNA at low stringency. In two separate screenings, phage were plated on the hosts C600 or TC410, lifted and fixed to nitrocellulose filters as described above. Low stringency prehybridization and hybridization were done in 30% formamide, 5×SSPE, 5×BFP, 100 µg/ml denatured salmon sperm DNA, 0.2% SDS at 37° C. for 18 h each. Probe was used at a concentration of $10^6$ cpm/ml. Washing was done twice for 20 min in 30% formamide, 5×SSPE, 0.2% SDS at 37° C., and twice for 20 min in 2×SSPE, 0.2% SDS at 42° C. The filters were exposed to X-ray film as above for 48 h.

For restriction enzyme digestions of λ clones, 2.5 µg of phage DNA was digested in 50 µl of high salt buffer (HSB) (1×HSB is 100 mM NaCl, 50 mM Tris-HCl (pH 7.5), 10 mM $MgSO_4$) with the appropriate enzyme(s). For genomic DNA gel blots, 7.15 µg of genomic DNA was digested in 100 µl of 1×HSB with 80 units of EcoRI and HindIII or 40 units of BglII, at 37° C. for 6 h. Digested DNAs were loaded on 1 cm thick, 0.8% agarose gels and electrophoresed at 3 V/cm in 1×TAE buffer containing 0.5 µg/ml ethidium bromide. After electrophoresis the gel was photographed, the DNA was nicked with two 15 min treatments of 0.25M HCl, denatured with two 20 min treatments of 0.5M Tris-HCl (pH 7.5), 1.5M NaCl and neutralized with two 20 min treatments of 0.5M Tris-HCl (pH 7.5), 1.5M NaCl. The nucleic acids were transferred in 20×SSPE to a Nytran nylon membrane.

After transfer was complete the nucleic acids were fixed with 1.2 joules of 254 nm ultraviolet radiation. The membranes were prehybridized in 50 ml of 50% formamide, 5×SSPE, 5×BFP, 1.0% SDS and 100 µg/ml heat denatured salmon sperm DNA at 42° C. for 12 h. Hybridizations were carried out in 30 ml of 50% formamide, 5×SSPE, 1×BFP, 10% dextran sulfate ($M_r$=400 kd), 0.2% SDS, and 50 µg/ml heat-denatured salmon sperm DNA at 42° C. for 18 h. Filters with genomic DNA were hybridized with $2.0 \times 10^6$ cpm/ml, whereas filters with λ DNA were hybridized with $5 \times 10^5$ cpm/ml of random hexamer labeled 1.8 kb ptACC1 cDNA. After hybridization the membranes were washed two times for 20 min at 55° C. in 0.1×SSPE and 0.2% SDS, dried, wrapped in plastic warp and placed under Kodak XR-5 X-ray film. λ DNA gel blots were exposed for 12–24 hr at −70° C. with an intensifier screen.

Figure 7C:
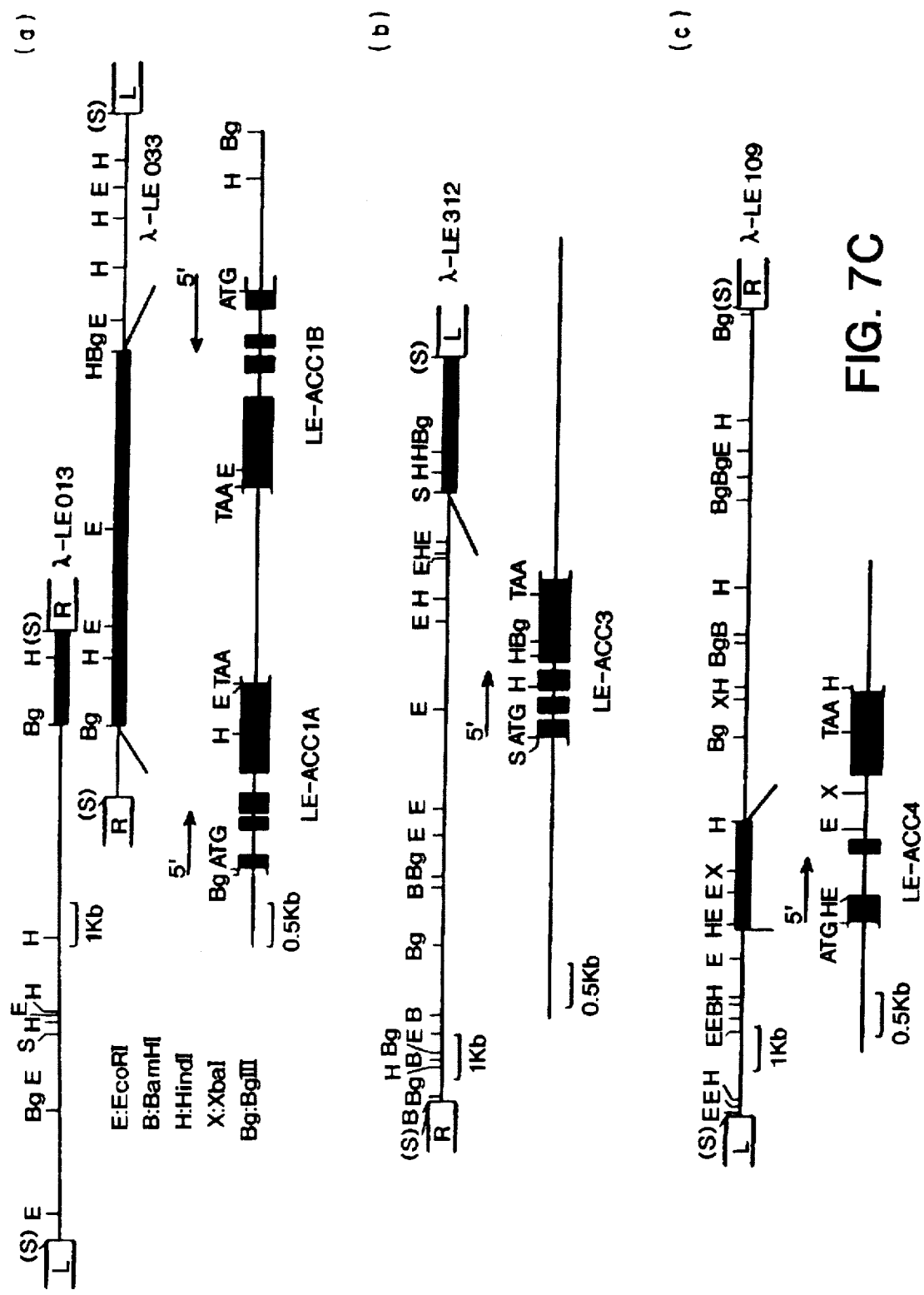
FIG. 7(A–C) shows the restriction enzyme pattern of genomic clones and functional diagrams thereof for the tomato genome containing coding and control sequences for LE-ACC 1A, LE-ACC 1B, and LE-ACC 3.
Figure 8:
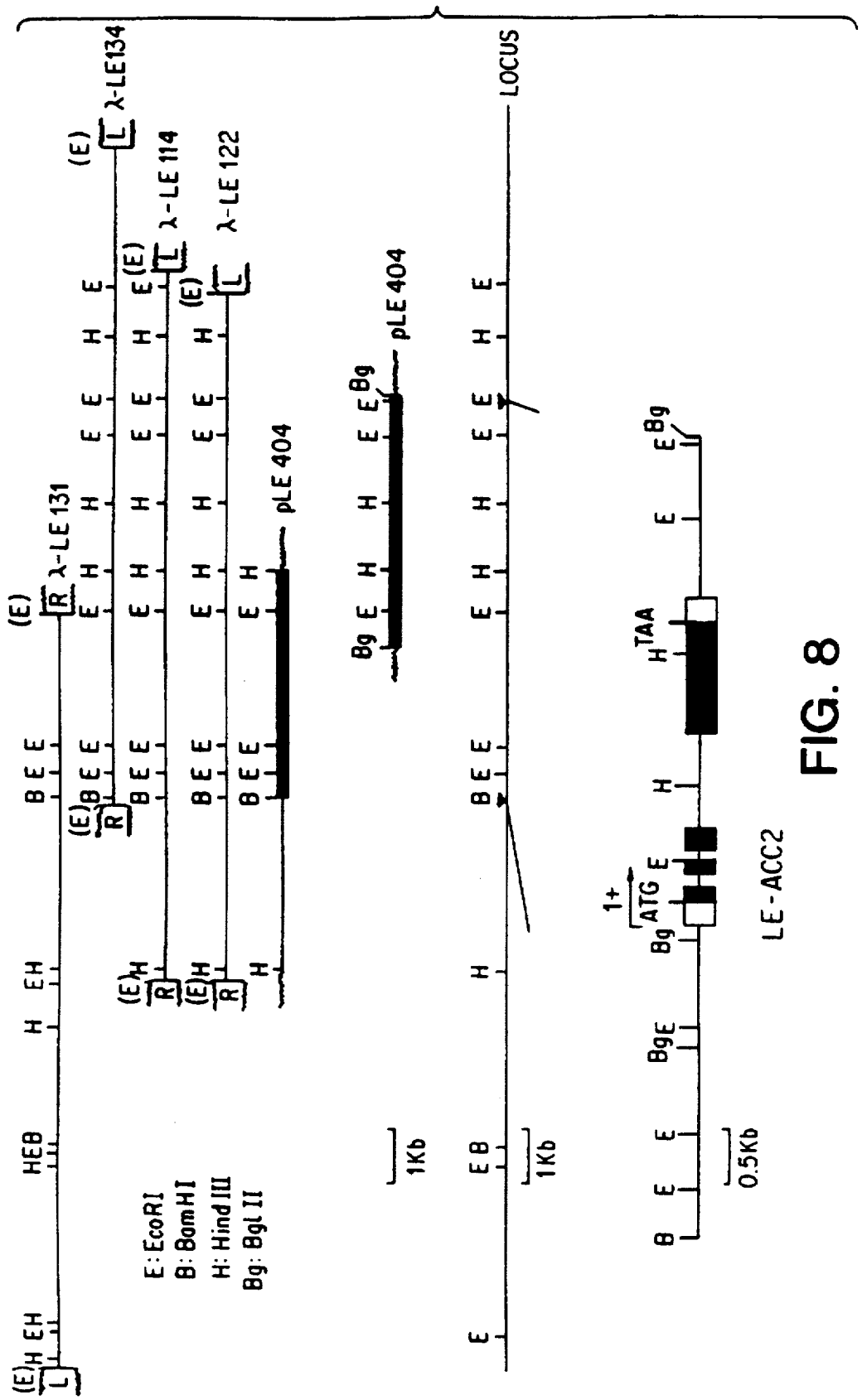
FIG. 8 shows the restriction enzyme pattern of genomic clones and the organization of the gene for LE-ACC 2.

The clones corresponding to five different genomic clones were recovered from tomato. A diagram of four of these is shown FIG. 7. FIG. 7A shows a series of two genomic clones which were identified to LE-ACC 1A and LE-ACC 1B; these genes are transcribed convergently. FIG. 7B shows a map of LE-ACC 3; FIG. 7C shows a map of Le-ACC 4. FIG. 8 shows a map of LE-ACC 2. FIG. 9 shows the complete nucleotide sequence of LE-ACC 2.

Table 1 shows a comparison of the properties of the ACC synthase peptides encoded by the genes known to encode this peptide in tomato and zucchini; FIG. 10 compares the amino acid sequences encoded by the seven genomic clones recovered-two from zucchini and five from tomato.

TABLE 1

| Gene | Amino acid no. | Predicted molecular mass (Da) | Isoelectric Point |
|---|---|---|---|
| CP-ACCIA | 493 | 55,779 | 6.84 |
| CP-ACCIB | 494 | 55,922 | 7.68 |
| LE-ACCIA | 485 | 54,809 | 5.94 |
| LE-ACCIB | 483 | 54,563 | 6.16 |
| LE-ACC2 | 48S | 54,662 | 7.71 |
| LE-ACC3 | 469 | 53,094 | 8.01 |
| LE-ACC4 | 476 | 53,509 | 5.40 |

Again, conserved sequences are found and there is considerable homology; however, there are numerous differences in sequence. This work is also described in Rottmann, W. H. et al., *J Mol Biol* (supra).

EXAMPLE 5

Expression of Zucchini and Tomato cDNA in E. coli

The pACC1 from zucchini was subcloned into the EcoRI site of the expression vector pKK223-3 (DeBoer, H. A., et al, Proc Natl Acad Sci USA (1983) 80:21–25) and introduced into E. coli strain JM107. Transformants were grown in LB medium in the presence of ampicillin (50 mg/ml) at 37° C. for 4 h. IPTG was added to 1 mM and the cultures were incubated for 2 hr at 37° C. ACC synthase activity and ACC formation were assayed. When the 1.7 kb EcoRI cDNA fragment was inserted into pKK2233-3 in the correct orientation and the transformed E. coli incubated as described above, ACC synthase activity was produced in the absence of IPTG at 20 nmol/h/mg protein and in presence of IPTG at 42 nmol/h/mg. ACC formation per 100 ml of culture was 2280 nmol without IPTG and 4070 nmol in the presence of IPTG. No ACC synthase activity or ACC production were observed when the 1–7 kb fragment was inserted in the opposite orientation.

Figure 11:
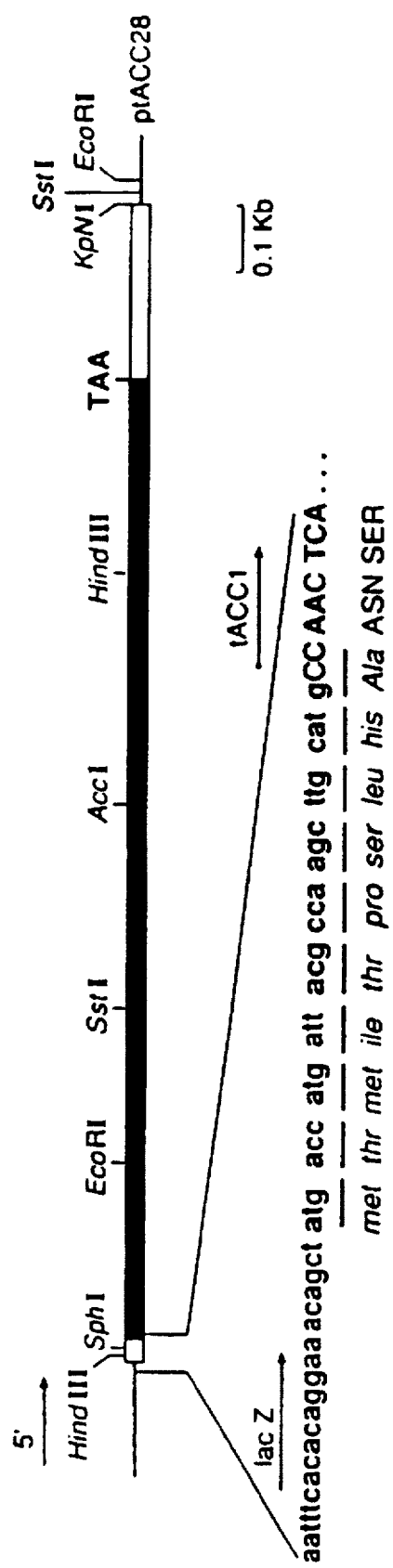
FIG. 11 shows the junction region and a restriction map of a bacterial expression vector for the production of tomato ACC synthase in bacteria.

A similar construct for tomato ACC synthase was used to test expression of the tomato cDNA in E. coli. The protein is synthesized as a fusion with a portion of the LacZ gene. The sequence at the junction is shown in FIG. 11.

For construction of the vector containing this junction, pETC3C (Rosenberg, A. H., et al. Gene (1987) 56:125–155) was modified by cutting with EcoRI and EcoRV and filling in with Klenow to remove a 375 bp fragment downstream of the T7 promoter. The resulting religated plasmid was named pP07. pP07 was cut with BamHI and NdeI and the large DNA segment was purified and ligated to a BamHI/NdeI polylinker containing an EcoRI site to obtain the intermediate plasmid pPO9.

Figure 15:
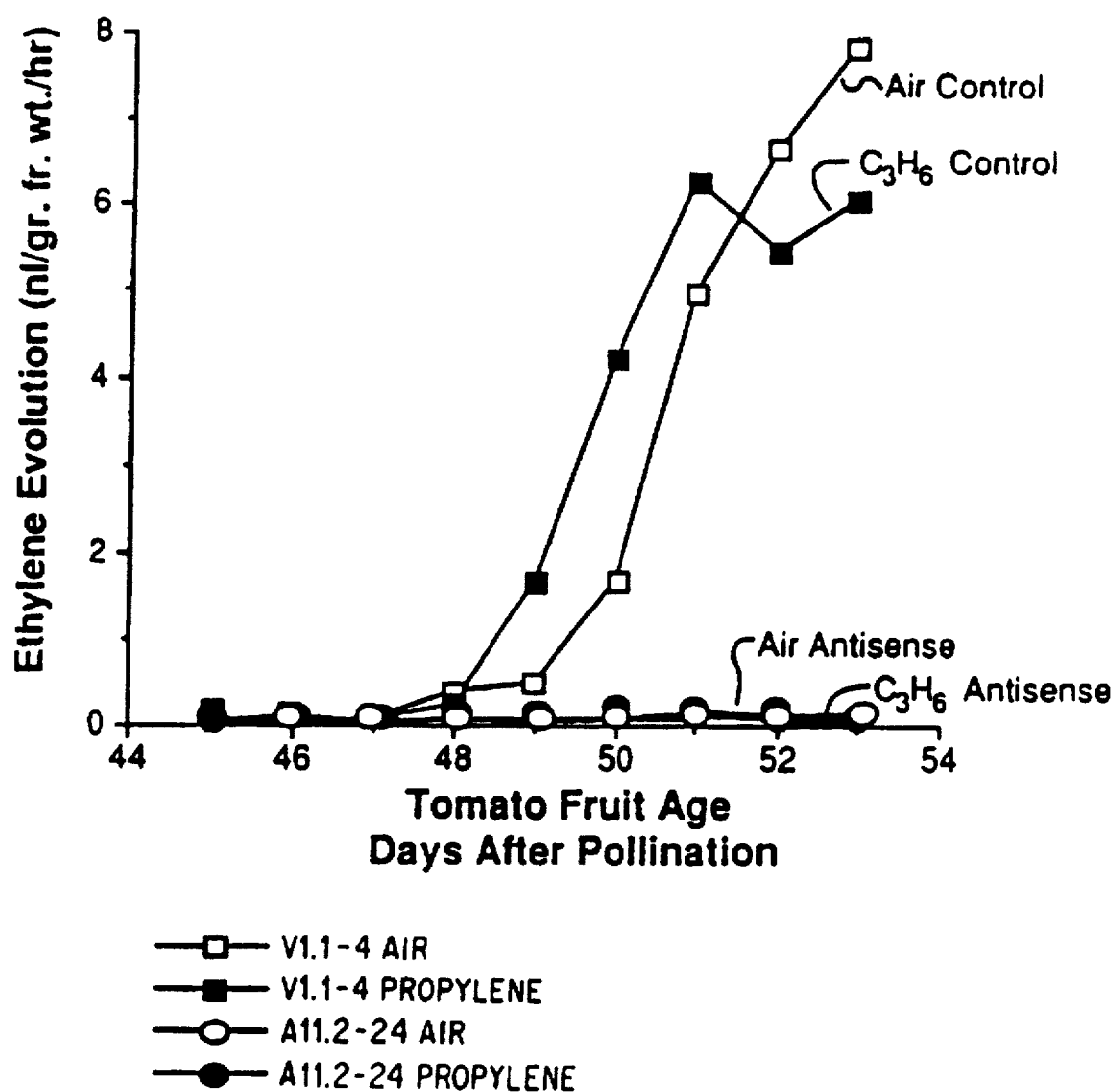
FIGS. 15 and 16 show the ethylene production by tomato plants regenerated from tomato cotyledons transformed with the vector of FIG. 14 as a function of days from pollination.

The 1.4 kb EcoRI fragment from ptACC2 was then ligated into the EcoRI site of pPO9 to obtain the junction shown in FIG. 15 and designated pPO46.

This plasmid was then used to transform E. coli BL21 (DE3) (Rosenberg et al. (supra)). The cultures were induced by diluting fresh overnight cultures into 2×TY (Maniatis et al. (supra)) and grown at 37° to an absorption at 600 nm of 0.7–0.8. IPTG was added to a final concentration of 2 mM and growth was continued for another two hours. The cells were harvested and the recombinant polypeptide was purified as described by Nagai, K. and Thogersen, A. C., Meth Enzymol (1987) 153:461–481.

Figure 12:
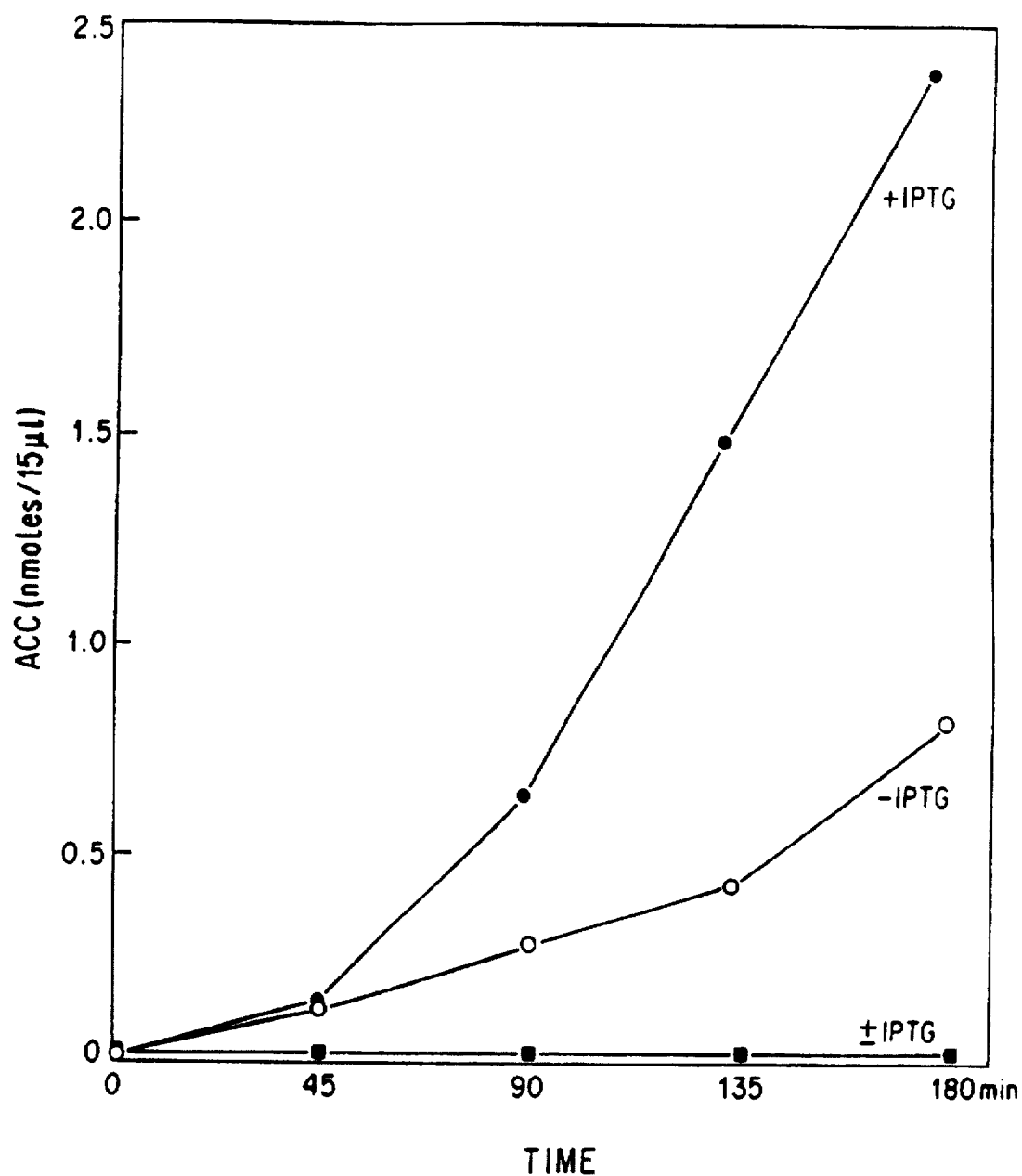
FIG. 12 shows the production of ACC by bacterial cultures transformed with the vector of FIG. 15 in the presence and absence of the inducer IPTG.

FIG. 12 shows the synthesis of ACC synthase in nmol/15 μl of culture transformed with the tomato ACC-containing vector in the presence and absence of IPTG. As shown in the figure, when the cDNA is ligated in the antisense direction, no ACC synthase is produced either in the presence or absence of IPTG (solid squares). When the cDNA is oriented in the correct orientation, after 180 min, over 2 nmol ACC synthase are produced per 15 μl in the presence of IPTG (solid circles), and between 0.5 and 1.0 nmol in the absence of IPTG (open circles).

Figures 13A, 13B, 13C:
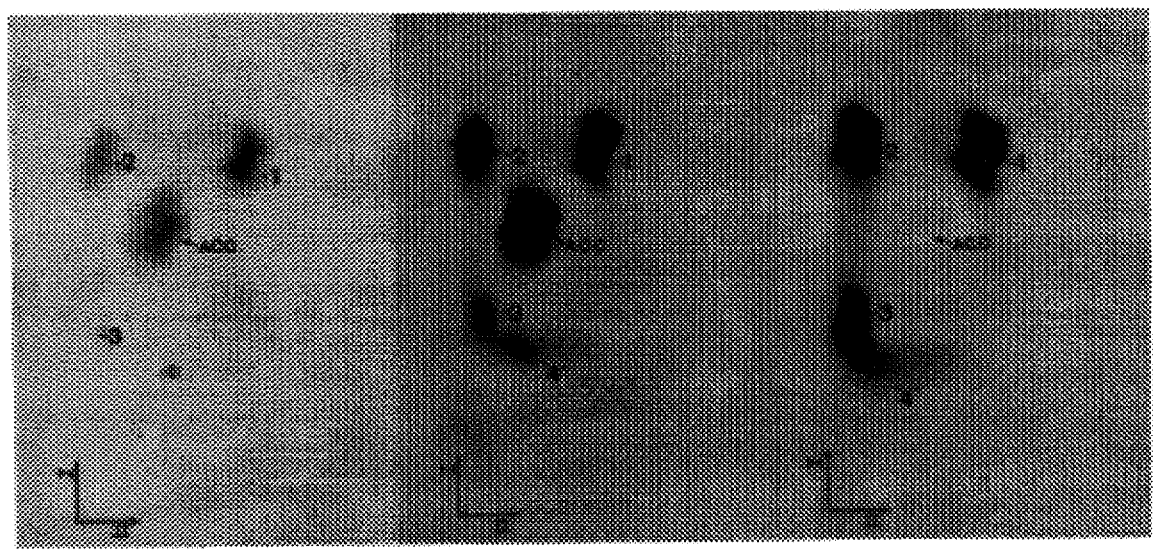
FIG. 13(A–C) is a half tone photograph of a two-dimensional chromatographic gel of bacterial extracts wherein the bacterial culture is transformed with an expression vector for tomato ACC synthase having the coding sequence in the correct and incorrect orientations.

The production of ACC using labeled $C^{14}$-carboxyl-labeled S-adenosyl-methionine is shown in FIGS. 13A–13C. In these figures, #1 is methionine, #2 is methionyl sulfite, #3 is methionyl sulfoxide, and #4 is unidentified. ACC is clearly labeled. FIG. 13A shows the results in the absence of IPTG; a little ACC is formed. FIG. 13C shows the results when the cDNA is ligated in the wrong orientation; no ACC is formed. FIG. 13B shows the production of labeled ACC when the correct orientation of the cDNA is used. A large quantity of ACC is produced.

EXAMPLE 6

Expression of Zucchini ACC Synthase in Yeast

The EcoRI fragment representing cDNA clone ACC1 was subcloned into the EcoRI site of the yeast expression vector pBM258 (Johnston, M., et al. Mol Cell Biol (1984) 4:1440–1448) and introduced into yeast strain YM2061. The yeast cells were grown on YP medium (Sherman, F., et al., Methods in Yeast Genetics (1979) Cold Spring Harbor Laboratory, Cold Spring Harbor, N.Y.) at 37° C. for 24 hr. The medium either contained 2% galactose or 2% glucose. After this culture, the cells were harvested and the supernatant was assayed for ACC released into the medium. The pelleted cells were resuspended in buffer containing 5 gm glass beads and vortex-mixed 10 times for 30 sec and centrifuged at 2000×g for 3 min. This supernatant was also collected. Solid ammonium sulfate was added to achieve 80% saturation and the precipitate was collected and dissolved in 2 ml of 20 mM Tris-HCl, pH 8.0, 10 μM pyridoxal phosphate, 10 mM EDTA, 0.5 mM dithiothreitol; and dialyzed against the same buffer. No ACC was produced in medium containing 2% glucose regardless of the construction of the vector. Control host vector and control vector with the ACC1 cDNA inserted in the antisense direction also gave no production of ACC in the cellular extract. However, when the medium contained 2% galactose, the pBM-ACC1 vectors containing the cDNA in the correct orientation did show the production of ACC in the crude extract as well as ACC activity in the extracted protein. ACC synthase activity was 2.6 nmol/hr/mg protein in the crude extract; 354 nmol of ACC were formed per 100 ml of culture.

EXAMPLE 7

Antisense Inhibition of Ethylene Production in Tomato Plants

The ripening of tomatoes was shown to be preventable by the transformation of tomato plants with an antisense construction of the tomato ACC synthase gene which, therefore, putatively inhibited the synthesis of indigenous ACC synthase. The cDNA clone was inserted in the opposite sense direction under the control of the cauliflower CaMV 35S promoter and used to transform tomato plantlets using the A. tumefaciens mediated method. The regenerated plants produced tomatoes which failed to ripen, and which produced no ethylene at the times after pollination wherein ethylene was produced in control plants.

A detailed description of these results is set forth in Oeller, P. W. et al., Science (1991) 254:437–439, incorporated herein by reference.

The antisense vector was constructed as follows: the 35S promoter was obtained as a 302 bp fragment from pJ024D (Ow, D. W., Proc Natl Acad Sci USA (1987) 84:4870–4874). The plasmid pJ024D was digested with HindIII, treated with Klenow, and then cut with BamHI to isolate the 302 bp fragment using gel electrophoresis. This was ligated to 3.5 kb of tomato ACC synthase cDNA by excising the transcribed sequence from ptACC2, which includes cDNA of the LE-ACC2 gene, by digestion with XbaI, filling with Klenow, and then cutting with BamHI. The two BamHI fragments were ligated and the resulting ligation transformed into E. coli strain DH5A for cloning. The recovered plasmid was named pPO32.

The plasmid pPO32 was partially digested with SacI and SalI and the digest was ligated into SalI/SacI digested pBI101 binary Ti vector (Clonetech). pBI101 further contains the NOS 3' terminating sequences. The construct is shown in FIG. 14. The resultant vector, designated pPO35 was transformed into *E. coli* DH5A for cloning. The sequences at the junctions were verified by sequence analysis.

pPO35 or a control vector without the ACC-synthase gene was purified and introduced into Agrobacterium strain LBA4404 by a standard procedure described briefly as follows: *A. tumefaciens* LBA-4404 (2 ml) was grown overnight at 28° C. in LB broth, and this used to inoculate 50 ml of LB broth to obtain the desired culture. The inoculated medium was grown at 28° C. until the $OD_{600}$ was 0.5–1.0. The cells were collected by centrifugation and the pellet was resuspended in 1 ml, 20 mM ice cold $CaCl_2$. To 100 µl of the cell suspension, 1 µm of pPO35 DNA was added, and the mixture was incubated on ice for 30 min before snap-freezing in liquid nitrogen. The cells were then thawed at 37° C. for 5 min and used to inoculate 1 ml LB. After 2 h growth at 28° C. with agitation, 100 µl of the culture were plated on LB+$Kan_{50}$ medium; colonies appeared in 2–3 days at 28° C. The cells were recultured by picking several colonies and streaking on LB+$Kan_{50}$ medium; again, 3–4 colonies were picked from independent streaks and 5 ml cultures in LB+$Kan_{50}$ medium were grown. Stationary phase of these cultures were used for transfection of tomato plants. The cells can be frozen using 15% glycerol at –80° C. to store for later use.

Preparation of Host Plants

Tomato seeds were sterilized using a protocol which consisted of treatment with 70% ethanol for 2 min with mixing; followed by treatment with 10% sodium hypochlorite and 0.1% SDS for 10 min with mixing, followed by treatment with 1% sodium hypochlorite, 0.1% SDS for 30 min with mixing, and washing with sterile water 3× for 2 min each wash.

For germination, 0.8 g of the sterilized seeds were placed in a Seed Germination Medium in a filled magenta box and grown for 2 weeks at low light in a growth room. The magenta box contained 30 ml of the medium.[1]

[1] Seed Germination Medium contains, per liter, 2.16 g of Murashige-Skoog salts; 2 ml of 500× B5 vitamins which had been stored at 20° C., 30 g sucrose and 980 ml water, brought to 1N KOH and containing 8 g agar. The medium is autoclaved in 500 ml portions before filling the magenta boxes.

After two weeks, when the seeds had germinated, cotyledons were dissected from the seedlings by cutting off the cotyledon tips and then cutting off the stem. This process was conducted in a large petri dish containing 5–10 ml of MSO.[2]

[2] MSO contains per liter 4.3 g of Murashige-Skoog salts, 2 ml of 500× B5 vitamins; 30 g of sucrose and 980 ml of water made 1N in KOH to a final pH of 5.8.

The harvested cotyledons were placed abaxial side up in tobacco feeder plates and grown for 48 h.

The feeder plates were prepared from a tobacco cell suspension in liquid medium[3] at 25° C. prepared with shaking at 130–150 rpm. The suspension was transferred to fresh medium at 1:10 dilution per every 3–5 days. 1 ml of rapidly dividing culture was placed on the feeder plate, overlaid with filter paper and placed in low light in a growth room. The feeder plates were supplemented with 10 ml Feeder Medium.[4] The Agrobacterium containing the pPO35 vector was inoculated into 50 ml LB containing kanamycin with a single colony of the strain. The culture was grown shaking vigorously at 30° C. to saturation (OD>2.0 at 600 nm). The strain was chosen to come to full growth in less than 24 h. The culture was then diluted to $5 \times 10^8$ cell/ml with MSO and split into 50 ml portions in plastic tubes.

[3] Tobacco Suspension Medium contains in 1 liter 4.3 g Murashige-Skoog salts, 2 ml of 500× B5 vitamins, 30 g 3% sucrose, 10 µl of a 0.5 mg/ml solution of kinetin stored at –20° C., 2 ml of a 2 mg/ml solution of pCPA, and 980 ml of water made 1N in KOH for a pH of 5.8 and autoclaved in 50 ml portions per 250 ml flask.

[4] Feeder Medium contains 0.43 g Murashige-Skoog salts, 2 ml 500× B5 vitamins, 30 g of sucrose and 980 ml water made 1N in KOH to a pH of 5.8, including 0.8% agar. The foregoing components are autoclaved in two 500 ml portions and hormones are added when pouring plates to obtain 1 µg/ml benzyl adenine (BA) and 0.2 µg/ml of indole acetic acid (IAA).

Cotyledons from two of the feeder plates were scraped into each tube and rocked gently for 10–30 min. The cotyledons were then removed from the bacterial culture into sterile filter paper abaxial side up on a tobacco feeder plate and incubated for 48 h in low light in a growth room.

The cotyledons were then transferred axial side up to Callus Inducing Medium.[5]

[5] Callus inducing Medium contains per liter 4.3 g of Murashige-Skoog salts, 2 ml of 500× B5 vitamins, 30 g of sucrose and 980 ml of water brought to 1N KOH at a pH of 5.8. The medium contains 0.8% agar and is autoclaved in two 500 ml portions. When poured into the plates, the following hormones are added to the following concentrations: 1 µm/ml BA, 0.2 µg/ml IAA, 100 µg/ml kanamycin, 500 µg/ml carbenicillin (Geopen).

In the Callus inducing Medium, approximately four plates were used per magenta box, and the explants were crowded. The box was placed in a growth room for three weeks, and small masses of callus formed at the surface of the cotyledons. The explants were transferred to fresh plates containing the callus inducing medium every three weeks.

When the calli exceeded 2 ml, they were transferred to plates containing shoot inducing medium.[6]

[6] Shoot Inducing Medium contains, per liter, 4.3 g of Murashige-Skoog salts, 2 ml of 500× B5 vitamins, 0.6 g of MES and 900 ml of water made 1N in KOH for a pH of 5.8, and 0.8% agar. The medium is autoclaved in two 450 ml portions and then is added 100 ml of a 30% filtered, sterilized glucose solution. When the plates are poured, additional components are added as follows: 0.1 mg/ml zeatin, 100 µg/ml kanamycin, 500 µg/ml carbenicillin.

When the stem structure was evident, the shoots were dissected from the calli and the shoots were transferred to root inducing medium-containing plates.[7]

[7] Root Inducing Medium contains, per liter, 4.3 g Murashige-Skoog salts, 2 ml 500× B5 vitamins, 30 g of sucrose and 980 ml of water, 1N in KOH to a pH of 5.8 in 8% agar. The medium is autoclaved in two 500 ml portions and when pouring plates, hormones are added to a concentration of 100 µg/ml kanamycin and 500 µg/ml or carbenicillin.

After a vigorous root system was formed on the plants, the plantlets were transferred to soil. To do this, they were taken from the plates, removing as much agar as possible and placed in a high peat content soil in a small peat pot which fits into a magenta box with cover. When the seedling leaves reached the top of the box, the lid was loosened and continued to be uncovered slowly over a period of 4–5 days. The plants were then transferred to a light cart and larger pots, and kept moist.

Figure 16:
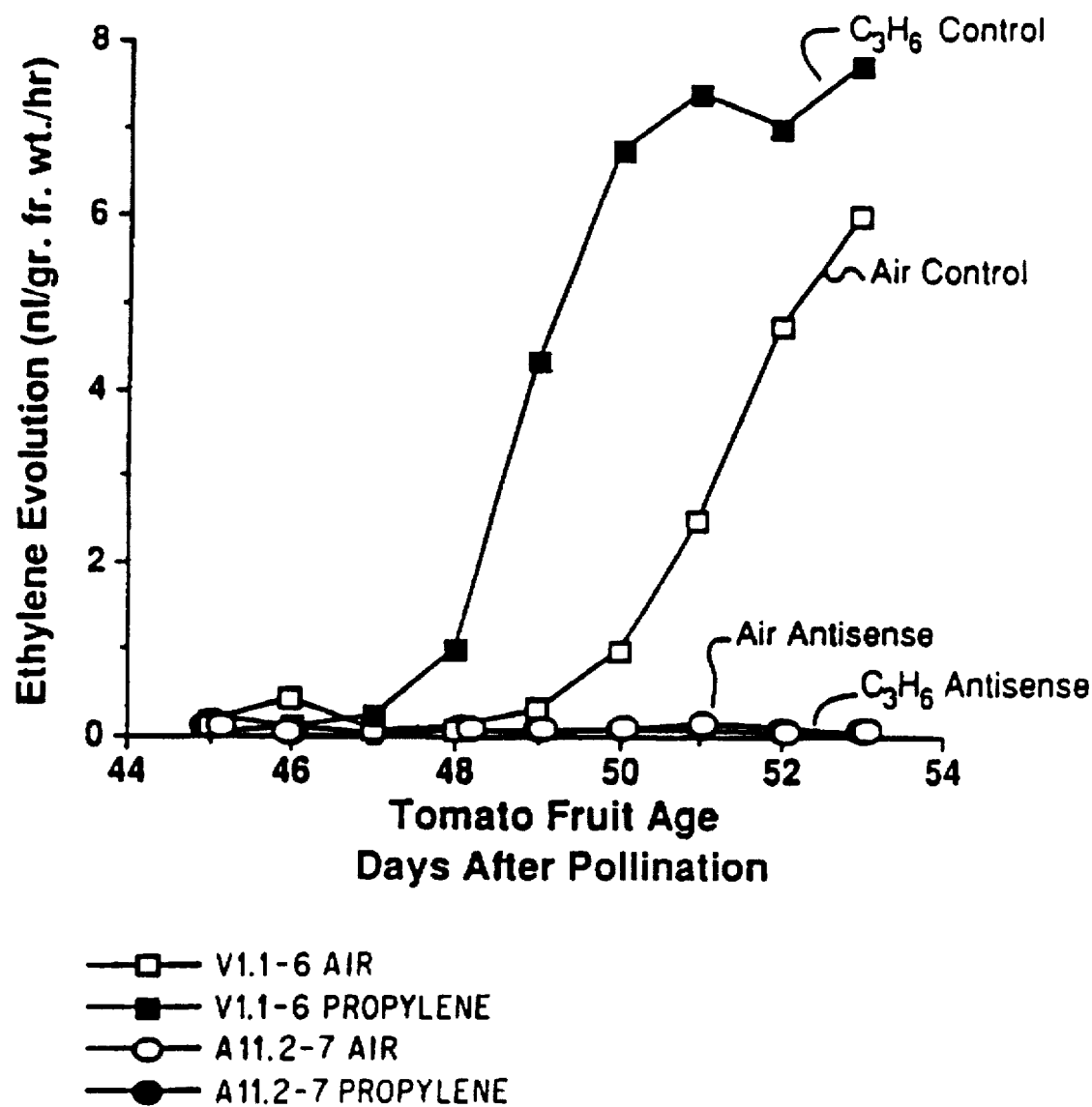

Flowers of these regenerated plants were pollinated and tomatoes were developed and ethylene measured by gas chromatography at specified days after pollination. FIGS. 15 and 16 show the results for two sets of individual plants V1.1–4 (which contains the control vector) and A11.2–24 (which contains the antisense vector) in FIG. 15 and V1.1–6 (which contains the control vector) and A11.2–7 (which contains the antisense vector) in FIG. 16. As shown in these figures, in both cases, the control plants which had been transformed with control vector produced high levels of ethylene up to 8 ng/g fruit/h after approximately 50 days after pollination either in the presence of propylene or in the presence of air. However, in both cases, there was no production of ethylene in those regenerated plants which had been transformed with the antisense pPO35 vector. In addition, the tomatoes which failed to produce ethylene also failed to ripen, whereas the control plants did ripen at this time.

Of 34 of the regenerated independent transgenic tomato plants obtained, three showed a marked inhibition of ethylene production and a delay in the onset of fruit ripening. The strongest phenotype was that of A11.1 which was chosen for further analysis with homozygous fruits from the second or third generation of the transgenic plants.

Southern Blot analysis showed that A11.1 plants obtained from seeds of the regerated plants contained an additional 1.7 kb DNA fragment that segregated as a single locus (3:1 ratio). A comparison of the hybridization intensities between the endogenous single copy LE-ACC2 synthase gene and the antisense gene indicates the presence of 10 antisense insertions per plant.

While control fruits kept in air begin to produce ethylene 48–50 days after pollination and then undergo a respiratory burst and fully ripen after 10 more days, ethylene production was inhibited by 99.5% in the fruits of A11.1 and these fruits failed to ripen. The antisense A11.1 fruits have a basal level of ethylene evolution of less than 0.31 nanoliters per gram of fruit; the red coloration resulting from chlorophyll degradation and lycopine biosynthesis is also inhibited and a progressive loss of chlorophyll from antisense fruits is seen 10–20 days later than the losses seen in control fruits, resulting in a yellow color. The antisense fruits kept in air or on the plants for 90–120 days eventually develop an orange color but never turn red and soft or develop an aroma. Antisense fruits in air do not show the respiratory burst even when they are 95 days old. Treatment with propylene or ethylene, however, induced ripening in the antisense plants but did not induce endogenous ethylene production. This treatment did induce the respiratory rise. Propylene or ethylene-ripened antisense fruits are indistinguishable from the naturally ripened fruits with respect to texture, color, aroma and compressibility.

Mature 57-day old green antisense fruits express ACC2 antisense RNA, whereas control fruits do not. Treatment with air or propylene for 14 days does not alter the amount of antisense RNA. The expression of. mRNAs from both ripening induced ACC synthase genes LE-ACC2 and LE-ACC4 is inhibited in antisense fruits treated with air or propylene.

The expression of two other genes, TOM13 and polygalacturonase (PG) (Hamilton, A. J., *Nature* (1990) 346:284; de la Pena, D. et al., *Proc Natl Acad Sci USA* (1986) 83:6420) was also analyzed.

U.S. Pat. No. 4,801,540 describes and claims the isolated PG-encoding gene. Giovannoni, J. J., et al., *The Plant Cell* (1989) 1:53–63, describes the expression of a chimeric PG gene in rin tomato fruits which results in polyuronide degradation but not fruit softening.

TOM13 mRNA is first detected in control fruits at about 48 days before ACC synthase mRNA is detectable and expression remains the same in air or propylene-treated control fruits. In antisense fruits, TOM13 and PG mRNA expression is similar to that in control fruits, demonstrating that expression of both genes during ripening is ethylene-independent.

It has been shown by others that antisense RNA to PG does not prevent tomato fruit ripening and expression of PG polypeptide in the tomato ripening mutant rin does not result in fruit softening.

To induce ripening in the antisense fruits, mature green fruits 49 days old from control and antisense plants were treated with ethylene for 1, 2, or 15 days. While antisense fruits treated for 1–2 days with ethylene did not develop a fully ripe phenotype, antisense fruits treated for 15 days with ethylene ripen normally. After 7 days of treatment, the fruits become fully red and soft. It was found that the ripening process requires continuous transcription of the necessary genes since ethylene treatment for one or two days was not sufficient. This may reflect a short half-life of the induced mRNAs or polypeptides. It is known that the half-life of the ACC synthase polypeptide is about 25 minutes (Kende, H. et al., *Plata* (1981) 151:476; Yoshi, H. et al., *Plant Cell Physiol* (1982) 23:639).

It should be noted that two other enzymes associated with tomato ripening have been used to construct antisense RNA-generating vectors which are unsuccessful in retarding the ripening of fruit (Hamilton, A. J. et al., *Nature* (1990) 346:284, cited above, and Smith, C. J. S., *Nature* (1988) 334:724). Thus, the association of the product of a gene with a ripening process does not lead to an expectation that the repression of the expression of that gene will impair ripening.

EXAMPLE 8

Purification of Native ACC Synthase from Cucurbita

ACC synthase was purified 6000-fold from induced Cucurbita homogenates according to a multistep protocol as shown below. Various buffers used in the purification are as follows:

Buffer A: Tris-HCl 100 mM, pH 8.0, EDTA 20 mM, pyridoxal phosphate 10 μM, PMSF 0.5 mM, β-mercaptoethanol 20 mM; Buffer B: Tris-HCl 20 mM, pH 8.0, EDTA 10 mM, pyridoxal phosphate 10 μM, DTT 0.5 mM; Buffer C: Na-acetate 20 mM, pH 6.0, pyridoxal phosphate 10 μM, EDTA 10 mM, DTT 0.5 mM; Buffer D: K-phosphate 10 mM, pH 8.0, pyridoxal phosphate 10 μM, EDTA 1 mM, DTT 0.5 mM; Buffer E: Tris-HCl 20 mM, pH 8.0, pyridoxal phosphate 5 μM, EDTA 1 mM, DTT 0.5 mM; Buffer F: Hepes-KOH 500 mM, pH 8.5, pyridoxal phosphate 40 μM, BSA 400 μg/ml.

All operations were performed at 4° C. Chromatographic elutions were assayed for ACC synthase activity and by absorption at 280 nm.

Ten kg of Cucurbita slices incubated for 24 hr in induction medium were chilled with liquid $N_2$ and homogenized in batches of 2 kg with 2 liters of buffer A plus 200 g of polyvinylpolypyrrolidone in a one gallon Waring® blender for 1 min at medium speed. The homogenate was centrifuged at 17,000×g for 30 min. The supernatant was filtered through one layer of Miracloth® and one layer of nylon cloth (30 μm mesh).

Butyl Toyopearl Fractionation-1

Solid ammonium sulfate was added slowly to the stirred supernatant above to achieve 40% saturation. The supernatant solution was stirred for 15 min and 300 ml of packed Butyl Toyopearl 650M hydrophobic affinity matrix, previously equilibrated with buffer B saturated to 40% with ammonium sulfate, were added. The suspension was occasionally stirred for an additional 30 min. The matrix was recovered by filtration through one layer of nitex nylon cloth (30 μm mesh) and the solution was squeezed out by hand. Subsequently, the matrix was placed in a vacuum filter with two sheets of Whatman® filter paper #1 and washed with 500 ml of buffer B containing 40% ammonium sulfate. The adsorbed proteins were eluted from the matrix by washing (twice) with 750 ml of buffer B, batchwise. The combined eluates were dialyzed three times against 10 liters of buffer B for 36 hr.

SP-Sephadex® Fractionation

The dialyzed fraction above was clarified by centrifugation at 17,000×g for 30 min. The volume was adjusted to 4 liters with buffer B and the pH was brought to pH 6.0 with 5% acetic acid. Two liters of packed SP-Sephadex® C-50 equilibrated with buffer C were added and the suspension was stirred for 60 min. The matrix was recovered by filtration through two sheets of Whatman® filter paper #1 and washed with 2 liters of buffer C. The adsorbed proteins were eluted twice with 1 liter of buffer B containing 1M KCl, batchwise. The eluant was recovered by suction through #1 Whatman® filter paper and solid ammonium sulfate was added to achieve 40% saturation. Subsequently 100 ml of Butyl Toyopearl-packed matrix equilibrated with buffer B/40% ammonium sulfate was added to the eluate. The suspension was stirred for 30 min and the matrix was collected by filtration through a layer of Nitrex® nylon cloth (30 μm mesh). The matrix was resuspended in a small volume of buffer B/40% ammonium sulfate and poured in a column (2.5×20 cm). The adsorbed proteins were eluted with buffer B, and the flow rate of the column was under gravity. Fractions with high $A_{280}$ were pooled and dialyzed overnight against 4 liters buffer B with three buffer changes during the course of dialysis.

QAE-Sephadex® Fractionation

Four hundred ml of packed QAE-Sephadex® equilibrated with buffer B were added to the dialyzate from the SP-Sephadex® fractionation and the suspension was stirred gently for 60 min. The matrix was recovered by filtration through a layer of Miracloth® in a filtration apparatus and washed with 500 ml of buffer B to remove unadsorbed proteins. The matrix was resuspended in a small volume of buffer B and poured into a column (4×30 cm). The proteins were eluted with buffer B containing 0.2M KCl.

Butyl Toyopearl Chromatography-2

Solid ammonium sulfate was added to the eluate (~100 ml) to achieve 40% saturation and the solution was kept at 4° C. for at least 4 hr. The suspension was centrifuged at 30,000×g for 30 min and the supernatant was applied on a Butyl Toyopearl column (1.5×14 cm) equilibrated with buffer B/40% ammonium sulfate. After all the protein solution was passed through the column, it was eluted with a 400 ml linear gradient: 40 to 0% ammonium sulfate in buffer B with a flow rate of 1 ml/min.

Figure 17A:
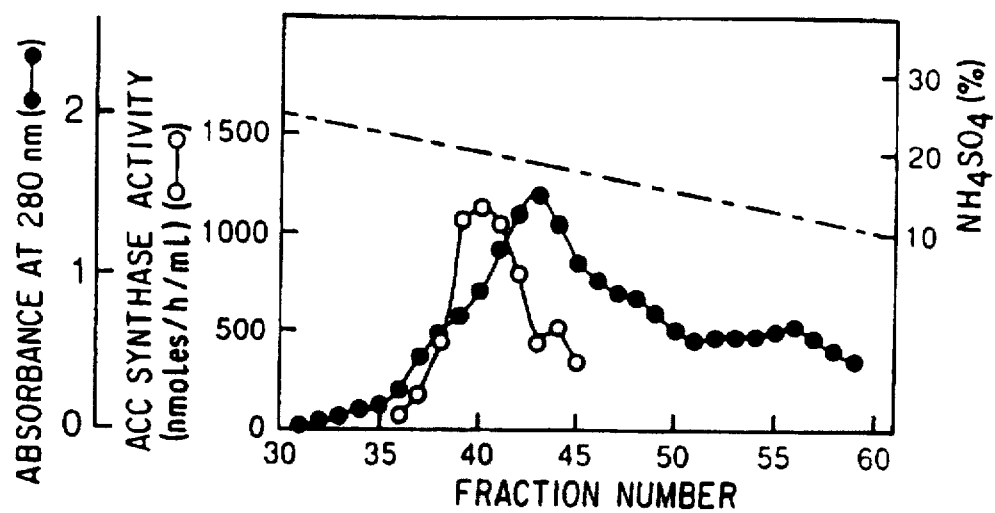
FIGS. 17A, 17B and 17C show the elution patterns obtained in the purification of ACC synthase from zucchini using butyl Toyopearl chromatography, Sephacryl S-300 chromatography, and BioGel HT chromatography, respectively.

FIG. 17A shows the elution pattern. Solid ammonium sulfate was added to enzymatically active fractions to achieve 80% saturation and the solution was incubated at 4° C. for at least 4 hr. The precipitate was collected by centrifugation at 30,000×g for 30 min at 4° C. and dissolved in 3 ml of buffer D.

Sephacryl S-300 Chromatography

Figure 17B:
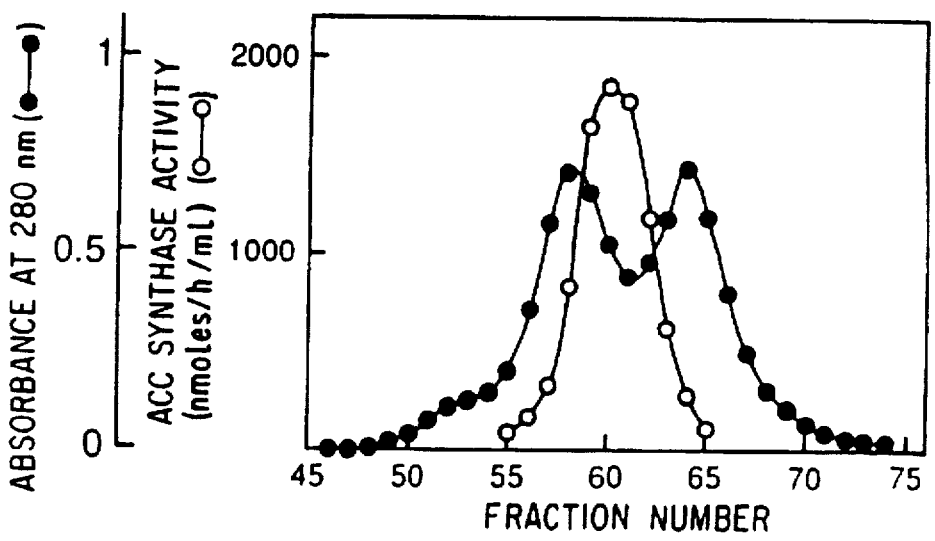

The resulting protein solution from above was applied to a column (2.5×100 cm) of Sephacryl S-300 equilibrated with buffer D. The column was eluted with buffer D at a flow rate of 0.5 ml/min. FIG. 17B shows the elution pattern.

Bio Gel-HT® Chromatography

Figure 17C:
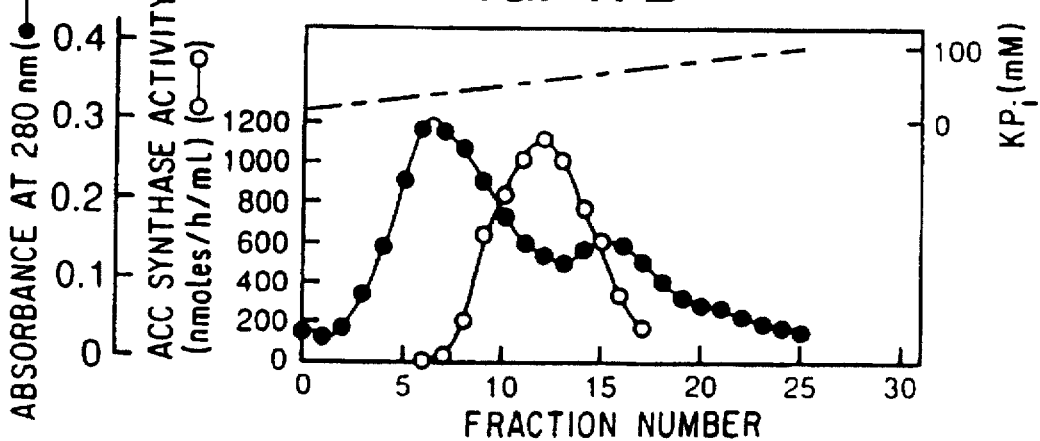

Active fractions from the Sephacryl step were combined and applied on a Bio Gel-HA column (0.75×14 cm) equilibrated with buffer D. The column was washed with buffer D until $A_{280}=0$ and it was then eluted with a 200 ml linear gradient: 10–100 mM potassium phosphate in buffer D with a flow rate of 0.1 ml/min. FIG. 17C shows the elution pattern. The active fractions were collected and concentrated with a Centricon 30 filtration apparatus, concomitantly the buffer of the concentrated protein solution was changed to buffer E.

FPLC Mono-Q Chromatography

Figure 18:
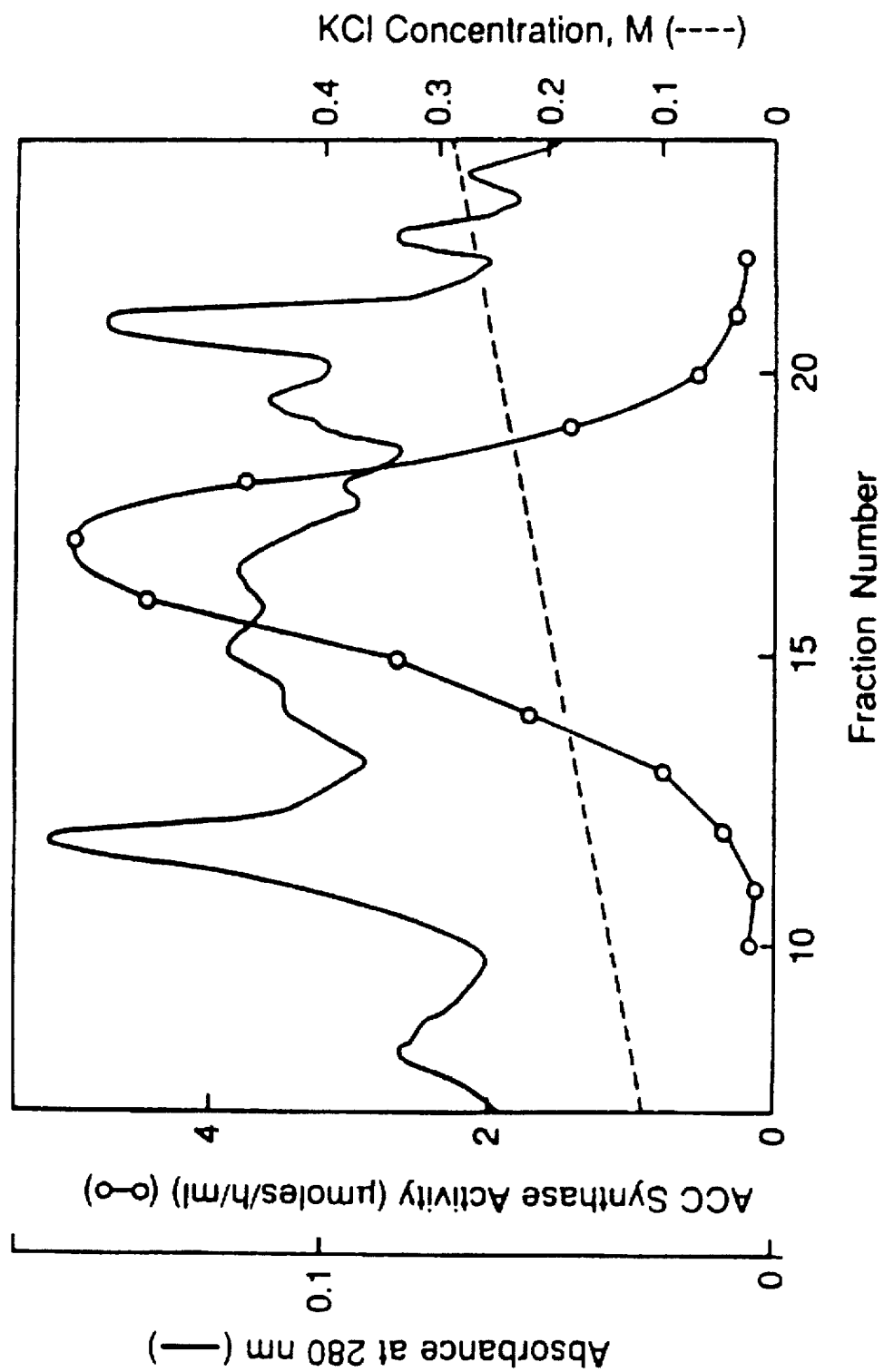
FIG. 18 shows the elution pattern obtained with FPLC Mono-Q chromatography.

The concentrated active fractions (~0.5 ml) from the Bio Gel-HT® column were applied to a mono-Q H5/5 column. The column was washed with buffer E containing 0.1M KCl until $A_{280}=0$. The column then was eluted with a 15 ml linear gradient: 0.1 to 0.4M KCl in buffer E. The flow rate of the gradient was 0.5 ml/min. FIG. 18 shows the elution pattern.

Table 2 shows the overall purification sequence and the increase in specific activity with each successive step. The overall process results in a 6000-fold purification with a recovery of 7.5%. The enzyme has a specific activity of 35,590 nmol ACC produced/hr/mg of protein.

TABLE 2

Partial Purification of ACC Synthase from Cucurbita Tissue Slices[a,b]

| | Step | Total Protein (mg) | Total Activity (nmol/ h) | Specific Activity (nmol/ h/mg protein) | Fold Purification | Recovery (%) |
|---|---|---|---|---|---|---|
| 1. | Crude Extract | 17,600 | 105,000 | 6 | 1 | 100 |
| 2. | Butyl Toyo- pearl 650M | 8,000 | 120,000 | 15 | 2.5 | 115 |
| 3. | SP-Sephadex ® | 800 | 49,000 | 62 | 10.4 | 47 |
| 4. | QAE-Sephadex ® | 336 | 45,800 | 136 | 23 | 44 |
| 5. | Butyl Toyo- pearl 650M | 67 | 13,500 | 201 | 34 | 13 |
| 6. | Sephacryl S-300 | 22 | 28,300 | 1,286 | 214 | 27 |
| 7. | Bio Gel-HT ® | 2.2 | 20,230 | 9,195 | 1,550 | 19 |
| 8. | Mono-Q | 0.22 | 7,830 | 35,590 | 6,000 | 7.5 |

[a]Amount of tissue: 10 kg
[b]Tissue treatment: IAA 0.5 mM + BA 0.1 mM + LiCl 50 mM + AOA 1 mM for 24 hr.

Figure 19:
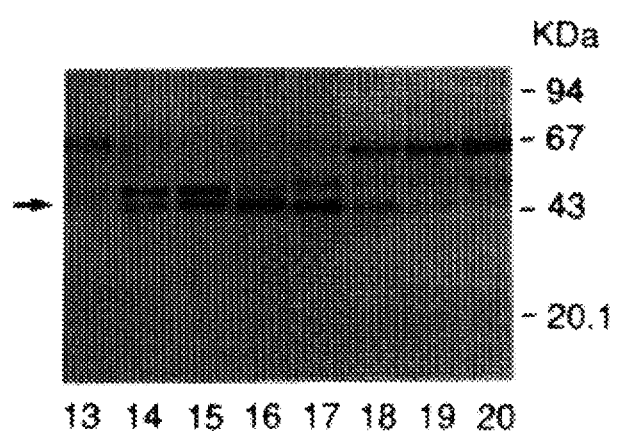
FIG. 19 is a halftone photograph showing the results of SDS-PAGE conducted on fractions obtained from the Mono-Q column of FIG. 18.

SDS-PAGE conducted on fractions 16 and 17 from the mono Q column, which have the highest ACC synthase activity, indicated that the protein was not completely pure. (See FIG. 19.) However, it was demonstrated that the ACC synthase activity resided in the 46 kd band. The electrophoresis was conducted by applying 7.5 ml of the eluted fractions mixed with an equal volume of 2×SDS loading buffer to a 10% polyacrylamide gel and silver staining. To determine the band containing ACC synthase activity, similar gels were run wherein the gels were cut into 3 mm thick slices and the ACC synthase activity was determined in half the slices; the other half were stained with silver.

The purified ACC synthase was also subjected to size exclusion chromatography on Sephacryl S-300. In this protocol, the ACC synthase eluted as an 86 kd species. This suggests that the Cucurbita ACC synthase consists of two identical 46 kd subunits. Further characterization showed that the pH optimum for ACC synthase activity is 9.5, and the isoelectric point is estimated at 5 using mono-P H 5/20 FPLC column chromatography. The Km for AdoMet is 16.7 mM, and pyridoxal phosphate is a cofactor. The enzyme is stable at −20° C. or −80° C. for over a year.

We claim:

1. A DNA molecule which comprises an expression system that generates, when contained in a plant host cell, an RNA which is sufficiently complementary to an RNA transcribed from an endogenous ACC synthase gene to prevent synthesis of said endogenous ACC synthase, wherein said expression system consists essentially of the reverse transcript of said complementary RNA operably linked to control sequences which effect its transcription into said complementary RNA wherein said RNA transcribed from an endogenous ACC synthase gene is capable of amplification by a combination of primers selected from the group consisting of:

that wherein the 5'→3' primer encodes MGLAENQ (SEQ ID NO:12) and the 3'→5' primer encodes FQDYHGL (SEQ ID NO:2);

that wherein the 5'→3' primer encodes FQDYHG (positions 1–6 of SEQ ID NO:2) and the 3'→5' primer encodes FMEK(V/T)R (SEQ ID NO:13);

that wherein the 5'→3' primer encodes KA(L/V) EEAY (SEQ ID NO:14) and the 3'→5' primer encodes FPG-FRVG (SEQ ID NO:15); and that wherein the 5'→3' primer encodes KALEEAY (SEQ ID NO:16) and the 3'→5' primer encodes RVCFANMD (SEQ ID NO:9).

2. A DNA molecule which comprises an expression system that generates, when contained in a plant host cell, an RNA which is sufficiently complementary to an RNA transcribed from an endogenous ACC synthase gene to prevent synthesis of said endogenous ACC synthase, wherein said system consists essentially of the reverse transcript of said complementary RNA operably linked to control sequences which effect its transcription into said complementary RNA wherein the endogenous ACC synthase gene is an ACC synthase gene of tomato.

3. The DNA molecule of claim 2 wherein said ACC synthase gene is LE-ACC 2 or LE-ACC 4.

4. A plant or plant cell modified to contain the DNA molecule of claim 1 wherein ethylene production in said plant or plant cell is inhibited as compared to unmodified plants or plant cells.

5. The plant or plant cell of claim 4 which is tomato.

6. A method to inhibit ethylene production in a plant or plant cell that normally produces ethylene, which method comprises including in said plant or plant cell the DNA molecule of claim 1 and culturing said plant or plant cell under conditions wherein said complementary RNA is expressed.

7. The method of claim 6 wherein said cell is a tomato cell and wherein said complementary RNA complements RNA transcribed from a tomato ACC synthase gene.

8. The method of claim 6 wherein said cell is a zucchini cell and wherein said complementary RNA complements RNA transcribed from a zucchini ACC synthase gene.

9. A transgenic plant which exhibits properties, one of which properties is a delay of fruit ripening, resulting from a lack of sufficient endogenous ACC synthase which plant has been modified to contain a DNA molecule comprising an expression system that generates an RNA complementary to RNA transcribed from an endogenous ACC synthase gene wherein said RNA transcribed from an endogenous ACC synthase gene is capable of amplification by a combination of primers selected from the group consisting of:

that wherein the 5'→3' primer encodes MGLAENQ and the 3'→5' primer encodes FQDYHGL;

that wherein the 5'→3' primer encodes FQDYHG and the 3'→5' primer encodes FMEK(V/T)R;

that wherein the 5'→3' primer encodes KA(L/V)EEAY and the 3'→5' primer encodes FPGFRVG; and that wherein the 5'→3' primer encodes KALEEAY and the 3'→5' primer encodes RVCFANMD.

10. The plant of claim 9 which is a tomato and wherein said complementary RNA is complementary to RNA transcribed from tomato ACC synthase.

11. A plant or plant cell modified to contain the DNA molecule of claim 2 wherein ethylene production in said plant or plant cell is inhibited as compared to unmodified plants or plant cells.

12. A method to inhibit ethylene production in a plant or plant cell that normally produces ethylene, which method comprises including in said plant or plant cell the DNA molecule of claim 2 and culturing said plant or plant cell under conditions wherein said complementary RNA is expressed.

13. The method of claim 12 wherein said plant or plant cell is a tomato plant or plant cell.

14. The method of claim 12 wherein said cell is a zucchini cell and wherein said complementary RNA complements RNA transcribed from a zucchini ACC synthase gene.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( x i ) SEQUENCE DESCRIPTION: SEQ ID NO:1:

Gln Met Gly Leu Ala Glu Asn Gln Leu
 1               5

( 2 ) INFORMATION FOR SEQ ID NO:2:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( x i ) SEQUENCE DESCRIPTION: SEQ ID NO:2:

Phe Gln Asp Tyr His Gly Leu
 1               5

( 2 ) INFORMATION FOR SEQ ID NO:3:

( i ) SEQUENCE CHARACTERISTICS:
  ( A ) LENGTH: 5 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 5
  ( D ) OTHER INFORMATION: /note= "This position is V/T."

( x i ) SEQUENCE DESCRIPTION: SEQ ID NO:3:

Phe Met Glu Lys Xaa
 1               5

( 2 ) INFORMATION FOR SEQ ID NO:4:

( i ) SEQUENCE CHARACTERISTICS:
  ( A ) LENGTH: 7 amino acids
  ( B ) TYPE: amino acid
  ( C ) STRANDEDNESS: single
  ( D ) TOPOLOGY: linear ( i x ) FEATURE:
  ( A ) NAME/KEY: Modified-site
  ( B ) LOCATION: 1
  ( D ) OTHER INFORMATION: /note= "This position is K/A."

( i x ) FEATURE:
  ( A ) NAME/KEY: Modified-site
  ( B ) LOCATION: 3
  ( D ) OTHER INFORMATION: /note= "This position is L/V."

( i x ) FEATURE:
  ( A ) NAME/KEY: Modified-site
  ( B ) LOCATION: 5
  ( D ) OTHER INFORMATION: /note= "This position is E/I."

( x i ) SEQUENCE DESCRIPTION: SEQ ID NO:4:

```
Xaa Ala Xaa Glu Xaa Ala Tyr
1               5
```

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 6
        ( D ) OTHER INFORMATION: /note= "This position is V/I."

( x i ) SEQUENCE DESCRIPTION: SEQ ID NO:5:

```
Gly Asp Ala Phe Leu Xaa Pro
1               5
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Asn Pro Leu Gly Thr
1               5
```

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Ser Leu Ser Lys Asp
1               5
```

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note= "This position is V/I."

( x i ) SEQUENCE DESCRIPTION: SEQ ID NO:8:

```
Pro Gly Phe Arg Xaa Gly
1               5
```

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:9:

```
Arg Val Cys Phe Ala Asn Met Asp
1               5
```

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:10:

```
Met Ser Ser Phe Gly Leu Val Ser
1               5
```

( 2 ) INFORMATION FOR SEQ ID NO:11:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 10
        ( D ) OTHER INFORMATION: /note= "This position is M/I."

( x i ) SEQUENCE DESCRIPTION: SEQ ID NO:11:

```
Gly Trp Phe Arg Val Cys Phe Ala Asn Xaa
1               5                   10
```

( 2 ) INFORMATION FOR SEQ ID NO:12:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:12:

```
Met Gly Leu Ala Glu Asn Gln
1               5
```

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note= "This position is V/I."

( x i ) SEQUENCE DESCRIPTION: SEQ ID NO:13:

```
Phe Met Glu Lys Xaa Arg
1               5
```

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i x ) FEATURE:
        ( A ) NAME/KEY: Modified-site (B) LOCATION: 3
(D) OTHER INFORMATION: /note= "This position is L/V."

(xi) SEQUENCE DESCRIPTION: SEQ ID NO:14:

```
Lys Ala Xaa Glu Glu Ala Tyr
1               5
```

(2) INFORMATION FOR SEQ ID NO:15:

(i) SEQUENCE CHARACTERISTICS:
- (A) LENGTH: 7 amino acids
- (B) TYPE: amino acid
- (C) STRANDEDNESS: single
- (D) TOPOLOGY: linear (xi) SEQUENCE DESCRIPTION: SEQ ID NO:15:

```
Phe Pro Gly Phe Arg Val Gly
1               5
```

(2) INFORMATION FOR SEQ ID NO:16:

(i) SEQUENCE CHARACTERISTICS:
- (A) LENGTH: 7 amino acids
- (B) TYPE: amino acid
- (C) STRANDEDNESS: single
- (D) TOPOLOGY: linear (xi) SEQUENCE DESCRIPTION: SEQ ID NO:16:

```
Lys Ala Leu Glu Glu Ala Tyr
1               5
```

(2) INFORMATION FOR SEQ ID NO:17:

(i) SEQUENCE CHARACTERISTICS:
- (A) LENGTH: 6 amino acids
- (B) TYPE: amino acid
- (C) STRANDEDNESS: single
- (D) TOPOLOGY: linear (xi) SEQUENCE DESCRIPTION: SEQ ID NO:17:

```
Thr Ala Thr Ala Ala Thr
1               5
```

(2) INFORMATION FOR SEQ ID NO:18:

(i) SEQUENCE CHARACTERISTICS:
- (A) LENGTH: 1703 base pairs
- (B) TYPE: nucleic acid
- (C) STRANDEDNESS: single
- (D) TOPOLOGY: linear (ix) FEATURE:
- (A) NAME/KEY: CDS
- (B) LOCATION: 11..1489

(xi) SEQUENCE DESCRIPTION: SEQ ID NO:18:

```
CAACTTTCAA ATG GGG TTT CAT CAA ATC GAC GAA AGG AAC CAA GCT CTT         49
           Met Gly Phe His Gln Ile Asp Glu Arg Asn Gln Ala Leu
             1               5                  10

CTC TCG AAG ATC GCC CTC GAC GAT GGC CAT GGC GAG AAC TCC CCG TAT        97
Leu Ser Lys Ile Ala Leu Asp Asp Gly His Gly Glu Asn Ser Pro Tyr
     15              20                  25

TTC GAT GGG TGG AAA GCT TAC GAT AAC GAT CCG TTT CAC CCT GAG AAT       145
Phe Asp Gly Trp Lys Ala Tyr Asp Asn Asp Pro Phe His Pro Glu Asn
 30              35                  40                      45

AAT CCT TTG GGT GTT ATT CAA ATG GGT TTA GCA GAA AAT CAG CTT TCC       193
Asn Pro Leu Gly Val Ile Gln Met Gly Leu Ala Glu Asn Gln Leu Ser
         50              55                      60
```

-continued

| | | | | | | | | | | | | | | | | |
|---|---|---|---|---|---|---|---|---|---|---|---|---|---|---|---|---|
| TTT | GAT | ATG | ATT | GTT | GAC | TGG | ATT | AGA | AAA | CAC | CCT | GAA | GCT | TCG | ATT | 241 |
| Phe | Asp | Met | Ile | Val | Asp | Trp | Ile | Arg | Lys | His | Pro | Glu | Ala | Ser | Ile | |
| | | | 65 | | | | 70 | | | | | 75 | | | | |
| TGT | ACA | CCG | GAA | GGA | CTT | GAG | AGA | TTC | AAA | AGC | ATT | GCC | AAC | TTC | CAA | 289 |
| Cys | Thr | Pro | Glu | Gly | Leu | Glu | Arg | Phe | Lys | Ser | Ile | Ala | Asn | Phe | Gln | |
| | | 80 | | | | | 85 | | | | | 90 | | | | |
| GAT | TAC | CAC | GGC | TTA | CCA | GAG | TTT | CGA | AAT | GCA | ATT | GCA | AAT | TTT | ATG | 337 |
| Asp | Tyr | His | Gly | Leu | Pro | Glu | Phe | Arg | Asn | Ala | Ile | Ala | Asn | Phe | Met | |
| | 95 | | | | | 100 | | | | | 105 | | | | | |
| GGG | AAA | GTA | AGA | GGT | GGG | AGG | GTA | AAA | TTC | GAC | CCG | AGT | CGG | ATT | GTG | 385 |
| Gly | Lys | Val | Arg | Gly | Gly | Arg | Val | Lys | Phe | Asp | Pro | Ser | Arg | Ile | Val | |
| 110 | | | | | 115 | | | | | 120 | | | | | 125 | |
| ATG | GGT | GGC | GGT | GCG | ACC | GGA | GCG | AGC | GAA | ACC | GTC | ATC | TTT | TGT | TTG | 433 |
| Met | Gly | Gly | Gly | Ala | Thr | Gly | Ala | Ser | Glu | Thr | Val | Ile | Phe | Cys | Leu | |
| | | | | 130 | | | | | 135 | | | | | 140 | | |
| GCG | GAT | CCG | GGG | GAT | GCT | TTT | TTG | GTT | CCT | TCT | CCA | TAT | TAT | GCA | GGA | 481 |
| Ala | Asp | Pro | Gly | Asp | Ala | Phe | Leu | Val | Pro | Ser | Pro | Tyr | Tyr | Ala | Gly | |
| | | | 145 | | | | | 150 | | | | | 155 | | | |
| TTT | GAT | CGA | GAC | TTG | AAA | TGG | CGA | ACA | CGA | GCA | CAA | ATA | ATT | CGG | GTC | 529 |
| Phe | Asp | Arg | Asp | Leu | Lys | Trp | Arg | Thr | Arg | Ala | Gln | Ile | Ile | Arg | Val | |
| | | | 160 | | | | 165 | | | | | 170 | | | | |
| CAT | TGC | AAC | GGC | TCG | AAT | AAC | TTC | CAA | GTC | ACA | AAG | GCA | GCC | TTA | GAA | 577 |
| His | Cys | Asn | Gly | Ser | Asn | Asn | Phe | Gln | Val | Thr | Lys | Ala | Ala | Leu | Glu | |
| | 175 | | | | | 180 | | | | | 185 | | | | | |
| ATA | GCC | TAC | AAA | AAG | GCT | CAA | GAG | GCC | AAC | ATG | AAA | GTG | AAG | GGT | GTT | 625 |
| Ile | Ala | Tyr | Lys | Lys | Ala | Gln | Glu | Ala | Asn | Met | Lys | Val | Lys | Gly | Val | |
| 190 | | | | | 195 | | | | | 200 | | | | | 205 | |
| ATA | ATC | ACC | AAT | CCC | TCA | AAT | CCC | TTA | GGC | ACA | ACG | TAC | GAC | CGT | GAC | 673 |
| Ile | Ile | Thr | Asn | Pro | Ser | Asn | Pro | Leu | Gly | Thr | Thr | Tyr | Asp | Arg | Asp | |
| | | | | 210 | | | | | 215 | | | | | 220 | | |
| ACT | CTT | AAA | ACC | CTC | GTC | ACC | TTT | GTG | AAT | CAA | CAC | GAC | ATT | CAC | TTA | 721 |
| Thr | Leu | Lys | Thr | Leu | Val | Thr | Phe | Val | Asn | Gln | His | Asp | Ile | His | Leu | |
| | | | 225 | | | | | 230 | | | | | 235 | | | |
| ATA | TGC | GAT | GAA | ATA | TAC | TCT | GCC | ACT | GTC | TTC | AAA | GCC | CCA | ACC | TTC | 769 |
| Ile | Cys | Asp | Glu | Ile | Tyr | Ser | Ala | Thr | Val | Phe | Lys | Ala | Pro | Thr | Phe | |
| | | 240 | | | | | 245 | | | | | 250 | | | | |
| ACC | AGC | ATC | GCT | GAG | ATT | GTT | GAA | CAA | ATG | GAG | CAT | TGC | AAG | AAG | GAG | 817 |
| Thr | Ser | Ile | Ala | Glu | Ile | Val | Glu | Gln | Met | Glu | His | Cys | Lys | Lys | Glu | |
| | 255 | | | | | 260 | | | | | 265 | | | | | |
| CTC | ATC | CAT | ATT | CTT | TAT | AGC | TTG | TCC | AAA | GAC | ATG | GGC | CTC | CCT | GGT | 865 |
| Leu | Ile | His | Ile | Leu | Tyr | Ser | Leu | Ser | Lys | Asp | Met | Gly | Leu | Pro | Gly | |
| 270 | | | | | 275 | | | | | 280 | | | | | 285 | |
| TTT | CGA | GTT | GGA | ATT | ATT | TAT | TCT | TAC | AAC | GAT | GTC | GTC | GTC | CGC | CGT | 913 |
| Phe | Arg | Val | Gly | Ile | Ile | Tyr | Ser | Tyr | Asn | Asp | Val | Val | Val | Arg | Arg | |
| | | | | 290 | | | | | 295 | | | | | 300 | | |
| GCT | CGG | CAG | ATG | TCG | AGC | TTC | GGC | CTC | GTC | TCG | TCC | CAG | ACT | CAA | CAT | 961 |
| Ala | Arg | Gln | Met | Ser | Ser | Phe | Gly | Leu | Val | Ser | Ser | Gln | Thr | Gln | His | |
| | | | 305 | | | | | 310 | | | | | 315 | | | |
| TTG | CTC | GCC | GCC | ATG | CTT | TCC | GAC | GAG | GAC | TTT | GTC | GAC | AAA | TTT | CTT | 1009 |
| Leu | Leu | Ala | Ala | Met | Leu | Ser | Asp | Glu | Asp | Phe | Val | Asp | Lys | Phe | Leu | |
| | | 320 | | | | | 325 | | | | | 330 | | | | |
| GCC | GAG | AAC | TCG | AAG | CGT | GTG | GGC | GAG | AGG | CAT | GCA | AGG | TTC | ACA | AAA | 1057 |
| Ala | Glu | Asn | Ser | Lys | Arg | Val | Gly | Glu | Arg | His | Ala | Arg | Phe | Thr | Lys | |
| | 335 | | | | | 340 | | | | | 345 | | | | | |
| GAA | TTG | GAT | AAA | ATG | GGG | ATC | ACT | TGC | TTG | AAC | AGC | AAT | GCT | GGA | GTT | 1105 |
| Glu | Leu | Asp | Lys | Met | Gly | Ile | Thr | Cys | Leu | Asn | Ser | Asn | Ala | Gly | Val | |
| 350 | | | | | 355 | | | | | 360 | | | | | 365 | |
| TTT | GTG | TGG | ATG | GAT | CTA | CGG | AGG | CTA | TTA | AAA | GAC | CAA | ACC | TTC | AAA | 1153 |
| Phe | Val | Trp | Met | Asp | Leu | Arg | Arg | Leu | Leu | Lys | Asp | Gln | Thr | Phe | Lys | |
| | | | | 370 | | | | | 375 | | | | | 380 | | |

| | | | | | | | | | | | | | | | | |
|---|---|---|---|---|---|---|---|---|---|---|---|---|---|---|---|---|
| GCT | GAA | ATG | GAG | CTT | TGG | CGT | GTG | ATT | ATC | AAT | GAA | GTC | AAG | CTC | AAT | 1201 |
| Ala | Glu | Met | Glu | Leu | Trp | Arg | Val | Ile | Ile | Asn | Glu | Val | Lys | Leu | Asn | |
| | | 385 | | | | | | 390 | | | | | 395 | | | |
| GTT | TCT | CCT | GGC | TCA | TCC | TTT | CAT | GTC | ACT | GAG | CCA | GGT | TGG | TTT | CGA | 1249 |
| Val | Ser | Pro | Gly | Ser | Ser | Phe | His | Val | Thr | Glu | Pro | Gly | Trp | Phe | Arg | |
| | | 400 | | | | | 405 | | | | | 410 | | | | |
| GTT | TGT | TTC | GCA | AAC | ATG | GAC | GAC | AAC | ACC | GTT | GAC | GTT | GCT | CTC | AAT | 1297 |
| Val | Cys | Phe | Ala | Asn | Met | Asp | Asp | Asn | Thr | Val | Asp | Val | Ala | Leu | Asn | |
| | | 415 | | | | 420 | | | | | 425 | | | | | |
| AGA | ATC | CAT | AGC | TTT | GTC | GAA | AAC | ATC | GAC | AAG | AAG | GAA | GAC | AAT | ACC | 1345 |
| Arg | Ile | His | Ser | Phe | Val | Glu | Asn | Ile | Asp | Lys | Lys | Glu | Asp | Asn | Thr | |
| 430 | | | | | 435 | | | | | 440 | | | | | 445 | |
| GTT | GCA | ATG | CCA | TCG | AAA | ACG | AGG | CAT | CGA | GAT | AAT | AAG | TTA | CGA | TTG | 1393 |
| Val | Ala | Met | Pro | Ser | Lys | Thr | Arg | His | Arg | Asp | Asn | Lys | Leu | Arg | Leu | |
| | | | | 450 | | | | | 455 | | | | | 460 | | |
| AGC | TTC | TCC | TTC | TCA | GGG | AGA | AGA | TAC | GAC | GAG | GGC | AAC | GTT | CTT | AAC | 1441 |
| Ser | Phe | Ser | Phe | Ser | Gly | Arg | Arg | Tyr | Asp | Glu | Gly | Asn | Val | Leu | Asn | |
| | | | 465 | | | | | 470 | | | | | 475 | | | |
| TCA | CCG | CAC | ACG | ATG | TCG | CCT | CAC | TCG | CCG | TTA | GTA | ATA | GCA | AAA | AAT | 1489 |
| Ser | Pro | His | Thr | Met | Ser | Pro | His | Ser | Pro | Leu | Val | Ile | Ala | Lys | Asn | |
| | | 480 | | | | | 485 | | | | | 490 | | | | |

```
TAATTAAAAA CATTTTTCAA AATATTCATA CCATTCATAT AGTTTTTTTT TTTTTTTTTT    1549
TTGGGTCAAT GTTGACTAAA GTTACGTATA TTTTTCCAC  AGTGGATATG ATGTAAACTT    1609
CATATTTTTT GGTGGGATGG TGATAGATGT AATGTATTTG GTTTTCCCT  TAGGGAACTC    1669
ATACTTATTT ATTAATGAAA TGATTGTGAT TTAT                                1703
```

( 2 ) INFORMATION FOR SEQ ID NO:19:

( i ) SEQUENCE CHARACTERISTICS:
( A ) LENGTH: 493 amino acids
( B ) TYPE: amino acid
( D ) TOPOLOGY: linear ( i i ) MOLECULE TYPE: protein ( x i ) SEQUENCE DESCRIPTION: SEQ ID NO:19:

```
Met Gly Phe His Gln Ile Asp Glu Arg Asn Gln Ala Leu Leu Ser Lys
 1               5                  10                  15

Ile Ala Leu Asp Asp Gly His Gly Glu Asn Ser Pro Tyr Phe Asp Gly
                20                  25                  30

Trp Lys Ala Tyr Asp Asn Asp Pro Phe His Pro Glu Asn Asn Pro Leu
            35                  40                  45

Gly Val Ile Gln Met Gly Leu Ala Glu Asn Gln Leu Ser Phe Asp Met
        50                  55                  60

Ile Val Asp Trp Ile Arg Lys His Pro Glu Ala Ser Ile Cys Thr Pro
 65                  70                  75                  80

Glu Gly Leu Glu Arg Phe Lys Ser Ile Ala Asn Phe Gln Asp Tyr His
                85                  90                  95

Gly Leu Pro Glu Phe Arg Asn Ala Ile Ala Asn Phe Met Gly Lys Val
            100                 105                 110

Arg Gly Gly Arg Val Lys Phe Asp Pro Ser Arg Ile Val Met Gly Gly
        115                 120                 125

Gly Ala Thr Gly Ala Ser Glu Thr Val Ile Phe Cys Leu Ala Asp Pro
130                 135                 140

Gly Asp Ala Phe Leu Val Pro Ser Pro Tyr Tyr Ala Gly Phe Asp Arg
145                 150                 155                 160

Asp Leu Lys Trp Arg Thr Arg Ala Gln Ile Ile Arg Val His Cys Asn
```

|     |     |     |     |     |     |     | 165 |     |     |     |     | 170 |     |     |     |     | 175 |     |     |
|-----|-----|-----|-----|-----|-----|-----|-----|-----|-----|-----|-----|-----|-----|-----|-----|-----|-----|-----|-----|

Gly Ser Asn Asn Phe Gln Val Thr Lys Ala Ala Leu Glu Ile Ala Tyr
                180                     185                     190

Lys Lys Ala Gln Glu Ala Asn Met Lys Val Lys Gly Val Ile Ile Thr
        195                     200                     205

Asn Pro Ser Asn Pro Leu Gly Thr Thr Tyr Asp Arg Asp Thr Leu Lys
    210                     215                     220

Thr Leu Val Thr Phe Val Asn Gln His Asp Ile His Leu Ile Cys Asp
225                     230                     235                 240

Glu Ile Tyr Ser Ala Thr Val Phe Lys Ala Pro Thr Phe Thr Ser Ile
                245                     250                     255

Ala Glu Ile Val Glu Gln Met Glu His Cys Lys Lys Glu Leu Ile His
                260                     265                     270

Ile Leu Tyr Ser Leu Ser Lys Asp Met Gly Leu Pro Gly Phe Arg Val
            275                     280                     285

Gly Ile Ile Tyr Ser Tyr Asn Asp Val Val Val Arg Arg Ala Arg Gln
    290                     295                     300

Met Ser Ser Phe Gly Leu Val Ser Ser Gln Thr Gln His Leu Leu Ala
305                     310                     315                 320

Ala Met Leu Ser Asp Glu Asp Phe Val Asp Lys Phe Leu Ala Glu Asn
                325                     330                     335

Ser Lys Arg Val Gly Glu Arg His Ala Arg Phe Thr Lys Glu Leu Asp
            340                     345                     350

Lys Met Gly Ile Thr Cys Leu Asn Ser Asn Ala Gly Val Phe Val Trp
        355                     360                     365

Met Asp Leu Arg Arg Leu Leu Lys Asp Gln Thr Phe Lys Ala Glu Met
    370                     375                     380

Glu Leu Trp Arg Val Ile Ile Asn Glu Val Lys Leu Asn Val Ser Pro
385                     390                     395                 400

Gly Ser Ser Phe His Val Thr Glu Pro Gly Trp Phe Arg Val Cys Phe
                405                     410                     415

Ala Asn Met Asp Asp Asn Thr Val Asp Val Ala Leu Asn Arg Ile His
            420                     425                     430

Ser Phe Val Glu Asn Ile Asp Lys Lys Glu Asp Asn Thr Val Ala Met
        435                     440                     445

Pro Ser Lys Thr Arg His Arg Asp Asn Lys Leu Arg Leu Ser Phe Ser
    450                     455                     460

Phe Ser Gly Arg Arg Tyr Asp Glu Gly Asn Val Leu Asn Ser Pro His
465                     470                     475                 480

Thr Met Ser Pro His Ser Pro Leu Val Ile Ala Lys Asn
                485                     490

( 2 ) INFORMATION FOR SEQ ID NO:20:

( i ) SEQUENCE CHARACTERISTICS:
        ( A ) LENGTH: 9060 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: join(2704..2880, 2968..3099, 3183..3344, 3810
            . . 4376, 4463..4903)

( x i ) SEQUENCE DESCRIPTION: SEQ ID NO:20:

CACATTGGTT GGAGAGAGAG GAACGAGTGC AACGAGGATG CTGGGCTCTG AAAAGGGGTG    60

| | | | | | |
|---|---|---|---|---|---|
| GATTGTGAGA | TCCCACGAAC | GAAACATTCT | TTGTAAGGGT | GTGAAAACCT | CTCCCTAGCA | 120 |
| TACTCGTTTT | AAAAACCTCA | AGGAGAAGTA | CAAAAGAAA | AGCCGAGGAA | GGATTTCAAA | 180 |
| AAGTTAGAAC | TTCATTAAAA | ATGAAAGCAC | AAGAAGAGA | ATTATTAGTA | ATGTTCTTGC | 240 |
| ACAAGTATAA | GTTGAAAAAC | TAATTCTATC | AAGTGTGAAT | CCACACTCAT | CTTTCAAAAT | 300 |
| TAAGCAAACA | AAACGAGTCA | TGCTTGCCTT | CTCCAAATTT | TATCACTAAT | AGTGTGACAC | 360 |
| TCAATGTCCC | ACTTACCATT | CTTGGCCCCC | ACAACCACCT | CCAAGAAACA | ATAACTTTTA | 420 |
| CTACCCAACC | CCCAATTTTG | GAACAAAAAT | GAGTCAAATA | TATGAACAAT | AACATCGTGT | 480 |
| TTCTTCTTAC | CGACTCGGTT | GAATATGCAA | CGTTTATAAT | ATACTTCAAG | AAATTTTGAG | 540 |
| ACATTACTCA | AATAAAGTCT | CTCACAAAAA | TAGAATATCT | TTATACTAGT | ATAATGAATT | 600 |
| GTCCACTTCG | ATTTAAATCC | TCTAAAGTTC | ACTTTCGTAA | ATGGCTTAAT | GAACAGATTT | 660 |
| ATTAGGATCA | AATTCAAAAG | TTGAATGAGA | CTAAATAGAT | ATAATAAAT | CTGATTGTTG | 720 |
| CATGAAGTAT | GCAGCTCAAA | GATGATGTTT | TGCGAAAAAA | ATGCAAACTA | AGCATGAGTG | 780 |
| CTTCTGTAAA | AAAAAAATGA | AAAAGAAAA | TATATATCGT | ACTATCAAA | ACATTGTCCT | 840 |
| TACTTAGACA | GCTCAAAACT | TTTCATATTC | CTATATTTGT | TTATATTGAA | ACTTTTTCCA | 900 |
| TTTCATTTGT | TTAAATCATA | TTTGGTTGTT | TAAATAAGAA | TACTGTAACA | GTCCAAGCTC | 960 |
| ACTGTTAGTA | GATATTGTCT | TCTTCGGACT | TTTCCGGCTT | CTTCTCAAGG | TTTTAAAATG | 1020 |
| TGTCTACTAG | GGAGAGATTT | TCACACACTT | ATAAAGAATG | ATTCGTTCTC | CTCTTCAACT | 1080 |
| AATGTAAAAT | CTCACAAATA | CTAAACAATT | GGAATTTATT | AGGATCAGAA | TCAAAAGTTG | 1140 |
| AGAGATATAG | TGGAAACGAC | CGTCGAGATT | AAATAGATAC | AATCAAGTTT | GATCATTGTA | 1200 |
| CTAAATAAGT | AGCTCGGAGA | TGTATACGAG | AAAAGAAAGC | GCACTATAAA | AATGAGGTAA | 1260 |
| AAAGTGGTCG | GAGTAGTATA | CAATGTGAGA | GGTATGCAAA | TATACGTATT | TCCTTTAGGT | 1320 |
| GAAAAAGTCC | GAAACCACAC | CAAAAAGCAC | TCTTAAAAAT | GTGCCAAAAC | GGTTCTATCA | 1380 |
| CTCAATGTCA | AATCTTTCAA | TTCAAAAGCA | TGTGGGTATT | GATTGCTGCT | TCCAACGAAG | 1440 |
| CTTCATTCTC | CTACTTGTTA | CACACACACA | AACTCGTTGT | TCATGACCAA | TTCTATCCCC | 1500 |
| TTTCCCATGT | CATCCTCCAA | ACTTTTGACC | CTTCAATTTG | GTCCCTAAC | CCTTTTTTC | 1560 |
| ATCACATGGG | ATGCAACCAT | TTGATTTAG | TCTACGACAT | TCTTTTCATT | TATCTACTTA | 1620 |
| CGCCCTCCGA | GGGAACAGTT | GGATTGAAAG | TTCGACTTCT | TAGCCTTGGA | GATGAGAGAA | 1680 |
| CCGGTACACT | CCATGAATTA | CAAAATTTAA | ATCTCTAATC | CTAACTTTGG | AGCTACGTAT | 1740 |
| GACCTTTGTA | TCTTTGTAAG | AGCTTTTCTC | AATGCTAACA | AATATTGTCT | ATTTCAGCTG | 1800 |
| GTTACGCATT | GTCGTCTGCT | TCCCGATTTT | AAAATACGTC | TATTAAGGAG | AGGTTTTCAC | 1860 |
| ACCCTTACTA | GAAACGTTTC | GTTCTCCCTC | TAAATGTGAG | ATCTCACCGT | AACTAGCTAG | 1920 |
| AGATTAAAAT | GTTATTATAG | CTAGAGATTC | AACCAAACAT | AACACAAAA | GATAATCATA | 1980 |
| GGGATCAACA | AAATTCATAA | CTAGTTCTTA | TAATATGCAA | TAAAATTCAA | ATTAATTATG | 2040 |
| CATTAGAAGA | AAATAAAAAA | ACAATTAAGA | TAACCCAAAA | ATTAATTTCC | TTCTACCTAT | 2100 |
| AAATCTATAA | TAAGATTCGA | GTATTAGATT | AAAATTATCC | CAAATCAAGA | ACATAAATTA | 2160 |
| AGATCATAAA | CGTAATATAT | TTAATCGAG | AACGTAAATA | CAGGACATAC | AGATTAAGAA | 2220 |
| TTCAAATATT | TTGAATTATA | ATATGAATTT | GATAGAAAAT | AAAACAAAAA | CTAAAAAATA | 2280 |
| AACTTAGTAA | TTATGATGAG | ATAAAAGAAG | ATTTTGTGAC | ATGATATTTT | TGTTATGTTC | 2340 |
| CAAATCTAGA | GTATGCCTCC | ACACATGCGG | GGTCGGGTCG | GCTGTGTGTG | TGGCTCGTCT | 2400 |
| GCTTGCTTGA | ATCACAACCC | TCCACGCATG | CAATTACGCC | CTCCTTGACT | CAAACCCCAT | 2460 |

```
TTTAACTCTC TCTTCCATTT TTATTATTTT TTCTTTAATT TTTTTCATCA CTGTTTTTTT          2520

TTTTTTTTTT TTTCATGGTT TGAACTTTGA AAAGTTGAAT TTTCTACACG TTTGATTTTC          2580

CTGGTAAGAA CTTGATCTTG TTGGATCTTC CTCACTGCTT ATAAATTCAC TCAATTCTCT          2640

TCTTTCTTTC CTATCTTACA ACCCAAAACC TCTCATTTTT AGGCACATCT CAACAACTTT          2700

CAA ATG GGG TTT CAT CAA ATC GAC GAA AGG AAC CAA GCT CTT CTC TCG            2748
    Met Gly Phe His Gln Ile Asp Glu Arg Asn Gln Ala Leu Leu Ser
    1               5                   10                  15

AAG ATC GCC CTC GAC GAT GGC CAT GGC GAG AAC TCC CCG TAT TTC GAT            2796
Lys Ile Ala Leu Asp Asp Gly His Gly Glu Asn Ser Pro Tyr Phe Asp
            20                  25                  30

GGG TGG AAA GCT TAC GAT AAC GAT CCG TTT CAC CCT GAG AAT AAT CCT            2844
Gly Trp Lys Ala Tyr Asp Asn Asp Pro Phe His Pro Glu Asn Asn Pro
        35                  40                  45

TTG GGT GTT ATT CAA ATG GGT TTA GCA GAA AAT CAG GTTGGTATA                  2890
Leu Gly Val Ile Gln Met Gly Leu Ala Glu Asn Gln
    50                  55

TCGTGTTTTC GTGTTTTTCT TATATGACTT CACGTTGAA AATTTCGCTA ACTTTGTTTT           2950

TTTGTGAATT TCGATAG CTT TCC TTT GAT ATG ATT GTT GAC TGG ATT AGA             3000
                    Leu Ser Phe Asp Met Ile Val Asp Trp Ile Arg
                    60                  65                  70

AAA CAC CCT GAA GCT TCG ATT TGT ACA CCG GAA GGA CTT GAG AGA TTC            3048
Lys His Pro Glu Ala Ser Ile Cys Thr Pro Glu Gly Leu Glu Arg Phe
            75                  80                  85

AAA AGC ATT GCC AAC TTC CAA GAT TAC CAC GGC TTA CCA GAG TTT CGA            3096
Lys Ser Ile Ala Asn Phe Gln Asp Tyr His Gly Leu Pro Glu Phe Arg
        90                  95                  100

AAT GTACGAGATA TGATATACTC TTAACTATAT CTGAACTCAA AAGGTTAAGT                 3149
Asn

TGATGGGTTA TGATAAAATT TCTTTCTTGT CAG GCA ATT GCA AAT TTT ATG GGG           3203
                                    Ala Ile Ala Asn Phe Met Gly
                                        105                 110

AAA GTA AGA GGT GGG AGG GTA AAA TTC GAC CCG AGT CGG ATT GTG ATG            3251
Lys Val Arg Gly Gly Arg Val Lys Phe Asp Pro Ser Arg Ile Val Met
            115                 120                 125

GGT GGC GGT GCG ACC GGA GCG AGC GAA ACC GTC ATC TTT TGT TTG GCG            3299
Gly Gly Gly Ala Thr Gly Ala Ser Glu Thr Val Ile Phe Cys Leu Ala
        130                 135                 140

GAT CCG GGG GAT GCT TTT TTG GTT CCT TCT CCA TAT TAT GCA GGG                3344
Asp Pro Gly Asp Ala Phe Leu Val Pro Ser Pro Tyr Tyr Ala Gly
    145                 150                 155

TGAGTTCTTC TTTCATTTCC TTTTGTTCAC TTTTCTTTAA GTCAATATTC CTTAGTCCAA          3404

CCTGGAAAGA GAAAGAAGAG AGAGAAAGAA ACCATTTGAC AAATTAATAA CTCTACAAAT          3464

TCTCTTTGAA AGTTTGATGT TTTTTTTAAG GTCAAAACTT CAACCATTCT CTTGCAAAGA          3524

AAAAAAAAAG TCATAATTAT AATGAAGAAA AAACTAGGCC ATCCAAGTCA ACCTTTTTAA          3584

ATGCTAATAA AGTCAATATG CTTTGTAGGT TTAAAAAACA ATAAATTGCT TAATCATTTC          3644

TTAAATTTTA ATTAAACCCT TTTGACTTTA TCATTACCCA TTTACATAAA TTAACAATTT          3704

ATTGCTCTTT TTGTAGTAAA ATTAATAAAA AAAAAGTTAG GTGTAAACGT ACAGTATTAT          3764

GTTATTGTAA AAATACTGAG AAGTGTTAGT ATGTTGTTTT TCAGA TTT GAT CGA              3818
                                                  Phe Asp Arg
                                                  160

GAC TTG AAA TGG CGA ACA CGA GCA CAA ATA ATT CGG GTC CAT TGC AAC            3866
Asp Leu Lys Trp Arg Thr Arg Ala Gln Ile Ile Arg Val His Cys Asn
            165                 170                 175

CGC TCG AAT AAC TTC CAA GTC ACA AAG GCA GCC TTA GAA ATA GCC TAC            3914
```

|   |   |   |   |   |   |   |   |   |   |   |   |   |   |   |
|---|---|---|---|---|---|---|---|---|---|---|---|---|---|---|
| Arg | Ser | Asn | Asn<br>180 | Phe | Gln | Val | Thr | Lys<br>185 | Ala | Ala | Leu | Glu | Ile<br>190 | Ala | Tyr |

| AAA | AAG | GCT | CAA | GAG | GCC | AAC | ATG | AAA | GTG | AAG | GGT | GTT | ATA | ATC | ACC | 3962 |
|---|---|---|---|---|---|---|---|---|---|---|---|---|---|---|---|---|
| Lys | Lys | Ala<br>195 | Gln | Glu | Ala | Asn | Met<br>200 | Lys | Val | Lys | Gly | Val<br>205 | Ile | Ile | Thr |  |

| AAT | CCC | TCA | AAT | CCC | TTA | GGC | ACA | ACG | TAC | GAC | CGT | GAC | ACT | CTT | AAA | 4010 |
|---|---|---|---|---|---|---|---|---|---|---|---|---|---|---|---|---|
| Asn | Pro<br>210 | Ser | Asn | Pro | Leu | Gly<br>215 | Thr | Thr | Tyr | Asp | Arg<br>220 | Asp | Thr | Leu | Lys |  |

| ACC | CTC | GTC | ACC | TTT | GTG | AAT | CAA | CAC | GAC | ATT | CAC | TTA | ATA | TGC | GAT | 4058 |
|---|---|---|---|---|---|---|---|---|---|---|---|---|---|---|---|---|
| Thr<br>225 | Leu | Val | Thr | Phe | Val<br>230 | Asn | Gln | His | Asp | Ile<br>235 | His | Leu | Ile | Cys | Asp<br>240 |  |

| GAA | ATA | TAC | TCT | GCC | ACT | GTC | TTC | AAA | GCC | CCA | ACC | TTC | ACC | AGC | ATC | 4106 |
|---|---|---|---|---|---|---|---|---|---|---|---|---|---|---|---|---|
| Glu | Ile | Tyr | Ser | Ala<br>245 | Thr | Val | Phe | Lys | Ala<br>250 | Pro | Thr | Phe | Thr | Ser<br>255 | Ile |  |

| GCT | GAG | ATT | GTT | GAA | CAA | ATG | GAG | CAT | TGC | AAG | AAG | GAG | CTC | ATC | CAT | 4154 |
|---|---|---|---|---|---|---|---|---|---|---|---|---|---|---|---|---|
| Ala | Glu | Ile | Val<br>260 | Glu | Gln | Met | Glu | His<br>265 | Cys | Lys | Lys | Glu | Leu<br>270 | Ile | His |  |

| ATT | CTT | TAT | AGC | TTG | TCC | AAA | GAC | ATG | GGC | CTC | CCT | GGT | TTT | CGA | GTT | 4202 |
|---|---|---|---|---|---|---|---|---|---|---|---|---|---|---|---|---|
| Ile | Leu | Tyr | Ser<br>275 | Leu | Ser | Lys | Asp | Met<br>280 | Gly | Leu | Pro | Gly | Phe<br>285 | Arg | Val |  |

| GGA | ATT | ATT | TAT | TCT | TAC | AAC | GAT | GTC | GTC | GTC | CGC | CGT | GCT | CGG | CAG | 4250 |
|---|---|---|---|---|---|---|---|---|---|---|---|---|---|---|---|---|
| Gly | Ile<br>290 | Ile | Tyr | Ser | Tyr | Asn<br>295 | Asp | Val | Val | Val | Arg<br>300 | Arg | Ala | Arg | Gln |  |

| ATG | TCG | AGC | TTC | GGC | CTC | GTC | TCG | TCC | CAG | ACT | CAA | CAT | TTG | CTC | GCC | 4298 |
|---|---|---|---|---|---|---|---|---|---|---|---|---|---|---|---|---|
| Met<br>305 | Ser | Ser | Phe | Gly | Leu<br>310 | Val | Ser | Ser | Gln | Thr<br>315 | Gln | His | Leu | Leu | Ala<br>320 |  |

| GCC | ATG | CTT | TCC | GAC | GAG | GAC | TTT | GTC | GAC | AAA | TTT | CTT | GCC | GAG | AAC | 4346 |
|---|---|---|---|---|---|---|---|---|---|---|---|---|---|---|---|---|
| Ala | Met | Leu | Ser | Asp<br>325 | Glu | Asp | Phe | Val | Asp<br>330 | Lys | Phe | Leu | Ala | Glu<br>335 | Asn |  |

| TCG | AAG | CGT | GTG | GGC | GAG | AGG | CAT | GCA | AGG | TTTGTTAAAC | TACACCATTA | 4396 |
|---|---|---|---|---|---|---|---|---|---|---|---|---|
| Ser | Lys | Arg | Val<br>340 | Gly | Glu | Arg | His | Ala<br>345 | Arg |  |  |  |

| TTATTTGTGG | GATTGAAAAG | CATTACTTTT | TGCAATTAAT | TTAAGAATGT | ATTAATCAAA | 4456 |
|---|---|---|---|---|---|---|

| TTCAGG | TTC | ACA | AAA | GAA | TTG | GAT | AAA | ATG | GGG | ATC | ACT | TGC | TTG | AAC | 4504 |
|---|---|---|---|---|---|---|---|---|---|---|---|---|---|---|---|
|  | Phe | Thr | Lys | Glu<br>350 | Leu | Asp | Lys | Met | Gly<br>355 | Ile | Thr | Cys | Leu | Asn<br>360 |  |

| AGC | AAT | GCT | GGA | GTT | TTT | GTG | TGG | ATG | GAT | CTA | CGG | AGG | CTA | TTA | AAA | 4552 |
|---|---|---|---|---|---|---|---|---|---|---|---|---|---|---|---|---|
| Ser | Asn | Ala | Gly | Val<br>365 | Phe | Val | Trp | Met | Asp<br>370 | Leu | Arg | Arg | Leu | Leu<br>375 | Lys |  |

| GAC | CAA | ACC | TTC | AAA | GCT | GAA | ATG | GAG | CTT | TGG | CGT | GTG | ATT | ATC | AAT | 4600 |
|---|---|---|---|---|---|---|---|---|---|---|---|---|---|---|---|---|
| Asp | Gln | Thr | Phe<br>380 | Lys | Ala | Glu | Met | Glu<br>385 | Leu | Trp | Arg | Val | Ile<br>390 | Ile | Asn |  |

| GAA | GTC | AAG | CTC | AAT | GTT | TCT | CCT | GGC | TCA | TCC | TTT | CAT | GTC | ACT | GAG | 4648 |
|---|---|---|---|---|---|---|---|---|---|---|---|---|---|---|---|---|
| Glu | Val | Lys<br>395 | Leu | Asn | Val | Ser | Pro<br>400 | Gly | Ser | Ser | Phe | His<br>405 | Val | Thr | Glu |  |

| CCA | GGT | TGG | TTT | CGA | GTT | TGT | TTC | GCA | AAC | ATG | GAC | GAC | AAC | ACC | GTT | 4696 |
|---|---|---|---|---|---|---|---|---|---|---|---|---|---|---|---|---|
| Pro | Gly<br>410 | Trp | Phe | Arg | Val | Cys<br>415 | Phe | Ala | Asn | Met | Asp<br>420 | Asp | Asn | Thr | Val |  |

| GAC | GTT | GCT | CTC | AAT | AGA | ATC | CAT | AGC | TTT | GTC | GAA | AAC | ATC | GAC | AAG | 4744 |
|---|---|---|---|---|---|---|---|---|---|---|---|---|---|---|---|---|
| Asp<br>425 | Val | Ala | Leu | Asn | Arg<br>430 | Ile | His | Ser | Phe | Val<br>435 | Glu | Asn | Ile | Asp | Lys<br>440 |  |

| AAG | GAA | GAC | AAT | ACC | GTT | GCA | ATG | CCA | TCG | AAA | ACG | AGG | CAT | CGA | GAT | 4792 |
|---|---|---|---|---|---|---|---|---|---|---|---|---|---|---|---|---|
| Lys | Glu | Asp | Asn | Thr<br>445 | Val | Ala | Met | Pro | Ser<br>450 | Lys | Thr | Arg | His | Arg<br>455 | Asp |  |

| AAT | AAG | TTA | CGA | TTG | AGC | TTC | TCC | TTC | TCA | GGG | AGA | AGA | TAC | GAC | GAG | 4840 |
|---|---|---|---|---|---|---|---|---|---|---|---|---|---|---|---|---|
| Asn | Lys | Leu | Arg<br>460 | Leu | Ser | Phe | Ser | Phe<br>465 | Ser | Gly | Arg | Arg | Tyr<br>470 | Asp | Glu |  |

| GGC | AAC | GTT | CTT | AAC | TCA | CCG | CAC | ACG | ATG | TCG | CCT | CAC | TCG | CCG | TTA | 4888 |
|---|---|---|---|---|---|---|---|---|---|---|---|---|---|---|---|---|
| Gly | Asn | Val<br>475 | Leu | Asn | Ser | Pro | His<br>480 | Thr | Met | Ser | Pro | His<br>485 | Ser | Pro | Leu |  |

```
GTA ATA GCA AAA AAT TAATTAAAAA CATTTTTCAA AATATTCATA CCATTCATAT         4943
Val Ile Ala Lys Asn
        490

AGTTTTTTTT TTTTTTTTT TTTGGGTCAA TGTTGACTAA AGTTACGTAT ATTTTTTCCA        5003
CAGTGGATAT GATGTAAACT TCATATTTTT TGGTGGGATG GTGATAGATG TAATGTATTT        5063
GGTTTTTCCC TTAGGGAACT CATACTTATT TATTAATGAA ATGATTGTGA TTTATGAATT        5123
ATAATTGTAT ATTTTTCTTT AAAAGTATTT TATTGCAAAA ATAAATAAGT ATTATGAGGA        5183
ATTGTAATTG AATGGAAAAG GTATAGAGTC AAAGGGAATA AACATATATT TTATTTTTTC        5243
TTATGGAAGT TTGTTCATA CTTAAAATGT ATTATATTTA TGGAAACTTT ATTGACTTTA        5303
AAGATTTGGG ACAAAGGGTA TGATATGTTC AAGTTTATTA CGTTGTTGG ATTAGTCACT        5363
TCATTGACAT TGATGTTTTT GTTGTCATAT TTTGTCATTA TTACCACACT TTTTTGTCT        5423
AAAAGCAAGC TTATATTCAA TGAGGATGCA AAAATACTTT ATAAATGGTT TGTCTATGTT       5483
TGGGTCTCAT AGATGCACCT TTATACAAAA CCGTTCATAC AAACAACCAA ATTATATATG       5543
TCGATCCAGA AACGCTATAT ACAAAGTCAA ATACTTTACT GACAAACTAC GATCGTTCAC       5603
CGTCCTATAA CATCTTTTTC GAGTCTAACC ATTCAATGTT ACATCGTTTT TTTTTTTGT        5663
TTGGTAAATA CTTTTTCTTT TTGCTTTGTT AAATTATAAC TTGGGTTTGT TATGTGCAAT       5723
TTATCTATTT ATATGCAGTT GACTTAGTTA GCTTGTATTG TTCTAGTAGT GAATGACTAG       5783
TATCTTGAGT TGAGGGGCTA CCTCATAAAA TCTAGTAGGA CGACATGATA GCGTGGATCT       5843
GAATATTATT TATGGAAGGT TAATTAACAT ACTCTTCTAC AAGACCATAA AGTCATACTA       5903
AATTTGGGGG AGTGACCTCG TGTACTTGCC AGCTAGTAAG TTACGTGTAT GGTCCCTCAC       5963
CCTCCCTCAC CCTCTAGTCA TTTCGACTAG ATAAAGACAC ATGGTTGCCT TGACGTGATA       6023
TATTATTTGG CCCAGGCCAA ACTTGATGGT ACAACTGTTG TGCTCCTACC ACTAAAATAA       6083
CTGATCTAGG TCACACATGG CTATTAGGTT TGTTAAGCTT CTTAATCAT CCTTGGATGC        6143
TTCGAGGTTT ATTAGGTTTT CAGGATGTCT AGATTGTTTA AATCTCGAAC TCTCATTTCT       6203
AGGAACTCTG GACTGCACCT CTAGGCTAAT CTAGTTTATA GGAGCACTAT GGTCCTGACC       6263
ACTGATCTTC ACTCACGATC CTAGGGTACT CGTTCTAGAA TGGGTGTTAG AGTTAGAACA       6323
GTTTCACGTT GACCTAGGTC AGAACGTTTT CATTAGACCG AACACGCTAA GATCGTGAGC       6383
GACAATCAAT GGTCAAGATT ATAGTGCTCC TATAAACTAG ATTAGTCCCA AGGTGCAGTC       6443
CATTGTGCAT AGAAATGAGA GTTGGAGATT TAAACAACCT AGATGTCCTA AAACCTAGTA       6503
AACCTCGAAG GCATCCAATG ATGACTAAGA AATCTTAACA AGGCTATTAG CAGTGTGAAC       6563
GGTGTCATGA GAGCATTTGC CTCCTATCTT CTTCGGTACG TCATTAGCTC TATCAATGAC       6623
CTAGGTCAGT TCTTTTAGTG GCGTGTCAAG TGGTAGGAGC ACAAGAGTTG TACCATCAAG       6683
CTTGGCCTAG GCCAAATAGT ATAGCACGTC GAGGAAACCA TGTGTCTTTA TCCAGTCAAA       6743
ATGACTAGGG GACTTCTAAA AAAGGTCTCT GCACCATAAA CTGATCCCGA GAGAGGGTGA       6803
GGGACCATAC AGGTAACTTA GTAGCTGACA AGCACACGAG GTCGCTCCCC CAAATTTAGT       6863
GACTTTATGG TCGTGGAGAA GAGTATGTTA GTTAACCTTC CATAAATAAT GTTCACATCC       6923
ACGATATCAT ACGGTCGTAT TAGATTTTAT CACTATTGTG TTTGTATGCA TGGTTTTGCA       6983
TAAAGGTAGA TCTGTAGCAG ACAGTTTGCG TATTGGAATG GCACCGCCAT TGTTAAGAAG       7043
GTGGACACCG TGTGGCCGAA CTCTGATATG AACAAAATGA AGACAAGACA AGTGGACATA       7103
TATAATCCCA TGAACCAGGT TTGGACGTAA AACAATATAA TGCCTGTCGT TTTCAGCTGC       7163
CCATTTCGAC AAACACTCAT CTCCATTGTC CAGTGGGTTC TCCTTATATT CAACAAAAAT       7223
```

-continued

```
TTGTTTGAAT GTTTAAAGAT AAAAATTTGA CTTTTAAACC AAAACCGTGA TAACTTAGGA      7283
TGGTGTGATA ATATTTAAGT CCCAATTTTC ATTTGAATTT TAAAATTGTT TGAAAAAAAC      7343
ATATATATTT TTTATTAAAA TAAAAGATGA AGGTTGACAT CGAAATCTTA CGAGATAATC      7403
CTTATCGGCG TTCTAACGAA ATTAATACTA TCATGGTCTT ATTCTAAAAG TCTATGTCTT      7463
TTATGTATTG TTTAATCAAA TATGAATTAC TTGGAAAATG GGATCTTGTG TGTTTGACTT      7523
GAGTTTGAAC AATTGTCAAA ATGTTAGCTG TAAAGTAGTC GCCCTTCTCA TCCATTTAGT      7583
TTAAAGGATG TTTCGAGTTT AAATTTTCTT CTCTCACTCC AAGGGAGAAT CATCTATGTC      7643
ATTATATATG CAAGGGTGGT TTGATTATGA TAGATAGATG TACATTTAAC CTGTTAAGTA      7703
GGGGTCATGC GGATCAGAGA TCTACTTTAA ATGGCGTAGA AAATCCTGTT TAAACAGGGT      7763
CGGGAATAAG GATTATCATA CTCTACCCTG CTCACTTCTT ATGTATAAAT ATAGATAGAA      7823
TAAATGAGAA ATTTTATGGA ATGAAAATT GAAGTAGGAG GAAGGCGCAG GGACGGGTAA        7883
GACTTCCCCG TTCTCACGCT TCCCCATAAA CATCATACTT CAACTTTGAT GAAGTATGAA      7943
ATTTGTTTG GTGGATATCC AATAAGTCTC ATTGCACTAA ACAAAGCCAG GGAAGAGTTC      8003
ATAAATAAGA CGTAAAGTTG TGGTCTCCAA CACGTAAAAC ATAGTTACTC CTCTTGATTT      8063
CCCATGTAAT TGAGAATTTA GAGCTTTAGT GTGTTTAGAC GAGGAAGATT GCTTTCACTG      8123
AACACTGAGT TGTTCCCTAA ATCTATTTGT TACAACGAGG TTTATCACTG CTTAAGTGAT      8183
GTAATTTAGG TTTTAATTTC TAGAAAACGT GACTATGTGT AATGTCAGAC TTGTTAGGAC      8243
TTTGAGCATA AGCTCTCATG TCTTTGATTT GAACTTTCTT AAAAAGTTTC ATACCAATGG      8303
AGATGTATTC CTCGTTTATA AACTCAAGAT CATTCGCTAA CGTGGGACTT CCTTCCGATA      8363
ATCCTCAACA AAACTCAGTA TTAACTTCAG TTTGTTTGGT GAAGTGTTAG ACCCTTTCTT      8423
TAATCACATG CAATCATGGT GAGATTTGTC TTTTCATAAA AATATTATGG CCTTATATTC      8483
TATTTCCAGT CTGAACAGAG TTGAATGAGT TGTACTTCTC TACAATCAGC CCATGCACAC      8543
ATACGAGAAC CCACCAGACG GACTCATGTC TAAACAAAAG GGAAGAATCA CATTAGAGGG      8603
TGAAGAAGAA ACATTTTACA CAAGTGCTCG GAGCAACAAT ACGTCATTTA CCAAACATGG      8663
ATATAAAAAT GGTGACAAAG GAAGAAGCTA TCAAGCACAA TCAGGGAGAG CTCAGAAGAA      8723
CGACAACAAT AACTCTCAAG TGAAGAGATT TTGGGGTATT TACTACAACT GCGGAAAAAG      8783
GGCTACATGT CCAGAGATGG TTGGTCTAAG AAAATTTTTG TTGAAAGCAA TGTGGCAACA      8843
TCCAAAAAGG AGATGGAAGA TAAATGGGAT GCAGAGGCAA TATGTGTCGT AGAAGAAGAC      8903
GAGCTAGCAC TTATGGTAAT AAAGAGAGAA CATATTGATT ATGAGGATGA CTGAATCATT      8963
GATTCAGGAT GCTTAAACCA CATGATTAAC AATCAGAGTG GAACAATTGG ATGCGGAGTG      9023
GCCCTCAGAG AATGAAGTAT TTCAAGGCTT GGAATTC                               9060
```

( 2 ) INFORMATION FOR SEQ ID NO:21:

( i ) SEQUENCE CHARACTERISTICS:
        ( A ) LENGTH: 493 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Met Gly Phe His Gln Ile Asp Glu Arg Asn Gln Ala Leu Leu Ser Lys
 1               5                  10                  15

Ile Ala Leu Asp Asp Gly His Gly Glu Asn Ser Pro Tyr Phe Asp Gly
            20                  25                  30
```

```
Trp Lys Ala Tyr Asp Asn Asp Pro Phe His Pro Glu Asn Asn Pro Leu
        35              40                  45
Gly Val Ile Gln Met Gly Leu Ala Glu Asn Gln Leu Ser Phe Asp Met
        50              55                  60
Ile Val Asp Trp Ile Arg Lys His Pro Glu Ala Ser Ile Cys Thr Pro
65                      70                  75                  80
Glu Gly Leu Glu Arg Phe Lys Ser Ile Ala Asn Phe Gln Asp Tyr His
                85                  90                      95
Gly Leu Pro Glu Phe Arg Asn Ala Ile Ala Asn Phe Met Gly Lys Val
            100                 105                 110
Arg Gly Gly Arg Val Lys Phe Asp Pro Ser Arg Ile Val Met Gly Gly
        115                 120                 125
Gly Ala Thr Gly Ala Ser Glu Thr Val Ile Phe Cys Leu Ala Asp Pro
    130                 135                 140
Gly Asp Ala Phe Leu Val Pro Ser Pro Tyr Tyr Ala Gly Phe Asp Arg
145                 150                 155                 160
Asp Leu Lys Trp Arg Thr Arg Ala Gln Ile Ile Arg Val His Cys Asn
                165                 170                 175
Arg Ser Asn Asn Phe Gln Val Thr Lys Ala Ala Leu Glu Ile Ala Tyr
            180                 185                 190
Lys Lys Ala Gln Glu Ala Asn Met Lys Val Lys Gly Val Ile Ile Thr
        195                 200                 205
Asn Pro Ser Asn Pro Leu Gly Thr Thr Tyr Asp Arg Asp Thr Leu Lys
    210                 215                 220
Thr Leu Val Thr Phe Val Asn Gln His Asp Ile His Leu Ile Cys Asp
225                 230                 235                 240
Glu Ile Tyr Ser Ala Thr Val Phe Lys Ala Pro Thr Phe Thr Ser Ile
                245                 250                 255
Ala Glu Ile Val Glu Gln Met Glu His Cys Lys Lys Glu Leu Ile His
            260                 265                 270
Ile Leu Tyr Ser Leu Ser Lys Asp Met Gly Leu Pro Gly Phe Arg Val
        275                 280                 285
Gly Ile Ile Tyr Ser Tyr Asn Asp Val Val Val Arg Arg Ala Arg Gln
    290                 295                 300
Met Ser Ser Phe Gly Leu Val Ser Ser Gln Thr Gln His Leu Leu Ala
305                 310                 315                 320
Ala Met Leu Ser Asp Glu Asp Phe Val Asp Lys Phe Leu Ala Glu Asn
                325                 330                 335
Ser Lys Arg Val Gly Glu Arg His Ala Arg Phe Thr Lys Glu Leu Asp
            340                 345                 350
Lys Met Gly Ile Thr Cys Leu Asn Ser Asn Ala Gly Val Phe Val Trp
        355                 360                 365
Met Asp Leu Arg Arg Leu Leu Lys Asp Gln Thr Phe Lys Ala Glu Met
    370                 375                 380
Glu Leu Trp Arg Val Ile Ile Asn Glu Val Lys Leu Asn Val Ser Pro
385                 390                 395                 400
Gly Ser Ser Phe His Val Thr Glu Pro Gly Trp Phe Arg Val Cys Phe
                405                 410                 415
Ala Asn Met Asp Asp Asn Thr Val Asp Val Ala Leu Asn Arg Ile His
            420                 425                 430
Ser Phe Val Glu Asn Ile Asp Lys Lys Glu Asp Asn Thr Val Ala Met
        435                 440                 445
Pro Ser Lys Thr Arg His Arg Asp Asn Lys Leu Arg Leu Ser Phe Ser
```

|     |     |     |     | 450 |     |     |     |     | 455 |     |     |     | 460 |     |
| --- | --- | --- | --- | --- | --- | --- | --- | --- | --- | --- | --- | --- | --- | --- |
| Phe | Ser | Gly | Arg | Arg | Tyr | Asp | Glu | Gly | Asn | Val | Leu | Asn | Ser | Pro | His |
| 465 |     |     |     |     | 470 |     |     |     | 475 |     |     |     |     | 480 |
| Thr | Met | Ser | Pro | His | Ser | Pro | Leu | Val | Ile | Ala | Lys | Asn |
|     |     |     | 485 |     |     |     |     | 490 |

( 2 ) INFORMATION FOR SEQ ID NO:22:

( i ) SEQUENCE CHARACTERISTICS:
        ( A ) LENGTH: 7587 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: join(2637..2813, 2901..3032, 3120..3281, 4540
            . . 5106, 5193..5636)

( x i ) SEQUENCE DESCRIPTION: SEQ ID NO:22:

| | | | | | |
|---|---|---|---|---|---|
| AAGCTTAATG | ACTACGAATC | AAGCTACTTA | TCATCCATTA | ATCATTAAT | ATACCTCAAT | 60 |
| ACGTCTAACT | CAATCATGTT | CTCATCATAT | TTTGACGTT | TAACTGTTCG | TGGGTTGGAT | 120 |
| TGGGTTGAAT | TGAAACGGTT | CTTAGATCTA | ACTAAATTGT | TCGAGTTTCA | ACTTTGATTA | 180 |
| AATAATGAAC | TCAACTCAAC | CCAACCGAAT | CATAAAGTTT | TGGATTGAAC | TTGTTTGGGT | 240 |
| AACCTAATTC | TATACAAGCA | AGTTCGTAAT | CCAAATGAAA | CTATATATAT | TGAGTTAAGC | 300 |
| TGATCGAATT | TTTCGAATTC | AAATTTTGTT | GATTATCTTC | TCATTGTTCT | ATCAACCTTT | 360 |
| GTATAGTTCT | TTGTCACAAA | AACAAATCCT | CACCGACCAT | ACTATTAATT | GTGATCTAAC | 420 |
| GTAAAAAAAA | CGTTTGTTTA | TGTAACACTT | TAATGATCAT | ATTTCTAGAT | TCACTAAAAA | 480 |
| GATCATGTAC | AAACAAAATA | GTCGATCACA | AAGACTATAT | TCAGAAGCCA | ATTTTTATTT | 540 |
| TAATTCGACT | CGTTTTGAAT | CTGTGTTTTT | TTTTTTTTT | TTTGAATCT | AGACGAAGAA | 600 |
| TAACAAAAAT | CTCTCCAAAA | TTCGATCTCC | ATTGACTTTT | TGGTACCGAT | CCATTAATGA | 660 |
| ACGTGGGTTT | GATTTTAGAA | GCCCTATTGA | ATTTTCTTGT | TTGAATTTAT | TAATCTTCTT | 720 |
| TGATTGCGAT | TGACCAATTG | ATTTGGTTGA | GACTCAAAAT | CCCAAAACAT | ACAAAAGTCT | 780 |
| TAATGTAACA | ACGAACTCAT | GAACATATCG | TTAATGCATA | CATATCACAA | AAGCGTTTCA | 840 |
| ACACATTTGA | GTAAAAGTGA | CGAAAAGCTG | AACTTTTTA | AAACAAACTT | CGAACCTTTT | 900 |
| AACTTTTTAT | ATGAATTGAA | CATAACAACA | AAATGTTAAC | ATTGTATTGA | CATCATTATA | 960 |
| TTTAACAATT | TTCCACCGAC | CATACTACTA | ATTGTACTCT | TAAATGGAAG | TTCTTATTTT | 1020 |
| CGTTCTCAAA | TATTCTAATC | GTTTTTATTC | ATTCATCGTT | CAACAGCTAC | TCTTATGCAT | 1080 |
| TATTTTCTTC | CGTTTATCAA | TTTACATTTC | TAGATCCACT | AAAAGTTCAT | AAACAAACAA | 1140 |
| AATAGTCGAT | CCCAGTCGAT | CCCACCGACC | ATCTTCCTAT | AGAAGCCAAT | TTTTATTTTA | 1200 |
| ATTCGACTCA | TTTTGAAATT | ATGTTATTTC | CCCAAAATTC | ATCTCCTTCA | ACTTTTTGGT | 1260 |
| GCCAATCCAT | TAATGAACGT | GAGGTTGGTT | TAGAAGTCCA | TTGGGTTTTG | TTGTATGATT | 1320 |
| TAATTATTTT | CTTTGCCAAC | TTTTTCGTGG | TCAAGCCCAT | CGATTTAAAT | ATTTATTATT | 1380 |
| TGTTTCTTAT | CATTTTCTTA | TCGGCTAATA | CGATAGTTTT | CTATTTGAGC | GAGAAAAAGC | 1440 |
| GTGCTAGGAG | ATTCATATTG | GTTTGTGGGA | TTGTCTAAAC | GTGACCATTT | GTAGGAGATG | 1500 |
| CAAGGGAATA | ATGAGACATA | CATGTGCTGA | ATTCAGATTC | AGAATTGTTT | CAAATTCCGA | 1560 |
| GCATGGATAC | TTCGTAAAAG | TTGAAAAACC | ATGCACACCT | CGAACGAGTG | AACAATAATA | 1620 |
| TTGCCTTTCT | TTCGCCCCCA | TACTCAAGAA | AGCTTGGGAC | GCTACATAAG | AAGTTAAATT | 1680 |

-continued

| | | | | |
|---|---|---|---|---|
| AGGTATCATT | GAAATAGGAT | ATATTTGTAC | TTGTATGATG | TATTGTCATA CTTCTCGACT | 1740 |
| TCATCTAATT | ATAGAGTTTC | GAAGTTTTCA | TACTTTCCCA | TTTTGTTGA AAATGTATTA | 1800 |
| TTGCACGAGT | GCAGTTGGAT | TAAACATCTG | AACCCCAACG | AGAATTAATT TTCTCGAATT | 1860 |
| TTTCATTTAC | GATCAAGCTT | CCAGAATTTT | ATTGAAAACC | TTAGAGATCG AATTTAGGAA | 1920 |
| TACAGTAGAA | GAGAATGATG | CTCGGAATGT | TTTCTAGAAG | CTCGAAAAAA TATAAAATAA | 1980 |
| AATCGTAGAA | AATAAAAAAA | TGTGTGGTCA | AAGTCAATAG | AATTTGCCC CTCCTAGTAT | 2040 |
| TTTGGAGACC | CTCGAAAAAC | CCGAGTGAAT | GATCATTTTA | GGTTTCGGTT TTCCTCAAAA | 2100 |
| TCTAAAGTGT | ATGAAGAAAT | TAGCATATGA | AAATTTAGTA | TGTTGATCTT GTCATGATTT | 2160 |
| CGCACATTTT | TCTTAAAAGA | ACCTGAAGTC | AAATCATAAC | GGAACTAGGA GATCGAAGAA | 2220 |
| GACCCAAGAA | CGGTATAAAC | ACATAAATAT | GAAGGTTTTG | AGAGGGACG AAAGACTACA | 2280 |
| TAAGTAGTAT | ATTGAGGAGC | TATTATTGTG | TATGGAGGAA | GCCCACTCTG AGAGGAGATG | 2340 |
| AGAGACTACA | AAAGTAGATC | AGCTGTGTCT | CGAAGCCTAA | AAATTGGGT TGTGACATTG | 2400 |
| AAAGTTCGAT | TTTTCCTAAG | GTGACATAAG | GGGATCTATA | ACATCGTACT CTTTGTTTTG | 2460 |
| TTCCAATTTC | CTACACACAC | GACTTGGTCG | GCTGTTTGTG | GCTTGTCTTT TTACATGGTT | 2520 |
| TCAACGTGAC | CCTGGGCTTA | TAAATTCACT | CCCATTTTGT | TCTTTCTTTC GTATCTTAAC | 2580 |
| AACCCAAAAG | CTCTCATTTT | TAGGGACACA | AAAACAAACA | CCTCAACAAC TTCAA | 2636 |

| | | | | | | | | | | | | | | | | |
|---|---|---|---|---|---|---|---|---|---|---|---|---|---|---|---|---|
| ATG | GGG | TTT | CAT | CAA | ATT | GAC | GAA | AGG | AAC | CAA | GCT | CTT | CTC | TCT | AAG | 2684 |
| Met | Gly | Phe | His | Gln | Ile | Asp | Glu | Arg | Asn | Gln | Ala | Leu | Leu | Ser | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ATC | GCT | ATC | GAC | GAT | GGC | CAT | GGC | GAG | AAC | TCA | GCC | TAT | TTC | GAT | GGG | 2732 |
| Ile | Ala | Ile | Asp | Asp | Gly | His | Gly | Glu | Asn | Ser | Ala | Tyr | Phe | Asp | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| TGG | AAA | GCT | TAT | GAT | AAC | AAT | CCG | TTT | CAC | CCC | GAG | AAT | AAT | CCT | TTG | 2780 |
| Trp | Lys | Ala | Tyr | Asp | Asn | Asn | Pro | Phe | His | Pro | Glu | Asn | Asn | Pro | Leu | |
| | | 35 | | | | | 40 | | | | | 45 | | | | |

| | | | | | | | | | | |
|---|---|---|---|---|---|---|---|---|---|---|
| GGT | GTT | ATT | CAA | ATG | GGT | TTA | GCA | GAA | AAT | CAA | GTTCGTATA TAGTGTTTTC | 2833 |
| Gly | Val | Ile | Gln | Met | Gly | Leu | Ala | Glu | Asn | Gln | | |
| | 50 | | | | | 55 | | | | | | |

| | | | | | |
|---|---|---|---|---|---|
| ATGTTTTTCT | TATATCATTT | CACGTTTGAA | AATTTCGCTA | ACTTGTTTC TGTGTGAATT | 2893 |

| | | | | | | | | | | | | | | |
|---|---|---|---|---|---|---|---|---|---|---|---|---|---|---|
| TCGATAG | CTT | TCT | TTT | GGT | ATG | ATT | GTT | GAC | TGG | ATT | AGA | AAA | CAC CCC | 2942 |
| | Leu | Ser | Phe | Gly | Met | Ile | Val | Asp | Trp | Ile | Arg | Lys | His Pro | |
| | | 60 | | | | | 65 | | | | | 70 | | |

| | | | | | | | | | | | | | | | |
|---|---|---|---|---|---|---|---|---|---|---|---|---|---|---|---|
| GAA | GCT | TCG | ATT | TGT | ACA | CCT | GAA | GGA | CTT | GAG | AAA | TTC | AAA | AGC ATT | 2990 |
| Glu | Ala | Ser | Ile | Cys | Thr | Pro | Glu | Gly | Leu | Glu | Lys | Phe | Lys | Ser Ile | |
| | | 75 | | | | | 80 | | | | | 85 | | | |

| | | | | | | | | | | | | |
|---|---|---|---|---|---|---|---|---|---|---|---|---|
| GCC | AAC | TTT | CAA | GAT | TAT | CAT | GGC | TTA | CAA | GAG | TTT CGA AAA | 3032 |
| Ala | Asn | Phe | Gln | Asp | Tyr | His | Gly | Leu | Gln | Glu | Phe Arg Lys | |
| 90 | | | | | 95 | | | | | 100 | | |

| | | | | | |
|---|---|---|---|---|---|
| GTACTAGATA | TGATATTCTA | ACTATATCTA | AACTCAGAAG | CTTAAGTCGA TGGATTATGA | 3092 |

| | | | | | | | | | |
|---|---|---|---|---|---|---|---|---|---|
| TATATATATA | TATATTTTAT | TTTTCAG GCG | ATG | GCG | AGT | TTC | ATG | GGG AAG | 3143 |
| | | Ala | Met | Ala | Ser | Phe | Met | Gly Lys | |
| | | | | 105 | | | | 110 | |

| | | | | | | | | | | | | | | | |
|---|---|---|---|---|---|---|---|---|---|---|---|---|---|---|---|
| GTA | AGG | GGT | GGG | AGG | GTG | AAA | TTC | GAC | CCG | AGT | CGG | ATT | GTG | ATG GGT | 3191 |
| Val | Arg | Gly | Gly | Arg | Val | Lys | Phe | Asp | Pro | Ser | Arg | Ile | Val | Met Gly | |
| | | | 115 | | | | | 120 | | | | | 125 | | |

| | | | | | | | | | | | | | | | |
|---|---|---|---|---|---|---|---|---|---|---|---|---|---|---|---|
| GGC | GGT | GCG | ACC | GGA | GCG | AGC | GAA | ACC | GTC | ATC | TTT | TGT | TTG | GCG GAT | 3239 |
| Gly | Gly | Ala | Thr | Gly | Ala | Ser | Glu | Thr | Val | Ile | Phe | Cys | Leu | Ala Asp | |
| | | 130 | | | | | 135 | | | | | 140 | | | |

| | | | | | | | | | | |
|---|---|---|---|---|---|---|---|---|---|---|
| CCG | GGG | GAT | GCT | TTT | TTG | GTT | CCT | TCT | CCA TAC TAT GCA GCG | 3281 |
| Pro | Gly | Asp | Ala | Phe | Leu | Val | Pro | Ser | Pro Tyr Tyr Ala Ala | |
| | 145 | | | | | 150 | | | 155 | |

| | | | | |
|---|---|---|---|---|
| TAAGTTTTTT | TTTTTTTTTT | TTCTTTTAAA | TCTCTCCTTT | TCACTTTACA TATAGAGAGA | 3341 |
| GAAACCATTT | GACAAATTAT | TAACTCTACA | AATTCTCTTT | GAAAGTCGTA TGTTTTGGGA | 3401 |
| GGGTCCAAAC | TTCAACCATT | CTACCAAGTA | AACAATCCAC | CTCTTTCATG CCTCATTGCT | 3461 |
| GGCATACCTC | CTCGTCTTCT | CCCTATACTT | TCTTTCTTTG | TATTCTTCTC CCTAACCGAT | 3521 |
| GTGTAATTTC | ACAATCTACT | CCTTCGAGCT | CCAGCATTCT | TGTTGGCACA CCACTTTGTG | 3581 |
| TCCACTCCCC | TTCGAGGCTC | AGCCTTCTCG | CTAGCTCATT | GCTCGGTGTC TGGTTCTAAT | 3641 |
| ATCATTTGTA | ACAGTCCAAG | TCCAATGCTA | GTAGATATTG | TCCTCGCTTT GGGCTTTCCC | 3701 |
| TCTCGGACAT | TCCATCAAGT | TTTTAGAACA | CGTCTGCTAA | GAAAAGTTT TCACACCCTT | 3761 |
| ATAAATAATG | CTTCGTTCTC | CTCCCTAACC | GATATGGGAT | CTCACTGAAT ATTACCCACT | 3821 |
| TGAATAAACT | AATAACTTGT | GCTCTTCGTT | CTTGATATGA | AAATCAACCC GATGGAAAGA | 3881 |
| ACTGATGTCA | AATGATAAGA | AAATCACTAT | AAGGGAAGTA | AGATTCGGAT TACCTTGTTG | 3941 |
| ATCGAATATC | TCAAGGCAAG | AACACTTGTT | TGAAATTCGA | ATCACTCCAC AACCAAGATT | 4001 |
| GATCATGTTG | AGCTTGAATG | ATTCTGCATG | CAATCTAAAC | TACATAGAAT TACAAAGAAA | 4061 |
| CTTAGTCATT | GGCTAAAGAA | AGCACAAATG | TTTCTTTTAC | TATATTTTCC AAGTCGGCTT | 4121 |
| ACAAATACAA | CATACATGAC | TTCGTATAAT | CTCAAAATGA | AACTATTTAA GGCATTATAA | 4181 |
| GAGTGGTAAC | ATTCATAATT | TATGACCATA | ATTAACCATT | ATGTAAATAT AATCTAAGGT | 4241 |
| AAATAAAAAG | CCTTAAAACA | TATTAATGAA | ATACAATAAC | TCCAAATTTT CTAGATTGTA | 4301 |
| ATCCACCCAA | AATTTATAAA | AATGAAACTT | CATTCTTCTT | CAATGTGACA TGTGGCATGA | 4361 |
| ACTGAAATAT | CTATTTTCTT | CCCATGTTCA | TCGAAATATA | GTGTATGATT GATGTCTCTT | 4421 |
| GGTTCATATC | AGTTCTTTAC | ATATATTAAT | AACCTTTTGG | TACGAGGTGA ACAATGTCGT | 4481 |
| ATTATTGTAA | AAATACTCAA | AAGTCTTTGT | CCTAACAATC | AGTACGTTGT TTTTCAGG | 4539 |

```
TTT GAT CGA GAC CTA AAA TGG CGA ACA CGA GCA CAA ATA ATT CCT GTT      4587
Phe Asp Arg Asp Leu Lys Trp Arg Thr Arg Ala Gln Ile Ile Pro Val
        160                 165                 170

CAT TGC AAC AGC TCG AAC AAC TTC CAA GTC ACA GAG GCA GCC TTA GAA      4635
His Cys Asn Ser Ser Asn Asn Phe Gln Val Thr Glu Ala Ala Leu Glu
    175                 180                 185

ATA GCC TAT AAA AAG GCT CAA GAG GCC AAC ATG AAA GTG AAG GGT GTT      4683
Ile Ala Tyr Lys Lys Ala Gln Glu Ala Asn Met Lys Val Lys Gly Val
190                 195                 200                 205

ATA ATC ACC AAT CCC TCA AAT CCC TTA GGC ACA ACG TAC GAC CGT GAC      4731
Ile Ile Thr Asn Pro Ser Asn Pro Leu Gly Thr Thr Tyr Asp Arg Asp
                210                 215                 220

ACT CTT AAA ACC CTC GTC ACC TTT GTG AAT CAA CAC GAC ATT CAC TTA      4779
Thr Leu Lys Thr Leu Val Thr Phe Val Asn Gln His Asp Ile His Leu
        225                 230                 235

ATA TGC GAT GAA ATA TAC TCT GCC ACT GTC TTC AAA GCC CCA ACC TTC      4827
Ile Cys Asp Glu Ile Tyr Ser Ala Thr Val Phe Lys Ala Pro Thr Phe
    240                 245                 250

ACC AGC ATC GCT GAG ATT GTT GAA CAA ATG GAG CAT TGC AAG AAG GAG      4875
Thr Ser Ile Ala Glu Ile Val Glu Gln Met Glu His Cys Lys Lys Glu
255                 260                 265

CTC ATC CAT ATT CTT TAT AGC TTG TCC AAA GAC ATG GGC CTC CCT GGT      4923
Leu Ile His Ile Leu Tyr Ser Leu Ser Lys Asp Met Gly Leu Pro Gly
270                 275                 280                 285

TTT CGA GTT GGA ATT ATT TAT TCT TAC AAC GAT GTC GTC GTC CGC CGT      4971
Phe Arg Val Gly Ile Ile Tyr Ser Tyr Asn Asp Val Val Val Arg Arg
                290                 295                 300

GCT CGG CAG ATG TCG AGC TTC GGC CTC GTC TCG TCC CAG ACT CAA CAT      5019
Ala Arg Gln Met Ser Ser Phe Gly Leu Val Ser Ser Gln Thr Gln His
```

```
                305                        310                         315
TTG CTC GCC GCC ATG CTT TCC GAC GAG GAC TTT GTC GAC AAA TTT CTT              5067
Leu Leu Ala Ala Met Leu Ser Asp Glu Asp Phe Val Asp Lys Phe Leu
            320                 325                 330

GCC GAG AAC TCG AAG CGC CTG GGC GAG AGG CAT GCA AGG TTTGTTAAAC               5116
Ala Glu Asn Ser Lys Arg Leu Gly Glu Arg His Ala Arg
        335                 340                 345

TACACCATTA TTATTTGTGG GATTGAAAAG CATTACAAAA TGCAATTAAT TTAAGAATGT            5176

ATTAATCAAA TTCAGG TTC ACA AAA GAA TTG GAT AAA ATG GGG ATC ACT                5225
               Phe Thr Lys Glu Leu Asp Lys Met Gly Ile Thr
                            350                 355

TGC TTG AAC AGC AAT GCT GGA GTT TTT GTG TGG ATG GAT CTA CGG AGG              5273
Cys Leu Asn Ser Asn Ala Gly Val Phe Val Trp Met Asp Leu Arg Arg
            360                 365                 370

CTA TTA AAA GAC CAA ACC TTC AAA GCT GAA ATG GAG CTT TGG CGT GTG              5321
Leu Leu Lys Asp Gln Thr Phe Lys Ala Glu Met Glu Leu Trp Arg Val
    375                 380                 385

ATT ATC AAT GAA GTC AAG CTC AAT GTT TCT CCT GGC TCA TCC TTT CAT              5369
Ile Ile Asn Glu Val Lys Leu Asn Val Ser Pro Gly Ser Ser Phe His
390                 395                 400                 405

GTC ACT GAG CCA GGT TGG TTT CGA GTT TGT TTC GCA AAC ATG GAC GAC              5417
Val Thr Glu Pro Gly Trp Phe Arg Val Cys Phe Ala Asn Met Asp Asp
                410                 415                 420

AAC ACC GTT GAC GTT GCT CTC AAT AGA ATC CAT AGC TTT GTC GAA AAC              5465
Asn Thr Val Asp Val Ala Leu Asn Arg Ile His Ser Phe Val Glu Asn
            425                 430                 435

ATC GAC AAG AAG GAA GAC AAT ACC GTT GCA ATG CCA TCG AAA ACG AGG              5513
Ile Asp Lys Lys Glu Asp Asn Thr Val Ala Met Pro Ser Lys Thr Arg
        440                 445                 450

CAT CGA GAT AAT AAG TTA CGA TTG AGC TTC TCC TTC TCC GGG AGA AGA              5561
His Arg Asp Asn Lys Leu Arg Leu Ser Phe Ser Phe Ser Gly Arg Arg
    455                 460                 465

TAC GAC AAG GGC AAC GTT CTT AAC TCA CCG CAC ACG ATG TCG CCT CAC              5609
Tyr Asp Lys Gly Asn Val Leu Asn Ser Pro His Thr Met Ser Pro His
470                 475                 480                 485

TCG CCA TTG GTA AGA GCC AGA ACT TAT TAAAGATGAG TTTGAGAAGA                    5656
Ser Pro Leu Val Arg Ala Arg Thr Tyr
                490

TATTATCATA AGTTTTTTTT AGCTCATTAA TGAATGGATG GATATTTAAA ACTATGAAGT            5716

GTAGCACTCA TGCTCCGAAG GAATTAATTT CTTGATTGCT GAATTTTAAG ACGATATAAA            5776

AGAGAAAAAA TGTTTAGAAA AATCTAAAAA ATGGGAGAAA AAAAGAAAA CAATTAAAAT             5836

TTAAAAATCA GTCAAAATCA TTAAAGTAGT ACATATAGCT CATACTAGAA GGTGAGACAA            5896

GACTCTGAAA TGATTTTTAT GATACGTCTT TAACTACGAT TGCATTTCTT GACTGGGGTT            5956

ACTGCATTTC TTGACTGGGG TTACTTACTA AGTATTTCTA GAAATACTCA AGTCACATGC            6016

TACTCTTATT TTCAGGTAAA GGCAATGTAC CTCTTCACGG ACGATGACGT CGCGGTGACG            6076

CCATGAGATT GAAGCTAGGG TAGAAGTATT CATGTTATTT TTGTAGCCCT TAGGTTAGAT            6136

CAAAATATCG TCTTATTTTA TTTTTATTTT ATCAAATTT TACGTGATTT GTTTTCCATT             6196

TTAATTGTTC AATAATTTTA TTATGAACAT GTAAGTTCAT GGCACTTTTT TAAAATATTT            6256

TAAAAGTTTT TTTTTTTCGA TTCTTAATTA ATTTATGCAT GTAGTAGCGA GTTTATCATA            6316

GTCAAGGAGG ATGTTTTGTG AAATGTTAAG CTGAATGGTT ATGTGTAAAA CGGAGAGTCT            6376

ACTAATGCTA TTAAGATTTT TATGTAAACA AGTCTTCCAC TTGATTTCTG TCTTGATTTG            6436

CTACATCTCG ATTTCTTCCG TCAAGAATTT CTCTCTAACG AAATGATAAT GCACCTCCAC            6496
```

-continued

```
ATGTTTTATT CTAGCATGAA ACATCGAATT TTCTGTTAGG CAAATCGCAG ATTGGTTGTT    6556
GTAATGAAGT GGTATTGGAT AGTCAATTTT CTTGTGCCGA TCTTTCATCA AGAGTTTCAG    6616
TCATGTACTT TCCTAAACTG CTCCAACCGC TACTCTGTAC TCTACTTCTC TAGTTGACAA    6676
TGATACTGTT GATTTCTTT TGCTACACTG AGAAGTTGTT CTCGAACCGA GCTTGAACAC     6736
ATACCTGGTG CTTGATCTTC GGGTATTGTG ATATTCTACA TAGTCAGCAT CACGGTATCT    6796
GGATAACTTG TAGTCTTCGC TTCTTTTATA CAAACGATCA TAATGATTGT GCCTTTGACA    6856
TATCTCAAGG TCCGTCAAGT CGCATCCAAA TGAGGTTTCT TTGCACTTTG TATGTACTGA    6916
CTAATGACTC CAACTCCGTT CTCAAATTTC TTCGGTTGGT TCATGTAGAT CTCTCTATTT    6976
AACTCTCCGT GCAAGAAAGC ATTCTTCATA TCCATCTGTC GTAATTTCCA ATCTTTATTT    7036
ACCACAAGTG CTGGAGGAAC CTATATGATG GTGATCTTTG CCACTGAACT AAATGTTTCA    7096
TCATAGTCCA TATTGTTGAG AGAACCCTGG AGCTACAGTC TGAGTTGTGT ATCTCACTAT    7156
TCATCCATTC GGGATACACT TTATTTTGTA AATCCACTTG CAAAAGATGG ATTTGACATC    7216
TTCTGGTCTT TGTACTAATT CCCAGGTTTG ATTTATCTCG AAGGGTATAA TTTCTTCCTC    7276
CATTGTCTGC TGCCAAGCCG TATTGCGTGA TGCTTCTTTA TACGTCTCTA GCTCTTTACT    7336
TTGTCTTCTA AAATAGTTAT ATTGAACATA CTTTGGATTT GGCTTATGGA TTCTTTCTAA    7396
CCATCTAAGT CGTTGAGGTG TCATTTCCTT TTCACTAGGT TCGCTTGATT GAGTCACTCC    7456
TTGCTCACCA ACATTAGTGT CACTTGGATA TTTAGACACA TCAGCATTTA AGAAAATGTG    7516
TACAGTTTTC TCCCCCGTAT TCTGTGGAAG AATTTCTTCA GTTGCTCCC CCGTCTTCTG     7576
TGGAAGAATT C                                                          7587
```

( 2 ) INFORMATION FOR SEQ ID NO:23:

( i ) SEQUENCE CHARACTERISTICS:
        ( A ) LENGTH: 494 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Met Gly Phe His Gln Ile Asp Glu Arg Asn Gln Ala Leu Leu Ser Lys
 1               5                  10                  15

Ile Ala Ile Asp Asp Gly His Gly Glu Asn Ser Ala Tyr Phe Asp Gly
             20                  25                  30

Trp Lys Ala Tyr Asp Asn Asn Pro Phe His Pro Glu Asn Asn Pro Leu
         35                  40                  45

Gly Val Ile Gln Met Gly Leu Ala Glu Asn Gln Leu Ser Phe Gly Met
     50                  55                  60

Ile Val Asp Trp Ile Arg Lys His Pro Glu Ala Ser Ile Cys Thr Pro
 65                  70                  75                  80

Glu Gly Leu Glu Lys Phe Lys Ser Ile Ala Asn Phe Gln Asp Tyr His
                 85                  90                  95

Gly Leu Gln Glu Phe Arg Lys Ala Met Ala Ser Phe Met Gly Lys Val
             100                 105                 110

Arg Gly Gly Arg Val Lys Phe Asp Pro Ser Arg Ile Val Met Gly Gly
         115                 120                 125

Gly Ala Thr Gly Ala Ser Glu Thr Val Ile Phe Cys Leu Ala Asp Pro
    130                 135                 140

Gly Asp Ala Phe Leu Val Pro Ser Pro Tyr Tyr Ala Ala Phe Asp Arg
145                 150                 155                 160
```

| Asp | Leu | Lys | Trp | Arg | Thr | Arg | Ala | Gln | Ile | Ile | Pro | Val | His | Cys | Asn |
|||||165|||||170|||||175||

| Ser | Ser | Asn | Asn | Phe | Gln | Val | Thr | Glu | Ala | Ala | Leu | Glu | Ile | Ala | Tyr |
||||180|||||185|||||190|||

| Lys | Lys | Ala | Gln | Glu | Ala | Asn | Met | Lys | Val | Lys | Gly | Val | Ile | Ile | Thr |
|||195|||||200|||||205||||

| Asn | Pro | Ser | Asn | Pro | Leu | Gly | Thr | Thr | Tyr | Asp | Arg | Asp | Thr | Leu | Lys |
||210||||215|||||220|||||

| Thr | Leu | Val | Thr | Phe | Val | Asn | Gln | His | Asp | Ile | His | Leu | Ile | Cys | Asp |
|225||||230|||||235|||||240|

| Glu | Ile | Tyr | Ser | Ala | Thr | Val | Phe | Lys | Ala | Pro | Thr | Phe | Thr | Ser | Ile |
|||||245|||||250|||||255||

| Ala | Glu | Ile | Val | Glu | Gln | Met | Glu | His | Cys | Lys | Lys | Glu | Leu | Ile | His |
||||260|||||265|||||270|||

| Ile | Leu | Tyr | Ser | Leu | Ser | Lys | Asp | Met | Gly | Leu | Pro | Gly | Phe | Arg | Val |
|||275|||||280|||||285||||

| Gly | Ile | Ile | Tyr | Ser | Tyr | Asn | Asp | Val | Val | Val | Arg | Arg | Ala | Arg | Gln |
||290||||295|||||300|||||

| Met | Ser | Ser | Phe | Gly | Leu | Val | Ser | Ser | Gln | Thr | Gln | His | Leu | Leu | Ala |
|305||||310|||||315|||||320|

| Ala | Met | Leu | Ser | Asp | Glu | Asp | Phe | Val | Asp | Lys | Phe | Leu | Ala | Glu | Asn |
|||||325|||||330|||||335||

| Ser | Lys | Arg | Leu | Gly | Glu | Arg | His | Ala | Arg | Phe | Thr | Lys | Glu | Leu | Asp |
||||340|||||345|||||350|||

| Lys | Met | Gly | Ile | Thr | Cys | Leu | Asn | Ser | Asn | Ala | Gly | Val | Phe | Val | Trp |
|||355|||||360|||||365||||

| Met | Asp | Leu | Arg | Arg | Leu | Leu | Lys | Asp | Gln | Thr | Phe | Lys | Ala | Glu | Met |
||370||||375|||||380|||||

| Glu | Leu | Trp | Arg | Val | Ile | Ile | Asn | Glu | Val | Lys | Leu | Asn | Val | Ser | Pro |
|385||||390|||||395|||||400|

| Gly | Ser | Ser | Phe | His | Val | Thr | Glu | Pro | Gly | Trp | Phe | Arg | Val | Cys | Phe |
|||||405|||||410|||||415||

| Ala | Asn | Met | Asp | Asp | Asn | Thr | Val | Asp | Val | Ala | Leu | Asn | Arg | Ile | His |
||||420|||||425|||||430|||

| Ser | Phe | Val | Glu | Asn | Ile | Asp | Lys | Lys | Glu | Asp | Asn | Thr | Val | Ala | Met |
|||435|||||440|||||445||||

| Pro | Ser | Lys | Thr | Arg | His | Arg | Asp | Asn | Lys | Leu | Arg | Leu | Ser | Phe | Ser |
||450||||455|||||460|||||

| Phe | Ser | Gly | Arg | Arg | Tyr | Asp | Lys | Gly | Asn | Val | Leu | Asn | Ser | Pro | His |
|465||||470|||||475|||||480|

| Thr | Met | Ser | Pro | His | Ser | Pro | Leu | Val | Arg | Ala | Arg | Thr | Tyr |
|||||485|||||490||||

(2) INFORMATION FOR SEQ ID NO:24:

(i) SEQUENCE CHARACTERISTICS:
        (A) LENGTH: 2230 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 91..1545

(xi) SEQUENCE DESCRIPTION: SEQ ID NO:24:

```
TGTAGTTGTG TACATTTTAT TAATCTTCAT CTTCTTAATT CTCTTCAGTT TTTAATTTCT    60
```

```
                                                               -continued

TCACTTCTAA ACTCATTTAG TAAAAAAAAA ATG GGA TTT GAG ATT GCA AAG ACC            114
                                    Met Gly Phe Glu Ile Ala Lys Thr
                                    1                   5

AAC TCA ATC TTA TCA AAA TTG GCT ACT AAT GAA GAG CAT GGC GAA AAC             162
Asn Ser Ile Leu Ser Lys Leu Ala Thr Asn Glu Glu His Gly Glu Asn
        10              15                  20

TCG CCA TAT TTT GAT GGG TGG AAA GCA TAC GAT AGT GAT CCT TTC CAC             210
Ser Pro Tyr Phe Asp Gly Trp Lys Ala Tyr Asp Ser Asp Pro Phe His
25                  30                  35                  40

CCT CTA AAA AAC CCC AAC GGA GTT ATC CAA ATG GGT CTT GCT GAA AAT             258
Pro Leu Lys Asn Pro Asn Gly Val Ile Gln Met Gly Leu Ala Glu Asn
                    45                  50                  55

CAG CTT TGT TTA GAC TTG ATA GAA GAT TGG ATT AAG AGA AAC CCA AAA             306
Gln Leu Cys Leu Asp Leu Ile Glu Asp Trp Ile Lys Arg Asn Pro Lys
            60                  65                  70

GGT TCA ATT TGT TCT GAA GGA ATC AAA TCA TTC AAG GCC ATT GCC AAC             354
Gly Ser Ile Cys Ser Glu Gly Ile Lys Ser Phe Lys Ala Ile Ala Asn
        75                  80                  85

TTT CAA GAT TAT CAT GGC TTG CCT GAA TTC AGA AAA GCG ATT GCG AAA             402
Phe Gln Asp Tyr His Gly Leu Pro Glu Phe Arg Lys Ala Ile Ala Lys
    90                  95                  100

TTT ATG GAG AAA ACA AGA GGA GGA AGA GTT AGA TTT GAT CCA GAA AGA             450
Phe Met Glu Lys Thr Arg Gly Gly Arg Val Arg Phe Asp Pro Glu Arg
105                 110                 115                 120

GTT GTT ATG GTT GGT GGT GCC ACT GGA GCT AAT GAG ACA ATT ATA TTT             498
Val Val Met Val Gly Gly Ala Thr Gly Ala Asn Glu Thr Ile Ile Phe
                125                 130                 135

TGT TTG GCT GAT CCT GGC GAT GCA TTT TTA GTA CCT TCA CCA TAC TAC             546
Cys Leu Ala Asp Pro Gly Asp Ala Phe Leu Val Pro Ser Pro Tyr Tyr
            140                 145                 150

CCA GCA TTT AAC AGA GAT TTA AGA TGG AGA ACT GGA GTA CAA CTT ATT             594
Pro Ala Phe Asn Arg Asp Leu Arg Trp Arg Thr Gly Val Gln Leu Ile
        155                 160                 165

CCA ATT CAC TGT GAG AGC TCC AAT AAT TTC AAA ATT ACT TCA AAA GCA             642
Pro Ile His Cys Glu Ser Ser Asn Asn Phe Lys Ile Thr Ser Lys Ala
    170                 175                 180

GTA AAA GAA GCA TAT GAA AAT GCA CAA AAA TCA AAC ATC AAA GTA AAA             690
Val Lys Glu Ala Tyr Glu Asn Ala Gln Lys Ser Asn Ile Lys Val Lys
185                 190                 195                 200

GGT TTG ATT TTG ACC AAT CCA TCA AAT CCA TTG GGC ACC ACT TTG GAC             738
Gly Leu Ile Leu Thr Asn Pro Ser Asn Pro Leu Gly Thr Thr Leu Asp
                205                 210                 215

AAA GAC ACA CTG AAA AGT GTC TTG AGT TTC ACC AAC CAA CAC AAC ATC             786
Lys Asp Thr Leu Lys Ser Val Leu Ser Phe Thr Asn Gln His Asn Ile
            220                 225                 230

CAC CTT GTT TGT GAC GAA ATC TAC GCA GCC ACT GTC TTT GAC ACG CCT             834
His Leu Val Cys Asp Glu Ile Tyr Ala Ala Thr Val Phe Asp Thr Pro
        235                 240                 245

CAA TTC GTC AGT ATA GCT GAA ATC CTC GAT GAA CAG GAA ATG ACT TAC             882
Gln Phe Val Ser Ile Ala Glu Ile Leu Asp Glu Gln Glu Met Thr Tyr
    250                 255                 260

TGC AAC AAA GAT TTA GTT CAC ATC GTC TAC AGT CTT TCA AAA GAC ATG             930
Cys Asn Lys Asp Leu Val His Ile Val Tyr Ser Leu Ser Lys Asp Met
265                 270                 275                 280

GGG TTA CCA GGA TTT AGA GTC GGA ATC ATA TAT TCT TTT AAC GAC GAT             978
Gly Leu Pro Gly Phe Arg Val Gly Ile Ile Tyr Ser Phe Asn Asp Asp
                285                 290                 295

GTC GTT AAT TGT GCT AGA AAA ATG TCG AGT TTC GGT TTA GTA TCT ACA             1026
Val Val Asn Cys Ala Arg Lys Met Ser Ser Phe Gly Leu Val Ser Thr
            300                 305                 310
```

| CAA | ACG | CAA | TAT | TTT | TTA | GCG | GCA | ATG | CTA | TCG | GAC | GAA | AAA | TTC | GTC | 1074 |
| Gln | Thr | Gln | Tyr | Phe | Leu | Ala | Ala | Met | Leu | Ser | Asp | Glu | Lys | Phe | Val | |
| | 315 | | | | | 320 | | | | | 325 | | | | | |

| GAT | AAT | TTT | CTA | AGA | GAA | AGC | GCG | ATG | AGG | TTA | GGT | AAA | AGG | CAC | AAA | 1122 |
| Asp | Asn | Phe | Leu | Arg | Glu | Ser | Ala | Met | Arg | Leu | Gly | Lys | Arg | His | Lys | |
| | 330 | | | | | 335 | | | | | 340 | | | | | |

| CAT | TTT | ACT | AAT | GGA | CTT | GAA | GTA | GTG | GGA | ATT | AAA | TGC | TTG | AAA | AAT | 1170 |
| His | Phe | Thr | Asn | Gly | Leu | Glu | Val | Val | Gly | Ile | Lys | Cys | Leu | Lys | Asn | |
| 345 | | | | | 350 | | | | | 355 | | | | | 360 | |

| AAT | GCG | GGG | CTT | TTT | TGT | TGG | ATG | GAT | TTG | CGT | CCA | CTT | TTA | AGG | GAA | 1218 |
| Asn | Ala | Gly | Leu | Phe | Cys | Trp | Met | Asp | Leu | Arg | Pro | Leu | Leu | Arg | Glu | |
| | | | | 365 | | | | | 370 | | | | | 375 | | |

| TCG | ACT | TTC | GAT | AGC | GAA | ATG | TCG | TTA | TGG | AGA | GTT | ATT | ATA | AAC | GAT | 1266 |
| Ser | Thr | Phe | Asp | Ser | Glu | Met | Ser | Leu | Trp | Arg | Val | Ile | Ile | Asn | Asp | |
| | | | 380 | | | | | 385 | | | | | 390 | | | |

| GTT | AAG | CTT | AAC | GTC | TCG | CCT | GGA | TCT | TCG | TTT | GAA | TGT | CAA | GAG | CCA | 1314 |
| Val | Lys | Leu | Asn | Val | Ser | Pro | Gly | Ser | Ser | Phe | Glu | Cys | Gln | Glu | Pro | |
| | | 395 | | | | | 400 | | | | | 405 | | | | |

| GGG | TGG | TTC | CGA | GTT | TGT | TTT | GCA | AAT | ATG | GAT | GAT | GGA | ACG | GTT | GAT | 1362 |
| Gly | Trp | Phe | Arg | Val | Cys | Phe | Ala | Asn | Met | Asp | Asp | Gly | Thr | Val | Asp | |
| | 410 | | | | | 415 | | | | | 420 | | | | | |

| ATT | GCG | CTC | GCG | AGG | ATT | CGG | AGG | TTC | GTA | GGT | GTT | GAG | AAA | AGT | GGA | 1410 |
| Ile | Ala | Leu | Ala | Arg | Ile | Arg | Arg | Phe | Val | Gly | Val | Glu | Lys | Ser | Gly | |
| 425 | | | | | 430 | | | | | 435 | | | | | 440 | |

| GAT | AAA | TCG | AGT | TCG | ATG | GAA | AAG | AAG | CAA | CAA | TGG | AAG | AAG | AAT | AAT | 1458 |
| Asp | Lys | Ser | Ser | Ser | Met | Glu | Lys | Lys | Gln | Gln | Trp | Lys | Lys | Asn | Asn | |
| | | | | 445 | | | | | 450 | | | | | 455 | | |

| TTG | AGA | CTT | AGT | TTT | TCG | AAA | AGA | ATG | TAT | GAT | GAA | AGT | GTT | TTG | TCA | 1506 |
| Leu | Arg | Leu | Ser | Phe | Ser | Lys | Arg | Met | Tyr | Asp | Glu | Ser | Val | Leu | Ser | |
| | | | 460 | | | | | 465 | | | | | 470 | | | |

| CCA | CTT | TCG | TCA | CCT | ATT | CCT | CCC | TCA | CCA | TTA | GTT | CGT | TAAGACTTAA | | | 1555 |
| Pro | Leu | Ser | Ser | Pro | Ile | Pro | Pro | Ser | Pro | Leu | Val | Arg | | | | |
| | | 475 | | | | | 480 | | | | | 485 | | | | |

| TTAAAAGGGA | AGAATTTAAT | TTATGTTTTT | TTATATTTTG | AAAAAAATTT | GTAAGAATAA | 1615 |
| GATTATAATA | GGAAAAGAAA | ATAAGTATGT | AGGATGAGGA | GTATTTTCAG | AAATAGTTGT | 1675 |
| TAGCGTATGT | ATTGACAACT | GGTCTATGTA | CTTAGACATC | ATAATTTGTC | TTAGCTAATT | 1735 |
| AACGAATGCA | AAAGTGAAGT | TATGTTATGA | CTCTTAGAAT | ATGTACTTAG | ACATCATAAT | 1795 |
| TTGTCTTAGC | TAATTAATGA | ATGCAAAAGT | GAAGTTATGT | TATGACTCTT | AGAATCTTTT | 1855 |
| GATTATTGG | ACTTTCTCGA | ATGTACTTAG | ACATCATAAT | TTGTCTTAGC | TAATTAATGA | 1915 |
| ATGCAAAAGT | GAAGTTATGT | TATGAAAAAA | AAAAAAAAAA | AAAATGTACT | TAGACATCAT | 1975 |
| AATTTGTCTT | AGCTAATTAA | TGAATGCAAA | AGTGAAGTTA | TGTTAAAAAA | AAAAAAAAA | 2035 |
| AAAAATGTAC | TTAGACATCA | TAATTTGTCT | TAGCTAATTA | ATGAATGCAA | AAGTGAAGTT | 2095 |
| ATGTTAAAAA | AAAAAAAAAA | AAAAATGTAC | TTAGACATCA | TAATTTGTCT | TAGCTAATTA | 2155 |
| AAAAAAAAAA | AAAAAAAAAA | AAAAAAAAAA | AAAAAAAAAA | AAAAAAAAAA | AAAAAAATTA | 2215 |
| TATTGTTAAA | AAAAA | | | | | 2230 |

( 2 ) INFORMATION FOR SEQ ID NO:25:

( i ) SEQUENCE CHARACTERISTICS:
        ( A ) LENGTH: 485 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

| | | | | | | | | | | | | | | |
|---|---|---|---|---|---|---|---|---|---|---|---|---|---|---|
| Met | Gly | Phe | Glu | Ile | Ala | Lys | Thr | Asn | Ser | Ile | Leu | Ser | Lys | Leu | Ala |
| 1 | | | | 5 | | | | | 10 | | | | | 15 | |
| Thr | Asn | Glu | Glu | His | Gly | Glu | Asn | Ser | Pro | Tyr | Phe | Asp | Gly | Trp | Lys |
| | | | 20 | | | | | 25 | | | | | 30 | | |
| Ala | Tyr | Asp | Ser | Asp | Pro | Phe | His | Pro | Leu | Lys | Asn | Pro | Asn | Gly | Val |
| | | | 35 | | | | 40 | | | | | 45 | | | |
| Ile | Gln | Met | Gly | Leu | Ala | Glu | Asn | Gln | Leu | Cys | Leu | Asp | Leu | Ile | Glu |
| | | 50 | | | | | 55 | | | | 60 | | | | |
| Asp | Trp | Ile | Lys | Arg | Asn | Pro | Lys | Gly | Ser | Ile | Cys | Ser | Glu | Gly | Ile |
| 65 | | | | | 70 | | | | | 75 | | | | | 80 |
| Lys | Ser | Phe | Lys | Ala | Ile | Ala | Asn | Phe | Gln | Asp | Tyr | His | Gly | Leu | Pro |
| | | | | 85 | | | | | 90 | | | | | 95 | |
| Glu | Phe | Arg | Lys | Ala | Ile | Ala | Lys | Phe | Met | Glu | Lys | Thr | Arg | Gly | Gly |
| | | | 100 | | | | | 105 | | | | | 110 | | |
| Arg | Val | Arg | Phe | Asp | Pro | Glu | Arg | Val | Val | Met | Val | Gly | Gly | Ala | Thr |
| | | 115 | | | | | 120 | | | | | 125 | | | |
| Gly | Ala | Asn | Glu | Thr | Ile | Ile | Phe | Cys | Leu | Ala | Asp | Pro | Gly | Asp | Ala |
| | 130 | | | | | 135 | | | | | 140 | | | | |
| Phe | Leu | Val | Pro | Ser | Pro | Tyr | Tyr | Pro | Ala | Phe | Asn | Arg | Asp | Leu | Arg |
| 145 | | | | | 150 | | | | | 155 | | | | | 160 |
| Trp | Arg | Thr | Gly | Val | Gln | Leu | Ile | Pro | Ile | His | Cys | Glu | Ser | Ser | Asn |
| | | | | 165 | | | | | 170 | | | | | 175 | |
| Asn | Phe | Lys | Ile | Thr | Ser | Lys | Ala | Val | Lys | Glu | Ala | Tyr | Glu | Asn | Ala |
| | | | 180 | | | | | 185 | | | | | 190 | | |
| Gln | Lys | Ser | Asn | Ile | Lys | Val | Lys | Gly | Leu | Ile | Leu | Thr | Asn | Pro | Ser |
| | | 195 | | | | | 200 | | | | | 205 | | | |
| Asn | Pro | Leu | Gly | Thr | Thr | Leu | Asp | Lys | Asp | Thr | Leu | Lys | Ser | Val | Leu |
| | 210 | | | | | 215 | | | | | 220 | | | | |
| Ser | Phe | Thr | Asn | Gln | His | Asn | Ile | His | Leu | Val | Cys | Asp | Glu | Ile | Tyr |
| 225 | | | | | 230 | | | | | 235 | | | | | 240 |
| Ala | Ala | Thr | Val | Phe | Asp | Thr | Pro | Gln | Phe | Val | Ser | Ile | Ala | Glu | Ile |
| | | | | 245 | | | | | 250 | | | | | 255 | |
| Leu | Asp | Glu | Gln | Glu | Met | Thr | Tyr | Cys | Asn | Lys | Asp | Leu | Val | His | Ile |
| | | | 260 | | | | | 265 | | | | | 270 | | |
| Val | Tyr | Ser | Leu | Ser | Lys | Asp | Met | Gly | Leu | Pro | Gly | Phe | Arg | Val | Gly |
| | | 275 | | | | | 280 | | | | | 285 | | | |
| Ile | Ile | Tyr | Ser | Phe | Asn | Asp | Asp | Val | Val | Asn | Cys | Ala | Arg | Lys | Met |
| | 290 | | | | | 295 | | | | | 300 | | | | |
| Ser | Ser | Phe | Gly | Leu | Val | Ser | Thr | Gln | Thr | Gln | Tyr | Phe | Leu | Ala | Ala |
| 305 | | | | | 310 | | | | | 315 | | | | | 320 |
| Met | Leu | Ser | Asp | Glu | Lys | Phe | Val | Asp | Asn | Phe | Leu | Arg | Glu | Ser | Ala |
| | | | | 325 | | | | | 330 | | | | | 335 | |
| Met | Arg | Leu | Gly | Lys | Arg | His | Lys | His | Phe | Thr | Asn | Gly | Leu | Glu | Val |
| | | | 340 | | | | | 345 | | | | | 350 | | |
| Val | Gly | Ile | Lys | Cys | Leu | Lys | Asn | Asn | Ala | Gly | Leu | Phe | Cys | Trp | Met |
| | | 355 | | | | | 360 | | | | | 365 | | | |
| Asp | Leu | Arg | Pro | Leu | Leu | Arg | Glu | Ser | Thr | Phe | Asp | Ser | Glu | Met | Ser |
| | 370 | | | | | 375 | | | | | 380 | | | | |
| Leu | Trp | Arg | Val | Ile | Ile | Asn | Asp | Val | Lys | Leu | Asn | Val | Ser | Pro | Gly |
| 385 | | | | | 390 | | | | | 395 | | | | | 400 |
| Ser | Ser | Phe | Glu | Cys | Gln | Glu | Pro | Gly | Trp | Phe | Arg | Val | Cys | Phe | Ala |
| | | | | 405 | | | | | 410 | | | | | 415 | |
| Asn | Met | Asp | Asp | Gly | Thr | Val | Asp | Ile | Ala | Leu | Ala | Arg | Ile | Arg | Arg |
| | | | 420 | | | | | 425 | | | | | 430 | | |

| Phe | Val | Gly | Val | Glu | Lys | Ser | Gly | Asp | Lys | Ser | Ser | Met | Glu | Lys |
|---|---|---|---|---|---|---|---|---|---|---|---|---|---|---|
| | | 435 | | | | | 440 | | | | | 445 | | |

| Lys | Gln | Gln | Trp | Lys | Lys | Asn | Asn | Leu | Arg | Leu | Ser | Phe | Ser | Lys | Arg |
|---|---|---|---|---|---|---|---|---|---|---|---|---|---|---|---|
| | 450 | | | | | 455 | | | | | 460 | | | | |

| Met | Tyr | Asp | Glu | Ser | Val | Leu | Ser | Pro | Leu | Ser | Ser | Pro | Ile | Pro | Pro |
|---|---|---|---|---|---|---|---|---|---|---|---|---|---|---|---|
| 465 | | | | | 470 | | | | | 475 | | | | | 480 |

| Ser | Pro | Leu | Val | Arg |
|---|---|---|---|---|
| | | | | 485 |

( 2 ) INFORMATION FOR SEQ ID NO:26:

( i ) SEQUENCE CHARACTERISTICS:
        ( A ) LENGTH: 7244 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: join(3056..3226, 3325..3453, 3539..3700, 4582
            . . 5574)

( x i ) SEQUENCE DESCRIPTION: SEQ ID NO:26:

```
GGATCCTCAT TACTTGTCTA TGGCTAAAGT GTTAAAGAAT TATTCACAAT ATCTAACACA      60
TTTAATGACT ATTCAACTAA TAGTGACGAT CTTTTAAAAT AAAATGAAGA ACTTAAAATT     120
TTGACCAACT TCCTAACGAT ATTAATGAGG GATACAGATT TGATTTACGC AAAAAAAAAA     180
GAAAAAAAGA AATGATATTA CTCAATTATA AATTTGATTA GAGAATAGCT AGGCCTATAA     240
TTGTTTTACA TTATCTATTC CTAAGTTATG ATATTATCCT TCAATTTACC TGATAGCGTA     300
AAAATTACAA TAATTTGTAC ACTAATGATG CACAAAACTT AAATTCATTA TATATACACA     360
TACAAGGCCG AGGGCTTAAT AGAATCGATG ACCTGAAATC ATATTTCTAT TGTTTAGCAA     420
TAGAAATTAG TTATGGCTTC AAATTTAGCG ATGAATTCCA TGGGTGTTTG CATTGACTTA     480
AAAGATGATC AAATCTACTT TGAAGTCCGT TTTTGAATTT GAAAGTGTT TGATAAATAT      540
AAAAATAACT AAAAATAAGT TAGGAAGTGT TTGACAAAGT TAAATCTTAA ATAATTTAT      600
CAACCAAAAG TAGGTCTCCC CTATTCTTTT TTTTTTGGA CTTAAAAGTC GTTAAACGT       660
AATTTGACTT ATAAATTTTT TAAAGTTAAT TTAAACCGGC TTTGTAAAAG AAATTAACAA     720
TTCATTTGGA ATGTTAATTA TTAAAAGATC CAGATATGTA CAAAATAAAA ATAACCTACC     780
TCCTATAGTA AAGATTTTCA AACAATATTA AGTTAAACAA AGTCAAAAAG TTGGTATATT     840
GAATTTTACT AGTCTTGTAT AAACCAATAC AATTAGCTTC GAAAAGTCAT TGATATATTT     900
TTCTATGTGC TGCTTGTTGG GAAACTTCCT GTAACACAAA GAATGAATGA ATTCTCCCAC     960
ATTTTTATTT TGTAGATTTA ATTCCCTATT TGATATCAAA AATATTCTGG AGAAGGAAGG    1020
AATACGAGCC TAACCAAGAC TAGGCCAATT AAGCAGCCCA TGATAAGCCT CCATTCAAAT    1080
GAAATATCAA AATCACTGTA TTATTATAAG ATACTTTGAG AATATATATT GTTTGGTCAA    1140
ATAGTTTATT AACATATATA TTATATATAA GTATGTGAAA TGATGAAGCT AGAGTTTTAT    1200
ATGAACATAT AATTTAGATT TTAAGTTGTA TATTTGCTC ATAAATATAA AATTCTATGA    1260
ATTGTAAAAT TATCAATATT TACTTAATTC TTTACGCAAT CTTACTAAAT ATATAAAAGT    1320
TAATAACTAC AAAAGTATAA TCATACGATC ACAAACGAGC TATTCTAAAA AAAGTATCAC    1380
ATATTTAATA TAATCCTCCC ACATAGTACA AACAATCTTC TCATGTTTTG TAATAATAAA    1440
TGATGTAAGG GTTAAAGGT GGTGTGAATA ATAATTGCAA CTAAAAAATT TATTTACATC    1500
TAAAATAAAT AATTAATACA TATAAAATCG TATGATCAAA AATTTAAAAT TTAAATCATG    1560
```

```
ATATGTAATT AATATGTCCA GACACCTGCT TAATAAAAAC TATACACTAT TAATGCAGTA        1620

TGCACTTTAT ACATATTTTG TAAATTAGAT AATTAAATGG CCGGCTAGAG TAATGCAATA        1680

CGATAGAAAA GCTCGATCAA AATTAATCAC ACTCAATGTG CCTAGTAAGA TCTTCAAATC        1740

AAAATCAATT ATGATTATCA TCTGCGGTCC ATTGTTCTCG TCCCTTCCCA GGAAAGTAAT        1800

TATCCCTATT ATATTTTTAT TTATTTATAT AAACTACTTG AAAAAGGTAA AAGAATAAA         1860

TAAATAAATT ACCAGTAGTA CCATTGTATT CTCAACTTTT TTCTTTCTCA CGTGTAGCTT        1920

CTAGCTTGAA CATGAAATTT CATATAACTA TTAGACGAA  GGCAATTACG ACTAAGGGTA        1980

TGTTCGATAA GAAAAGAAAA TATTTCTTA  AAAAATAAAT AAATTTTTAA TTTATTTTTC        2040

ATATTTGATT AATAAGCAGA AATATTTTT  GAGGAAGTAT CTTTTTTTAT TTTGAGAAA         2100

ATACTTTCTA TGAAAATAAT TATTGATGTG AAAATCAATC TCGATAATTG TTGCAGGAAA        2160

CGACTCTGAC AATCGAATTA GGATAAAACC TCGATGACCT TTAAAATCGA CCCTAAAATC        2220

TGATCCAAAA CTCGATCCAG ACTTCCGATC CAAAACTTGA TTCAAGTAAA TATTTTTAAA        2280

AATAAATTCT TTTGACAGG  GTGGCGTAAA AATAATTTA  TTTTAAAATA TGATATAGTT        2340

TTCTAAAATA TATTTTTTTG TTTGGTTGTT GGGGGTTGGT TCGAGGCTAG GGGTAAAAAT        2400

AATTAAAACA TAAGAAATTT TAAAAGTTTT AATTGCATTT TTTTGTGTT   GGGGAGGGGC       2460

GGATTTGGG  TTGGATAAGA AAAATATTT  AAGATAAAA  TAGAATTTG  GAAATATTT         2520

TTCTTAATTT TTGAAGGAAA ATCATTTTC  TTAAATTTGA GAAAATGAA  TTATTCTTAA        2580

AAAAAATTTC CAAAAACATT TAAGCTACCA AATATGAAAA AATAAAAAT  ATTTTTTTC         2640

CTACCAAATG CACCCTAAAT TAGTCAAATA TCCAACATTT AAAAGAGCTA TGAAAAAAA         2700

AAAGAAGTAA GAATCGTAGA TCTTCTTTTA ATGCGTACTT TTATTTTCCA AGATTTGAAC        2760

AATAAAATAG ACTTTTCTAT TTTTATTTTC TGATGTAATT CTTATATACG TTAGTCGACA        2820

TGTTCTCATT ACATACTTCA GTCTTTCCCC TTATATATAT CCCTCACATT CCTTAATTCT        2880

CTTACACCAT AACACAACTA CAACAAACAC ATAATACTTT TAATACAATT AGTTATTTAT        2940

TAGAAGTATT TAAAGTAAAG CACTTGTGAG TTGTGTACAT TTTATTAATC TTCATCTTCT        3000

TAATTCTCTT CAGTTTTTAA TTTCTTCACT TCTAAACTCA TTTAGTAAAA AAAAA ATG        3058
                                                             Met
                                                             1

GGA TTT GAG ATT GCA AAG ACC AAC TCA ATC TTA TCA AAA TTG GCT ACT           3106
Gly Phe Glu Ile Ala Lys Thr Asn Ser Ile Leu Ser Lys Leu Ala Thr
            5               10                  15

AAT GAA GAG CAT GGC GAA AAC TCG CCA TAT TTT GAT GGG TGG AAA GCA           3154
Asn Glu Glu His Gly Glu Asn Ser Pro Tyr Phe Asp Gly Trp Lys Ala
    20              25                  30

TAC GAT AGT GAT CCT TTC CAC CCT CTA AAA AAC CCC AAC GGA GTT ATC           3202
Tyr Asp Ser Asp Pro Phe His Pro Leu Lys Asn Pro Asn Gly Val Ile
35              40                  45

CAA ATG GGT CTT GCT GAA AAT CAG GTAATTAATT ATCCTTTATT TATATATTTT          3256
Gln Met Gly Leu Ala Glu Asn Gln
50              55

GCAGTTTGAC CAAACAGACT ATTATAATTT TTTTCTGAAA CCTCGATGGT GTTAAATTTC         3316

TTTTGTAG CTT TGT TTA GAC TTG ATA GAA GAT TGG ATT AAG AGA AAC CCA          3366
         Leu Cys Leu Asp Leu Ile Glu Asp Trp Ile Lys Arg Asn Pro
         60                  65                  70

AAA GGT TCA ATT TGT TCT GAA GGA ATC AAA TCA TTC AAG GCC ATT GCC           3414
Lys Gly Ser Ile Cys Ser Glu Gly Ile Lys Ser Phe Lys Ala Ile Ala
        75                  80                  85

AAC TTT CAA GAT TAT CAT GGC TTG CCT GAA TTC AGA AAA GTACATATCG            3463
Asn Phe Gln Asp Tyr His Gly Leu Pro Glu Phe Arg Lys
```

```
                Asn Phe Gln Asp Tyr His Gly Leu Pro Glu Phe Arg Lys
                     90              95              100

TACTATAGTC AGTTAAATTA TATTGATAGT ATAAAAATTC GTTAATATAT TTAACTAACG         3523

AGTTTATTTA ATCAG GCG ATT GCG AAA TTT ATG GAG AAA ACA AGA GGA GGA          3574
                Ala Ile Ala Lys Phe Met Glu Lys Thr Arg Gly Gly
                         105                      110

AGA GTT AGA TTT GAT CCA GAA AGA GTT GTT ATG GCT GGT GGT GCC ACT           3622
Arg Val Arg Phe Asp Pro Glu Arg Val Val Met Ala Gly Gly Ala Thr
        115              120             125

GGA GCT AAT GAG ACA ATT ATA TTT TGT TTG GCT GAT CCT GGC GAT GCA           3670
Gly Ala Asn Glu Thr Ile Ile Phe Cys Leu Ala Asp Pro Gly Asp Ala
    130              135             140

TTT TTA GTA CCT TCA CCA TAC TAC CCA GCG TAAGTATATT TAATTATATA            3720
Phe Leu Val Pro Ser Pro Tyr Tyr Pro Ala
145                 150

TGTGTAAAAA AAATTAAAAT CATCAAATCA TTTTTTTTAT TTGTATTACC AAATAAATTG         3780
TCTAATTTTC AAGATTGTAA CACATTCATC AAAGTACCTA ATAATATAAA CGATTCAGTA         3840
TATTAACGAT GTATATAATT TAATTCCTTT GGCGGATTTG TCTTTTATG TTGGGCCATC          3900
AGAAGAACAT TCTGGTGTAT TAATTAATTA ATTAATTAAT AATAGATGTG TTGTCATTCT         3960
TTTTAAGAC AGCGAGAGTT TAATTAGTCT TAATTACTGG ATTATCACGC AAGCTCTTTC          4020
TTGAATTTTA TTATTCTTAT ATTAAACACA TGATAGCATA ATATCTTTCT TTTGTGGAAT         4080
CCAGCTTGTT CGTGAAGCTT TGTATTCACA CTTATAAAAC AACAAAAAAT AAAATCTGGT         4140
GGTAATTGAT TAAAGAGAGA AATATAAAAA AATAATAGTC AAATAGACTA ATAAGGAAAG         4200
AAATAAAAAA TACACAAAAT ACTAAAAAAA AAGAATTAAG GTATAGTGGT CTATTATTGA         4260
GAACTTTTTT GAAGAATTGA ACCCCACTTT AATTTCTTGC TTGACCCGTG ACCATTGCTT         4320
ATCGAGGTAA AATAAAATTT CAAACATTGA CTATGACTTG TTAGAGAGTA ATTACCACAA         4380
GTCAAAATTT TGTTACTCTG TCTCGTTATT TCATTAGGAT CGATAAGATA ACATCTAACA         4440
TATATATCTT TTTTATTAGT ACTTGTTTAT TTTTAGTAAA AGCACGTTAT ACATTTTACA         4500
ATAGTCAATT GTTGCATATA TTAGTATATA TATTTGCTA AGTCCTAACT AACAATATTT          4560
TTGGCAATTG ACTAATGCAG A TTT AAC AGA GAT TTA AGA TGG AGA ACT GGA           4611
                        Phe Asn Arg Asp Leu Arg Trp Arg Thr Gly
                        155                 160

GTA CAA CTT ATT CCA ATT CAC TGT GAG AGC TCC AAT AAT TTC AAA ATT           4659
Val Gln Leu Ile Pro Ile His Cys Glu Ser Ser Asn Asn Phe Lys Ile
165              170             175                 180

ACT TCA AAA GCA GTA AAA GAA GCA TAT GAA AAT GCA CAA AAA TCA AAC           4707
Thr Ser Lys Ala Val Lys Glu Ala Tyr Glu Asn Ala Gln Lys Ser Asn
             185             190             195

ATC AAA GTA AAA GGT TTG ATT TTG ACC AAT CCA TCA AAT CCA TTG GGC           4755
Ile Lys Val Lys Gly Leu Ile Leu Thr Asn Pro Ser Asn Pro Leu Gly
         200             205             210

ACC ACT TTG GAC AAA GAC ACA CTG AAA AGT GTC TTG AGT TTC ACC AAC           4803
Thr Thr Leu Asp Lys Asp Thr Leu Lys Ser Val Leu Ser Phe Thr Asn
        215             220             225

CAA CAC AAC ATC CAC CTT GTT TGT GAC GAA ATC TAC GCA GCC ACT GTC           4851
Gln His Asn Ile His Leu Val Cys Asp Glu Ile Tyr Ala Ala Thr Val
    230             235             240

TTT GAC ACG CCT CAA TTC GTC AGT ATA GCT GAA ATC CTC GAT GAA CAG           4899
Phe Asp Thr Pro Gln Phe Val Ser Ile Ala Glu Ile Leu Asp Glu Gln
245             250             255             260

GAA ATG ACT TAC TGC AAC AAA GAT TTA GTT CAC ATC GTC TAC AGT CTT           4947
Glu Met Thr Tyr Cys Asn Lys Asp Leu Val His Ile Val Tyr Ser Leu
        265             270             275
```

| | | | | | | | | | | | | | | | | |
|---|---|---|---|---|---|---|---|---|---|---|---|---|---|---|---|---|
| TCA | AAA | GAC | ATG | GGG | TTA | CCA | GGA | TTT | AGA | GTC | GGA | ATC | ATA | TAT | TCT | 4995 |
| Ser | Lys | Asp | Met | Gly | Leu | Pro | Gly | Phe | Arg | Val | Gly | Ile | Ile | Tyr | Ser | |
| | | | 280 | | | | | 285 | | | | | 290 | | | |
| TTT | AAC | GAC | GAT | GTC | GTT | AAT | TGT | GCT | AGA | AAA | ATG | TCG | AGT | TTC | GGT | 5043 |
| Phe | Asn | Asp | Asp | Val | Val | Asn | Cys | Ala | Arg | Lys | Met | Ser | Ser | Phe | Gly | |
| | | | 295 | | | | 300 | | | | | 305 | | | | |
| TTA | GTA | TCT | ACA | CAA | ACG | CAA | TAT | TTT | TTA | GCG | GCA | ATG | CTA | TCG | GAC | 5091 |
| Leu | Val | Ser | Thr | Gln | Thr | Gln | Tyr | Phe | Leu | Ala | Ala | Met | Leu | Ser | Asp | |
| | | 310 | | | | | 315 | | | | | 320 | | | | |
| GAA | AAA | TTC | GTC | GAT | AAT | TTT | CTA | AGA | GAA | AGC | GCG | ATG | AGG | TTA | GGT | 5139 |
| Glu | Lys | Phe | Val | Asp | Asn | Phe | Leu | Arg | Glu | Ser | Ala | Met | Arg | Leu | Gly | |
| 325 | | | | | 330 | | | | | 335 | | | | | 340 | |
| AAA | AGG | CAC | AAA | CAT | TTT | ACT | AAT | GGA | CTT | GAA | GTA | GTG | GGA | ATT | AAA | 5187 |
| Lys | Arg | His | Lys | His | Phe | Thr | Asn | Gly | Leu | Glu | Val | Val | Gly | Ile | Lys | |
| | | | | 345 | | | | | 350 | | | | | 355 | | |
| TGC | TTG | AAA | AAT | AAT | GCG | GGG | CTT | TTT | TGT | TGG | ATG | GAT | TTG | CGT | CCA | 5235 |
| Cys | Leu | Lys | Asn | Asn | Ala | Gly | Leu | Phe | Cys | Trp | Met | Asp | Leu | Arg | Pro | |
| | | | 360 | | | | | 365 | | | | | 370 | | | |
| CTT | TTA | AGG | GAA | TCG | ACT | TTC | GAT | AGC | GAA | ATG | TCG | TTA | TGG | AGA | GTT | 5283 |
| Leu | Leu | Arg | Glu | Ser | Thr | Phe | Asp | Ser | Glu | Met | Ser | Leu | Trp | Arg | Val | |
| | | 375 | | | | | 380 | | | | | 385 | | | | |
| ATT | ATA | AAC | GAT | GTT | AAG | CTT | AAC | GTC | TCG | CCT | GGA | TCT | TCG | TTT | GAA | 5331 |
| Ile | Ile | Asn | Asp | Val | Lys | Leu | Asn | Val | Ser | Pro | Gly | Ser | Ser | Phe | Glu | |
| | 390 | | | | | 395 | | | | | 400 | | | | | |
| TGT | CAA | GAG | CCA | GGG | TGG | TTC | CGA | GTT | TGT | TTT | GCA | AAT | ATG | GAT | GAT | 5379 |
| Cys | Gln | Glu | Pro | Gly | Trp | Phe | Arg | Val | Cys | Phe | Ala | Asn | Met | Asp | Asp | |
| 405 | | | | 410 | | | | | 415 | | | | | 420 | | |
| GGA | ACG | GTT | GAT | ATT | GCG | CTC | GCG | AGG | ATT | CGG | AGG | TTC | GTA | GGT | GTT | 5427 |
| Gly | Thr | Val | Asp | Ile | Ala | Leu | Ala | Arg | Ile | Arg | Arg | Phe | Val | Gly | Val | |
| | | | | 425 | | | | 430 | | | | | 435 | | | |
| GAG | AAA | AGT | GGA | GAT | AAA | TCG | AGT | TCG | ATG | GAA | AAG | AAG | CAA | CAA | TGG | 5475 |
| Glu | Lys | Ser | Gly | Asp | Lys | Ser | Ser | Ser | Met | Glu | Lys | Lys | Gln | Gln | Trp | |
| | | | 440 | | | | | 445 | | | | | 450 | | | |
| AAG | AAG | AAT | AAT | TTG | AGA | CTT | AGT | TTT | TCG | AAA | AGA | ATG | TAT | GAT | GAA | 5523 |
| Lys | Lys | Asn | Asn | Leu | Arg | Leu | Ser | Phe | Ser | Lys | Arg | Met | Tyr | Asp | Glu | |
| | | 455 | | | | | 460 | | | | | 465 | | | | |
| AGT | GTT | TTG | TCA | CCA | CTT | TCG | TCA | CCT | ATT | CCT | CCC | TCA | CCA | TTA | GTT | 5571 |
| Ser | Val | Leu | Ser | Pro | Leu | Ser | Ser | Pro | Ile | Pro | Pro | Ser | Pro | Leu | Val | |
| | | 470 | | | | | 475 | | | | | 480 | | | | |
| CGT | TAAGACTTAA | TTAAAAGGGA | AGAATTTAAT | TTATGTTTTT | TTATATTTTG | 5624 |
| Arg | | | | | | |
| 485 | | | | | | |

| | | | | |
|---|---|---|---|---|
| AAAAAAATTT | GTAAGAATAA | GATTATAATA | GGAAAGAAA | ATAAGTATGT AGGATGAGGA | 5684 |
| GTATTTCAG | AAATAGTTGT | TAGCGTATGT | ATTGACAACT | GGTCTATGTA CTTAGACATC | 5744 |
| ATAATTTGTC | TTAGCTAATT | AATGAATGCA | AAAGTGAAGT | TATGTTATGA CTCTTAGAAT | 5804 |
| CTTTTGATTT | ATTGGACTTT | CTCGATTATA | TTGTTATTAT | TAAATTCAT ATATTTTATA | 5864 |
| TATTTAAAAA | GTGTCGTAAG | TCATAATAAT | TGACAAGATA | TATGAAAACT TTACGATCAA | 5924 |
| AGATAAATTT | GTTTAAATTT | TAAAATTTAA | AGTGTGTCAC | ATAAATTGAG ATGGAGAGAT | 5984 |
| TATGGTGTTT | GTGTATATTT | TAATGGAAAA | ATACAGTGCG | TGTTTGTGGG GGATTGACTC | 6044 |
| CAGATGATAG | AGTAGAAATG | GATCTCCTAA | TTTTTTTATT | TATGTTTTAC TTTATCGAGG | 6104 |
| GTCTATCAAA | AATAATTTAT | CTATTTTTA | AATAGAGATA | AAGTCTGACA TACTCTTTTT | 6164 |
| ACTTGTATTT | ATATGTCATG | ATTTTGATTA | GGAGTTTGGA | TTTTCTCTAC GTTCAAATAC | 6224 |
| AAATTAAACT | ATAATGAGTT | ATTTTCCCTA | AATTTGGAGA | AATTATCATT TGGAGATGAG | 6284 |
| TACACGATAA | TAATGTCCTC | TAATCAATTA | CATCAAACAC | AAAAACATTA TTAGAAATTC | 6344 |

```
ACAATCTACA TGTTTGTCTA ATTAATCACA TCTTCATAGT TGATAAGTAG TACTTATCAT    6404

ACTTTGTAGT TTATGATTTC GAATAACTTG ACATATGATT AATTTTGTAA TACTACATTA    6464

CTGTTTATCA AACTTGTTTT TCGAATTCAT TTCTAGTAGT GTGTGGCATG ACTTGGACAA    6524

GAGAAATACA AATATTTTGA ATTTATTCCT ACTATACATT TTATTTTATT TTAATCTATA    6584

TATAAAAGAA TATCGTACAT ATTTATTAAT ATAAATTTT GATATTACT TTTTATTATA      6644

GAATTTGATA TCCAGTCAAA CCGCCACATA AATTGAGCCA ATATGTAAAT AGAAAATGTT    6704

GACAAAAGAA ATGGATTTAT TGGAAGACAA ACTGACATAG GGTCCAACTG AAAAGAGTTA    6764

AATTGTCGGA CGACTTTATA ATATTTTAGT CAACCCCACC CAAAGCCTTT TAAACTTAGA    6824

TAAATCCAAA AGATAATAAT TTGATTGAT ATTTATAAT GTATCTTTTT ATCATATTGA      6884

CATGTAGAAA AATTATAATT TATAATATTT TTATATAGT TTTTAAATAT TTAAAATTTT    6944

TATTTAAAAT ATTAAATGAA TATATTTTAA CTTTAGTTAA TCAATGACTT TTAAAAAACG    7004

TAATATGACA ATTAAATGAA TAGAAAAAAT ATCGATTAAT AAGACTTTTG AGATGAAAAT    7064

ATTGTCTCAT GTGAACGATG CTAACGATGT CTCCAACATG GATTTTGCTT CCTTGGCTTT    7124

ATTTCATGAT TTAATATTTA TATTGAAATG ACTAAGGTAA GTAAAAAAAC AAATTTCATA    7184

TTAAAGTTTT GTTTGAGTTG AATTCAAGTT TTGATTATTT TTCTATTAGA AATCAGATCT    7244
```

( 2 ) INFORMATION FOR SEQ ID NO:27:

( i ) SEQUENCE CHARACTERISTICS:
        ( A ) LENGTH: 485 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Met Gly Phe Glu Ile Ala Lys Thr Asn Ser Ile Leu Ser Lys Leu Ala
 1               5                  10                  15

Thr Asn Glu Glu His Gly Glu Asn Ser Pro Tyr Phe Asp Gly Trp Lys
            20                  25                  30

Ala Tyr Asp Ser Asp Pro Phe His Pro Leu Lys Asn Pro Asn Gly Val
        35                  40                  45

Ile Gln Met Gly Leu Ala Glu Asn Gln Leu Cys Leu Asp Leu Ile Glu
    50                  55                  60

Asp Trp Ile Lys Arg Asn Pro Lys Gly Ser Ile Cys Ser Glu Gly Ile
65                  70                  75                  80

Lys Ser Phe Lys Ala Ile Ala Asn Phe Gln Asp Tyr His Gly Leu Pro
                85                  90                  95

Glu Phe Arg Lys Ala Ile Ala Lys Phe Met Glu Lys Thr Arg Gly Gly
            100                 105                 110

Arg Val Arg Phe Asp Pro Glu Val Val Met Ala Gly Gly Ala Thr
        115                 120                 125

Gly Ala Asn Glu Thr Ile Ile Phe Cys Leu Ala Asp Pro Gly Asp Ala
    130                 135                 140

Phe Leu Val Pro Ser Pro Tyr Tyr Pro Ala Phe Asn Arg Asp Leu Arg
145                 150                 155                 160

Trp Arg Thr Gly Val Gln Leu Ile Pro Ile His Cys Glu Ser Ser Asn
                165                 170                 175

Asn Phe Lys Ile Thr Ser Lys Ala Val Lys Glu Ala Tyr Glu Asn Ala
            180                 185                 190

Gln Lys Ser Asn Ile Lys Val Lys Gly Leu Ile Leu Thr Asn Pro Ser
```

|     |     |     |     | 195 |     |     |     |     | 200 |     |     |     |     | 205 |     |
|-----|-----|-----|-----|-----|-----|-----|-----|-----|-----|-----|-----|-----|-----|-----|-----|
| Asn | Pro | Leu | Gly | Thr | Thr | Leu | Asp | Lys | Asp | Thr | Leu | Lys | Ser | Val | Leu |
|     | 210 |     |     |     |     | 215 |     |     |     |     | 220 |     |     |     |     |
| Ser | Phe | Thr | Asn | Gln | His | Asn | Ile | His | Leu | Val | Cys | Asp | Glu | Ile | Tyr |
| 225 |     |     |     |     | 230 |     |     |     |     | 235 |     |     |     |     | 240 |
| Ala | Ala | Thr | Val | Phe | Asp | Thr | Pro | Gln | Phe | Val | Ser | Ile | Ala | Glu | Ile |
|     |     |     |     | 245 |     |     |     |     | 250 |     |     |     |     | 255 |     |
| Leu | Asp | Glu | Gln | Glu | Met | Thr | Tyr | Cys | Asn | Lys | Asp | Leu | Val | His | Ile |
|     |     |     | 260 |     |     |     |     | 265 |     |     |     |     | 270 |     |     |
| Val | Tyr | Ser | Leu | Ser | Lys | Asp | Met | Gly | Leu | Pro | Gly | Phe | Arg | Val | Gly |
|     |     | 275 |     |     |     |     | 280 |     |     |     |     | 285 |     |     |     |
| Ile | Ile | Tyr | Ser | Phe | Asn | Asp | Val | Val | Asn | Cys | Ala | Arg | Lys | Met |
|     | 290 |     |     |     |     | 295 |     |     |     |     | 300 |     |     |     |     |
| Ser | Ser | Phe | Gly | Leu | Val | Ser | Thr | Gln | Thr | Gln | Tyr | Phe | Leu | Ala | Ala |
| 305 |     |     |     |     | 310 |     |     |     |     | 315 |     |     |     |     | 320 |
| Met | Leu | Ser | Asp | Glu | Lys | Phe | Val | Asp | Asn | Phe | Leu | Arg | Glu | Ser | Ala |
|     |     |     |     | 325 |     |     |     |     | 330 |     |     |     |     | 335 |     |
| Met | Arg | Leu | Gly | Lys | Arg | His | Lys | His | Phe | Thr | Asn | Gly | Leu | Glu | Val |
|     |     |     | 340 |     |     |     |     | 345 |     |     |     |     | 350 |     |     |
| Val | Gly | Ile | Lys | Cys | Leu | Lys | Asn | Asn | Ala | Gly | Leu | Phe | Cys | Trp | Met |
|     |     | 355 |     |     |     |     | 360 |     |     |     |     | 365 |     |     |     |
| Asp | Leu | Arg | Pro | Leu | Leu | Arg | Glu | Ser | Thr | Phe | Asp | Ser | Glu | Met | Ser |
|     | 370 |     |     |     |     | 375 |     |     |     |     | 380 |     |     |     |     |
| Leu | Trp | Arg | Val | Ile | Ile | Asn | Asp | Val | Lys | Leu | Asn | Val | Ser | Pro | Gly |
| 385 |     |     |     |     | 390 |     |     |     |     | 395 |     |     |     |     | 400 |
| Ser | Ser | Phe | Glu | Cys | Gln | Glu | Pro | Gly | Trp | Phe | Arg | Val | Cys | Phe | Ala |
|     |     |     |     | 405 |     |     |     |     | 410 |     |     |     |     | 415 |     |
| Asn | Met | Asp | Asp | Gly | Thr | Val | Asp | Ile | Ala | Leu | Ala | Arg | Ile | Arg | Arg |
|     |     |     | 420 |     |     |     |     | 425 |     |     |     |     | 430 |     |     |
| Phe | Val | Gly | Val | Glu | Lys | Ser | Gly | Asp | Lys | Ser | Ser | Ser | Met | Glu | Lys |
|     |     | 435 |     |     |     |     | 440 |     |     |     |     | 445 |     |     |     |
| Lys | Gln | Gln | Trp | Lys | Lys | Asn | Asn | Leu | Arg | Leu | Ser | Phe | Ser | Lys | Arg |
|     | 450 |     |     |     |     | 455 |     |     |     |     | 460 |     |     |     |     |
| Met | Tyr | Asp | Glu | Ser | Val | Leu | Ser | Pro | Leu | Ser | Ser | Pro | Ile | Pro | Pro |
| 465 |     |     |     |     | 470 |     |     |     |     | 475 |     |     |     |     | 480 |
| Ser | Pro | Leu | Val | Arg |     |     |     |     |     |     |     |     |     |     |     |
|     |     |     |     | 485 |     |     |     |     |     |     |     |     |     |     |     |

( 2 ) INFORMATION FOR SEQ ID NO:28:

( i ) SEQUENCE CHARACTERISTICS:
        ( A ) LENGTH: 493 amino acids
        ( B ) TYPE: amino acid
        ( C ) STRANDEDNESS: single
        ( D ) TOPOLOGY: linear ( x i ) SEQUENCE DESCRIPTION: SEQ ID NO:28:

| Met | Gly | Phe | His | Gln | Ile | Asp | Glu | Arg | Asn | Gln | Ala | Leu | Leu | Ser | Lys |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ile | Ala | Leu | Asp | Asp | Gly | His | Gly | Glu | Asn | Ser | Pro | Tyr | Phe | Asp | Gly |
|     |     |     | 20  |     |     |     |     | 25  |     |     |     |     | 30  |     |     |
| Trp | Lys | Ala | Tyr | Asp | Asn | Asp | Pro | Phe | His | Pro | Glu | Asn | Asn | Pro | Leu |
|     |     | 35  |     |     |     |     | 40  |     |     |     |     | 45  |     |     |     |
| Gly | Val | Ile | Gln | Met | Gly | Leu | Ala | Glu | Asn | Gln | Leu | Ser | Phe | Asp | Met |
|     |     | 50  |     |     |     |     | 55  |     |     |     |     | 60  |     |     |     |
| Ile | Val | Asp | Trp | Ile | Arg | Lys | His | Pro | Glu | Ala | Ser | Ile | Cys | Thr | Pro |

-continued

| | 65 | | | | 70 | | | | 75 | | | | 80 | | |
|---|---|---|---|---|---|---|---|---|---|---|---|---|---|---|---|
| Glu | Gly | Leu | Glu | Arg | Phe | Lys | Ser | Ile | Ala | Asn | Phe | Gln | Asp | Tyr | His |
| | | | | 85 | | | | 90 | | | | 95 | | | |
| Gly | Leu | Pro | Glu | Phe | Arg | Asn | Ala | Ile | Ala | Asn | Phe | Met | Gly | Lys | Val |
| | | | 100 | | | | 105 | | | | | 110 | | | |
| Arg | Gly | Gly | Arg | Val | Lys | Phe | Asp | Pro | Ser | Arg | Ile | Val | Met | Gly | Gly |
| | | 115 | | | | 120 | | | | | 125 | | | | |
| Gly | Ala | Thr | Gly | Ala | Ser | Glu | Thr | Val | Ile | Phe | Cys | Leu | Ala | Asp | Pro |
| 130 | | | | | 135 | | | | | 140 | | | | | |
| Gly | Asp | Ala | Phe | Leu | Val | Pro | Ser | Pro | Tyr | Tyr | Ala | Gly | Phe | Asp | Arg |
| 145 | | | | 150 | | | | 155 | | | | | | | 160 |
| Asp | Leu | Lys | Trp | Arg | Thr | Arg | Ala | Gln | Ile | Ile | Arg | Val | His | Cys | Asn |
| | | | | 165 | | | | 170 | | | | | | 175 | |
| Arg | Ser | Asn | Asn | Phe | Gln | Val | Thr | Lys | Ala | Ala | Leu | Glu | Ile | Ala | Tyr |
| | | | 180 | | | | | 185 | | | | | 190 | | |
| Lys | Lys | Ala | Gln | Glu | Ala | Asn | Met | Lys | Val | Lys | Gly | Val | Ile | Ile | Thr |
| | | 195 | | | | | 200 | | | | | 205 | | | |
| Asn | Pro | Ser | Asn | Pro | Leu | Gly | Thr | Thr | Tyr | Asp | Arg | Asp | Thr | Leu | Lys |
| | 210 | | | | | 215 | | | | | 220 | | | | |
| Thr | Leu | Val | Thr | Phe | Val | Asn | Gln | His | Asp | Ile | His | Leu | Ile | Cys | Asp |
| 225 | | | | | 230 | | | | | 235 | | | | | 240 |
| Glu | Ile | Tyr | Ser | Ala | Thr | Val | Phe | Lys | Ala | Pro | Thr | Phe | Thr | Ser | Ile |
| | | | | 245 | | | | | 250 | | | | | 255 | |
| Ala | Glu | Ile | Val | Glu | Gln | Met | Glu | His | Cys | Lys | Lys | Glu | Leu | Ile | His |
| | | | 260 | | | | | 265 | | | | | 270 | | |
| Ile | Leu | Tyr | Ser | Leu | Ser | Lys | Asp | Met | Gly | Leu | Pro | Gly | Phe | Arg | Val |
| | | 275 | | | | | 280 | | | | | 285 | | | |
| Gly | Ile | Ile | Tyr | Ser | Tyr | Asn | Asp | Val | Val | Val | Arg | Arg | Ala | Arg | Gln |
| | 290 | | | | | 295 | | | | | 300 | | | | |
| Met | Ser | Ser | Phe | Gly | Leu | Val | Ser | Ser | Gln | Thr | Gln | His | Leu | Leu | Ala |
| 305 | | | | | 310 | | | | | 315 | | | | | 320 |
| Ala | Met | Leu | Ser | Asp | Glu | Asp | Phe | Val | Asp | Lys | Phe | Leu | Ala | Glu | Asn |
| | | | | 325 | | | | | 330 | | | | | 335 | |
| Ser | Lys | Arg | Val | Gly | Glu | Arg | His | Ala | Arg | Phe | Thr | Lys | Glu | Leu | Asp |
| | | | 340 | | | | | 345 | | | | | 350 | | |
| Lys | Met | Gly | Ile | Thr | Cys | Leu | Asn | Ser | Asn | Ala | Gly | Val | Phe | Val | Trp |
| | | 355 | | | | | 360 | | | | | 365 | | | |
| Met | Asp | Leu | Arg | Arg | Leu | Leu | Lys | Asp | Gln | Thr | Phe | Lys | Ala | Glu | Met |
| | 370 | | | | | 375 | | | | | 380 | | | | |
| Glu | Leu | Trp | Arg | Val | Ile | Ile | Asn | Glu | Val | Lys | Leu | Asn | Val | Ser | Pro |
| 385 | | | | | 390 | | | | | 395 | | | | | 400 |
| Gly | Ser | Ser | Phe | His | Val | Thr | Glu | Pro | Gly | Trp | Phe | Arg | Val | Cys | Phe |
| | | | | 405 | | | | | 410 | | | | | 415 | |
| Ala | Asn | Met | Asp | Asp | Asn | Thr | Val | Asp | Val | Ala | Leu | Asn | Arg | Ile | His |
| | | | 420 | | | | | 425 | | | | | 430 | | |
| Ser | Phe | Val | Glu | Asn | Ile | Asp | Lys | Lys | Glu | Asp | Asn | Thr | Val | Ala | Met |
| | | 435 | | | | | 440 | | | | | 445 | | | |
| Pro | Ser | Lys | Thr | Arg | His | Arg | Asp | Asn | Lys | Leu | Arg | Leu | Ser | Phe | Ser |
| | 450 | | | | | 455 | | | | | 460 | | | | |
| Phe | Ser | Gly | Arg | Arg | Tyr | Asp | Glu | Gly | Asn | Val | Leu | Asn | Ser | Pro | His |
| 465 | | | | | 470 | | | | | 475 | | | | | 480 |
| Thr | Met | Ser | Pro | His | Ser | Pro | Leu | Val | Ile | Ala | Lys | Asn | | | |
| | | | 485 | | | | | 490 | | | | | | | |

( 2 ) INFORMATION FOR SEQ ID NO:29:

( i ) SEQUENCE CHARACTERISTICS:
        ( A ) LENGTH: 494 amino acids
        ( B ) TYPE: amino acid
        ( C ) STRANDEDNESS: single
        ( D ) TOPOLOGY: linear ( x i ) SEQUENCE DESCRIPTION: SEQ ID NO:29:

```
Met Gly Phe His Gln Ile Asp Glu Arg Asn Gln Ala Leu Leu Ser Lys
 1               5                  10                  15
Ile Ala Ile Asp Asp Gly His Gly Glu Asn Ser Ala Tyr Phe Asp Gly
                20                  25                  30
Trp Lys Ala Tyr Asp Asn Asn Pro Phe His Pro Glu Asn Asn Pro Leu
            35                  40                  45
Gly Val Ile Gln Met Gly Leu Ala Glu Asn Gln Leu Ser Phe Gly Met
        50                  55                  60
Ile Val Asp Trp Ile Arg Lys His Pro Glu Ala Ser Ile Cys Thr Pro
65                  70                  75                  80
Glu Gly Leu Glu Lys Phe Lys Ser Ile Ala Asn Phe Gln Asp Tyr His
                85                  90                  95
Gly Leu Gln Glu Phe Arg Lys Ala Met Ala Ser Phe Met Gly Lys Val
                100                 105                 110
Arg Gly Gly Arg Val Lys Phe Asp Pro Ser Arg Ile Val Met Gly Gly
            115                 120                 125
Gly Ala Thr Gly Ala Ser Glu Thr Val Ile Phe Cys Leu Ala Asp Pro
        130                 135                 140
Gly Asp Ala Phe Leu Val Pro Ser Pro Tyr Tyr Ala Ala Phe Asp Arg
145                 150                 155                 160
Asp Leu Lys Trp Arg Thr Arg Ala Gln Ile Ile Pro Val His Cys Asn
                165                 170                 175
Ser Ser Asn Asn Phe Gln Val Thr Glu Ala Ala Leu Glu Ile Ala Tyr
                180                 185                 190
Lys Lys Ala Gln Glu Ala Asn Met Lys Val Lys Gly Val Ile Ile Thr
            195                 200                 205
Asn Pro Ser Asn Pro Leu Gly Thr Thr Tyr Asp Arg Asp Thr Leu Lys
        210                 215                 220
Thr Leu Val Thr Phe Val Asn Gln His Asp Ile His Leu Ile Cys Asp
225                 230                 235                 240
Glu Ile Tyr Ser Ala Thr Val Phe Lys Ala Pro Thr Phe Thr Ser Ile
                245                 250                 255
Ala Glu Ile Val Glu Gln Met Glu His Cys Lys Lys Glu Leu Ile His
            260                 265                 270
Ile Leu Tyr Ser Leu Ser Lys Asp Met Gly Leu Pro Gly Phe Arg Val
        275                 280                 285
Gly Ile Ile Tyr Ser Tyr Asn Asp Val Val Val Arg Ala Arg Gln
        290                 295                 300
Met Ser Ser Phe Gly Leu Val Ser Ser Gln Thr Gln His Leu Leu Ala
305                 310                 315                 320
Ala Met Leu Ser Asp Glu Asp Phe Val Asp Lys Phe Leu Ala Glu Asn
                325                 330                 335
Ser Lys Arg Leu Gly Glu Arg His Ala Arg Phe Thr Lys Glu Leu Asp
            340                 345                 350
Lys Met Gly Ile Thr Cys Leu Asn Ser Asn Ala Gly Val Phe Val Trp
        355                 360                 365
```

```
Met Asp Leu Arg Arg Leu Leu Lys Asp Gln Thr Phe Lys Ala Glu Met
    370             375                 380

Glu Leu Trp Arg Val Ile Ile Asn Glu Val Lys Leu Asn Val Ser Pro
385             390                 395                     400

Gly Ser Ser Phe His Val Thr Glu Pro Gly Trp Phe Arg Val Cys Phe
                405             410                     415

Ala Asn Met Asp Asp Asn Thr Val Asp Val Ala Leu Asn Arg Ile His
            420             425                     430

Ser Phe Val Glu Asn Ile Asp Lys Lys Glu Asp Asn Thr Val Ala Met
        435             440                 445

Pro Ser Lys Thr Arg His Arg Asp Asn Lys Leu Arg Leu Ser Phe Ser
    450             455                 460

Phe Ser Gly Arg Arg Tyr Asp Lys Gly Asn Val Leu Asn Ser Pro His
465             470                 475                     480

Thr Met Ser Pro His Ser Pro Leu Val Arg Ala Arg Thr Tyr
            485             490
```

( 2 ) INFORMATION FOR SEQ ID NO:30:

( i ) SEQUENCE CHARACTERISTICS:
( A ) LENGTH: 485 amino acids
( B ) TYPE: amino acid
( C ) STRANDEDNESS: single
( D ) TOPOLOGY: linear ( x i ) SEQUENCE DESCRIPTION: SEQ ID NO:30:

```
Met Val Ser Ile Ser Lys Asn Asn Gln Lys Gln Gln Leu Leu Ser Lys
1               5                   10                  15

Ile Ala Thr Asn Asp Gly His Gly Glu Asn Ser Pro Tyr Phe Asp Gly
            20                  25                  30

Trp Lys Ala Tyr Ala Asn Asn Pro Phe His Leu Thr Asp Asn Pro Thr
        35                  40                  45

Gly Val Ile Gln Met Gly Leu Ala Glu Asn Gln Leu Cys Phe Asp Leu
    50                  55                  60

Ile Gln Glu Trp Val Val Asn Asn Pro Lys Ala Ser Ile Cys Thr Val
65              70                  75                      80

Glu Gly Ala Glu Asn Phe Gln Asp Ile Ala Ile Phe Gln Asp Tyr His
                85                  90                  95

Gly Leu Pro Glu Phe Arg Gln Ala Val Ala Arg Phe Met Glu Lys Val
            100                 105                 110

Arg Gly Asp Arg Val Thr Phe Asp Pro Asn Arg Ile Val Met Ser Gly
        115                 120                 125

Gly Ala Thr Gly Ala His Glu Met Leu Ala Phe Cys Leu Ala Asp Pro
    130                 135                 140

Gly Asp Ala Phe Leu Val Pro Thr Pro Tyr Tyr Pro Gly Phe Asp Arg
145                 150                 155                 160

Asp Leu Arg Trp Arg Thr Gly Val Gln Leu Phe Pro Val Val Cys Glu
                165                 170                 175

Ser Cys Asn Asp Phe Lys Val Thr Thr Lys Ala Leu Glu Glu Ala Tyr
            180                 185                 190

Glu Lys Ala Gln Gln Ser Asn Ile Lys Ile Lys Gly Leu Leu Ile Asn
        195                 200                 205

Asn Pro Ser Asn Pro Leu Gly Thr Leu Leu Asp Lys Asp Thr Leu Arg
    210                 215                 220

Asp Ile Val Thr Phe Ile Asn Ser Lys Asn Ile His Leu Val Cys Asp
225                 230                 235                 240
```

| Glu | Ile | Tyr | Ala | Ala<br>245 | Thr | Val | Phe | Asp | Gln<br>250 | Pro | Arg | Phe | Ile | Ser<br>255 | Val |
|---|---|---|---|---|---|---|---|---|---|---|---|---|---|---|---|
| Ser | Glu | Ile | Val<br>260 | Glu | Asp | Met | Ile | Glu<br>265 | Cys | Asn | Lys | Asp | Leu<br>270 | Ile | His |
| Ile | Val | Tyr<br>275 | Ser | Leu | Ser | Lys | Asp<br>280 | Leu | Gly | Phe | Pro | Gly<br>285 | Phe | Arg | Val |
| Gly | Ile<br>290 | Val | Tyr | Ser | Tyr | Asn<br>295 | Asp | Thr | Val | Val | Asn<br>300 | Ile | Ala | Arg | Lys |
| Met<br>305 | Ser | Ser | Phe | Gly | Leu<br>310 | Val | Ser | Thr | Gln | Thr<br>315 | Gln | His | Leu | Leu | Ala<br>320 |
| Ser | Met | Leu | Ser | Asp<br>325 | Glu | Val | Phe | Ile | Asp<br>330 | Lys | Phe | Ile | Ala | Glu<br>335 | Ser |
| Ser | Glu | Arg | Leu<br>340 | Gly | Glu | Arg | Gln | Gly<br>345 | Met | Phe | Thr | Lys | Gly<br>350 | Leu | Ala |
| Glu | Val | Gly<br>355 | Ile | Ser | Thr | Leu | Lys<br>360 | Ser | Asn | Ala | Gly | Leu<br>365 | Phe | Phe | Trp |
| Met | Asp<br>370 | Leu | Arg | Arg | Leu | Leu<br>375 | Lys | Glu | Ala | Thr | Phe<br>380 | Asp | Ser | Glu | Leu |
| Glu<br>385 | Leu | Trp | Arg | Ile | Ile<br>390 | Ile | Asn | Glu | Val | Lys<br>395 | Leu | Asn | Val | Ser | Pro<br>400 |
| Gly | Cys | Ser | Phe | His<br>405 | Cys | Ser | Glu | Pro | Gly<br>410 | Trp | Phe | Arg | Val | Cys<br>415 | Phe |
| Ala | Asn | Met | Asp<br>420 | Asp | Glu | Thr | Met | Arg<br>425 | Ile | Ala | Leu | Lys | Arg<br>430 | Ile | Ser |
| Tyr | Phe | Val<br>435 | Leu | Gln | Pro | Lys | Gly<br>440 | Leu | Asn | Asn | Ile | Ala<br>445 | Ala | Ile | Lys |
| Lys | Gln<br>450 | Cys | Ser | Arg | Arg | Lys<br>455 | Leu | Gln | Ile | Ser | Leu<br>460 | Ser | Phe | Arg | Arg |
| Leu<br>465 | Asp | His | Glu | Phe | Met<br>470 | Asn | Ser | Pro | Ala | His<br>475 | Ser | Pro | Met | Asn | Ser<br>480 |
| Pro | Leu | Val | Arg | Thr<br>485 | | | | | | | | | | | |

( 2 ) INFORMATION FOR SEQ ID NO:31:

( i ) SEQUENCE CHARACTERISTICS:
        ( A ) LENGTH: 483 amino acids
        ( B ) TYPE: amino acid
        ( C ) STRANDEDNESS: single
        ( D ) TOPOLOGY: linear ( x i ) SEQUENCE DESCRIPTION: SEQ ID NO:31:

| Met<br>1 | Val | Ser | Ile | Ser<br>5 | Lys | Asn | Asn | Gln | Lys<br>10 | Gln | Gln | Leu | Leu | Ser<br>15 | Lys |
|---|---|---|---|---|---|---|---|---|---|---|---|---|---|---|---|
| Ile | Ala | Thr | Asn<br>20 | Asp | Gly | His | Gly | Glu<br>25 | Asn | Ser | Pro | Tyr | Phe<br>30 | Asp | Gly |
| Trp | Lys | Ala<br>35 | Tyr | Ala | Asn | Asn | Pro<br>40 | Phe | His | Leu | Thr | Asp<br>45 | Asn | Pro | Thr |
| Gly | Val<br>50 | Ile | Gln | Met | Gly | Leu<br>55 | Ala | Glu | Asn | Gln | Leu<br>60 | Cys | Phe | Asp | Leu |
| Ile<br>65 | Gln | Glu | Trp | Met | Val<br>70 | Asn | Asn | Pro | Lys | Ala<br>75 | Ser | Ile | Cys | Thr | Val<br>80 |
| Glu | Gly | Ala | Glu | Asn<br>85 | Phe | Gln | Asp | Ile | Ala<br>90 | Ile | Phe | Gln | Asp | Tyr<br>95 | His |
| Gly | Leu | Pro | Glu<br>100 | Phe | Arg | Gln | Ala | Val<br>105 | Ala | Arg | Phe | Met | Glu<br>110 | Lys | Val |

Arg Gly Asp Arg Val Thr Phe Asp Pro Asn Arg Ile Val Met Ser Gly
        115                 120                 125

Gly Ala Thr Gly Ala His Glu Met Leu Ala Phe Cys Leu Ala Asp Pro
    130                 135                 140

Gly Asp Ala Phe Leu Val Pro Thr Pro Tyr Tyr Pro Gly Phe Asp Arg
145                 150                 155                 160

Asp Leu Arg Trp Arg Thr Gly Val Gln Leu Phe Pro Val Val Cys Glu
                165                 170                 175

Ser Cys Asn Asp Phe Lys Val Thr Thr Lys Ala Leu Glu Glu Ala Tyr
            180                 185                 190

Glu Lys Ala Gln Gln Ser Asn Ile Lys Ile Lys Gly Leu Leu Ile Asn
        195                 200                 205

Asn Pro Ser Asn Pro Leu Gly Thr Leu Leu Asp Lys Asp Thr Leu Arg
    210                 215                 220

Asp Ile Val Thr Phe Ile Asn Ser Lys Asn Ile His Leu Val Cys Asp
225                 230                 235                 240

Glu Ile Tyr Ala Ala Thr Val Phe Asp Gln Pro Arg Phe Ile Ser Val
                245                 250                 255

Ser Glu Met Val Glu Glu Met Ile Glu Cys Asn Thr Asp Leu Ile His
            260                 265                 270

Ile Val Tyr Ser Leu Ser Lys Asp Leu Gly Phe Pro Gly Phe Arg Val
        275                 280                 285

Gly Ile Val Tyr Ser Tyr Asn Asp Thr Val Val Asn Ile Ser Arg Lys
    290                 295                 300

Met Ser Ser Phe Gly Leu Val Ser Thr Gln Thr Gln His Met Leu Ala
305                 310                 315                 320

Ser Met Leu Ser Asp Glu Ile Phe Val Glu Lys Phe Ile Ala Glu Ser
                325                 330                 335

Ser Glu Arg Leu Gly Lys Arg Gln Gly Met Phe Thr Lys Gly Leu Ala
            340                 345                 350

Gln Val Gly Ile Ser Thr Leu Lys Ser Asn Ala Gly Leu Phe Phe Trp
        355                 360                 365

Met Asp Leu Arg Arg Leu Leu Lys Glu Ala Thr Phe Asp Gly Glu Leu
370                 375                 380

Glu Leu Trp Arg Ile Ile Ile Asn Glu Val Lys Leu Asn Val Ser Pro
385                 390                 395                 400

Gly Cys Ser Phe His Cys Ser Glu Pro Gly Trp Phe Arg Val Cys Phe
                405                 410                 415

Ala Asn Met Asp Asp Glu Thr Met Arg Ile Ala Leu Arg Arg Ile Arg
            420                 425                 430

Asn Phe Val Leu Gln Thr Lys Gly Leu Asn Asn Ile Ala Ala Ile Lys
        435                 440                 445

Lys Gln Cys Ser Arg Ser Lys Leu Gln Ile Ser Leu Ser Phe Arg Arg
    450                 455                 460

Leu Asp Asp Phe Asn Ser Pro Ala His Ser Pro Met Asn Ser Pro Leu
465                 470                 475                 480

Val Arg Thr ( 2 ) INFORMATION FOR SEQ ID NO:32:

( i ) SEQUENCE CHARACTERISTICS:
    ( A ) LENGTH: 485 amino acids
    ( B ) TYPE: amino acid
    ( C ) STRANDEDNESS: single
    ( D ) TOPOLOGY: linear ( x i ) SEQUENCE DESCRIPTION: SEQ ID NO:32:

| | | | | | | | | | | | | | | |
|---|---|---|---|---|---|---|---|---|---|---|---|---|---|---|
| Met 1 | Gly | Phe | Glu | Ile 5 | Ala | Lys | Thr | Asn | Ser 10 | Ile | Leu | Ser | Lys | Leu Ala 15 |
| Thr | Asn | Glu 20 | Glu | His | Gly | Glu | Asn | Ser 25 | Pro | Tyr | Phe | Asp | Gly 30 | Trp Lys |
| Ala | Tyr | Asp 35 | Ser | Asp | Pro | Phe | His 40 | Pro | Leu | Lys | Asn | Pro 45 | Asn | Gly Val |
| Ile | Gln 50 | Met | Gly | Leu | Ala | Glu 55 | Asn | Gln | Leu | Cys | Leu 60 | Asp | Leu | Ile Glu |
| Asp 65 | Trp | Ile | Lys | Arg | Asn 70 | Pro | Lys | Gly | Ser | Ile 75 | Cys | Ser | Glu | Gly Ile 80 |
| Lys | Ser | Phe | Lys | Ala 85 | Ile | Ala | Asn | Phe | Gln 90 | Asp | Tyr | His | Gly | Leu Pro 95 |
| Glu | Phe | Arg | Lys 100 | Ala | Ile | Ala | Lys | Phe 105 | Met | Glu | Lys | Thr | Arg 110 | Gly Gly |
| Arg | Val | Arg 115 | Phe | Asp | Pro | Glu | Arg 120 | Val | Val | Met | Ala | Gly 125 | Gly | Ala Thr |
| Gly | Ala 130 | Asn | Glu | Thr | Ile | Ile 135 | Phe | Cys | Leu | Ala | Asp 140 | Pro | Gly | Asp Ala |
| Phe 145 | Leu | Val | Pro | Ser | Pro 150 | Tyr | Tyr | Pro | Ala | Phe 155 | Asn | Arg | Asp | Leu Arg 160 |
| Trp | Arg | Thr | Gly | Val 165 | Gln | Leu | Ile | Pro | Ile 170 | His | Cys | Glu | Ser | Ser Asn 175 |
| Asn | Phe | Lys | Ile 180 | Thr | Ser | Lys | Ala | Val 185 | Lys | Glu | Ala | Tyr | Glu 190 | Asn Ala |
| Gln | Lys | Ser 195 | Asn | Ile | Lys | Val | Lys 200 | Gly | Leu | Ile | Leu | Thr 205 | Asn | Pro Ser |
| Asn | Pro 210 | Leu | Gly | Thr | Thr | Leu 215 | Asp | Lys | Asp | Thr | Leu 220 | Lys | Ser | Val Leu |
| Ser 225 | Phe | Thr | Asn | Gln | His 230 | Asn | Ile | His | Leu | Val 235 | Cys | Asp | Glu | Ile Tyr 240 |
| Ala | Ala | Thr | Val | Phe 245 | Asp | Thr | Pro | Gln | Phe 250 | Val | Ser | Ile | Ala | Glu Ile 255 |
| Leu | Asp | Glu | Gln 260 | Glu | Met | Thr | Tyr | Cys 265 | Asn | Lys | Asp | Leu | Val 270 | His Ile |
| Val | Tyr | Ser 275 | Leu | Ser | Lys | Asp | Met 280 | Gly | Leu | Pro | Gly | Phe 285 | Arg | Val Gly |
| Ile | Ile 290 | Tyr | Ser | Phe | Asn | Asp 295 | Val | Val | Asn | Cys 300 | Ala | Arg | Lys | Met |
| Ser 305 | Ser | Phe | Gly | Leu | Val 310 | Ser | Thr | Gln | Thr | Gln 315 | Tyr | Phe | Leu | Ala Ala 320 |
| Met | Leu | Ser | Asp | Glu 325 | Lys | Phe | Val | Asp | Asn 330 | Phe | Leu | Arg | Glu | Ser Ala 335 |
| Met | Arg | Leu | Gly 340 | Lys | Arg | His | Lys | His 345 | Phe | Thr | Asn | Gly | Leu 350 | Glu Val |
| Val | Gly | Ile 355 | Lys | Cys | Leu | Lys | Asn 360 | Asn | Ala | Gly | Leu | Phe 365 | Cys | Trp Met |
| Asp | Leu 370 | Arg | Pro | Leu | Leu | Arg 375 | Glu | Ser | Thr | Phe | Asp 380 | Ser | Glu | Met Ser |
| Leu 385 | Trp | Arg | Val | Ile | Ile 390 | Asn | Asp | Val | Lys | Leu 395 | Asn | Val | Ser | Pro Gly 400 |
| Ser | Ser | Phe | Glu | Cys 405 | Gln | Glu | Pro | Gly | Trp 410 | Phe | Arg | Val | Cys | Phe Ala 415 |

-continued

```
Asn  Met  Asp  Asp  Gly  Thr  Val  Asp  Ile  Ala  Leu  Ala  Arg  Ile  Arg  Arg
          420                      425                      430

Phe  Val  Gly  Val  Glu  Lys  Ser  Gly  Asp  Lys  Ser  Ser  Ser  Met  Glu  Lys
          435                      440                      445

Lys  Gln  Gln  Trp  Lys  Lys  Asn  Asn  Leu  Arg  Leu  Ser  Phe  Ser  Lys  Arg
     450                      455                      460

Met  Tyr  Asp  Glu  Ser  Val  Leu  Ser  Pro  Leu  Ser  Ser  Pro  Ile  Pro  Pro
465                      470                      475                      480

Ser  Pro  Leu  Val  Arg
                    485
```

(2) INFORMATION FOR SEQ ID NO:33:

(i) SEQUENCE CHARACTERISTICS:
    (A) LENGTH: 469 amino acids
    (B) TYPE: amino acid
    (C) STRANDEDNESS: single
    (D) TOPOLOGY: linear (xi) SEQUENCE DESCRIPTION: SEQ ID NO:33:

```
Met  Lys  Leu  Leu  Ser  Glu  Lys  Ala  Thr  Cys  Asn  Ser  His  Gly  Gln  Asp
1                   5                      10                       15

Ser  Ser  Tyr  Phe  Leu  Gly  Trp  Gln  Glu  Tyr  Glu  Lys  Asn  Pro  Tyr  Asp
               20                      25                       30

Glu  Ile  Gln  Asn  Pro  Lys  Gly  Ile  Ile  Gln  Met  Gly  Leu  Ala  Glu  Asn
          35                      40                       45

Gln  Leu  Ser  Phe  Asp  Leu  Leu  Glu  Ser  Trp  Leu  Ala  Gln  Asn  Pro  Asp
     50                      55                       60

Ala  Ala  Gly  Phe  Lys  Arg  Asn  Gly  Glu  Ser  Ile  Phe  Arg  Glu  Leu  Ala
65                       70                      75                            80

Leu  Phe  Gln  Asp  Tyr  His  Gly  Leu  Pro  Ala  Phe  Lys  Asn  Ala  Met  Thr
                    85                      90                       95

Lys  Phe  Met  Ser  Glu  Ile  Arg  Gly  Asn  Arg  Val  Ser  Phe  Asp  Ser  Asn
               100                     105                      110

Asn  Leu  Val  Leu  Thr  Ala  Gly  Ala  Thr  Ser  Ala  Asn  Glu  Thr  Leu  Met
          115                     120                      125

Phe  Cys  Leu  Ala  Asn  Gln  Gly  Asp  Ala  Phe  Leu  Leu  Pro  Thr  Pro  Tyr
     130                     135                      140

Tyr  Pro  Gly  Phe  Asp  Arg  Asp  Leu  Lys  Trp  Arg  Thr  Gly  Ala  Glu  Ile
145                      150                     155                           160

Val  Pro  Ile  His  Cys  Ser  Ser  Ser  Asn  Gly  Phe  Arg  Ile  Thr  Glu  Ser
                    165                     170                      175

Ala  Leu  Glu  Glu  Ala  Tyr  Leu  Asp  Ala  Lys  Lys  Arg  Asn  Leu  Lys  Val
               180                     185                      190

Lys  Gly  Val  Leu  Val  Thr  Asn  Pro  Ser  Asn  Pro  Leu  Gly  Thr  Thr  Leu
          195                     200                      205

Asn  Arg  Asn  Glu  Leu  Glu  Leu  Leu  Thr  Phe  Ile  Asp  Glu  Lys  Gly  Ile
     210                     215                      220

Ile  His  Leu  Ile  Ser  Asp  Glu  Ile  Tyr  Ser  Gly  Thr  Val  Phe  Asn  Ser
225                      230                     235                           240

Pro  Gly  Phe  Val  Ser  Val  Met  Glu  Val  Leu  Ile  Glu  Lys  Asn  Tyr  Met
                    245                     250                      255

Lys  Thr  Arg  Val  Trp  Glu  Arg  Val  His  Ile  Val  Tyr  Ser  Leu  Ser  Lys
               260                     265                      270

Asp  Leu  Gly  Leu  Pro  Gly  Phe  Arg  Ile  Gly  Ala  Ile  Tyr  Ser  Asn  Asp
          275                     280                      285
```

|     |     |     |     |     |     |     |     |     |     |     |     |     |     |     |
|---|---|---|---|---|---|---|---|---|---|---|---|---|---|---|
| Glu | Met 290 | Val | Val | Ser | Ala | Ala 295 | Thr | Lys | Met | Ser | Ser 300 | Phe | Gly | Leu | Val |
| Ser 305 | Ser | Gln | Thr | Gln | Tyr 310 | Leu | Leu | Ser | Cys | Met 315 | Leu | Ser | Asp | Lys | Lys 320 |
| Phe | Thr | Lys | Lys | Tyr 325 | Ile | Ser | Glu | Asn | Gln 330 | Lys | Arg | Leu | Lys | Lys 335 | Arg |
| His | Ala | Met | Leu 340 | Val | Lys | Gly | Leu | Lys 345 | Ser | Ala | Gly | Ile | Asn 350 | Cys | Leu |
| Glu | Ser | Asn 355 | Ala | Gly | Leu | Phe | Cys 360 | Trp | Val | Asp | Met | Arg 365 | His | Leu | Leu |
| Ser | Ser 370 | Asn | Asn | Phe | Asp | Ala 375 | Glu | Met | Asp | Leu | Trp 380 | Lys | Lys | Ile | Val |
| Tyr 385 | Asp | Val | Gly | Leu | Asn 390 | Ile | Ser | Pro | Gly | Ser 395 | Ser | Cys | His | Cys | Thr 400 |
| Glu | Pro | Gly | Trp | Phe 405 | Arg | Val | Cys | Phe | Ala 410 | Asn | Met | Ser | Glu | Asp 415 | Thr |
| Leu | Asp | Leu | Ala 420 | Met | Arg | Arg | Ile | Lys 425 | Asp | Phe | Val | Glu | Ser 430 | Thr | Ala |
| Pro | Asn | Ala 435 | Thr | Asn | His | Gln | Asn 440 | Gln | Gln | Gln | Ser | Asn 445 | Ala | Asn | Ser |
| Lys | Lys 450 | Lys | Ser | Phe | Ser | Lys 455 | Trp | Val | Phe | Arg | Leu 460 | Ser | Phe | Asn | Asp |
| Arg 465 | Gln | Arg | Glu | Arg | | | | | | | | | | | |

( 2 ) INFORMATION FOR SEQ ID NO:34:

( i ) SEQUENCE CHARACTERISTICS:
        ( A ) LENGTH: 476 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 281
        ( D ) OTHER INFORMATION: /note= "This position is S or A."

( i x ) FEATURE:
        ( A ) NAME/KEY: Modified-site
        ( B ) LOCATION: 284
        ( D ) OTHER INFORMATION: /note= "This position is M or r."

( i x ) FEATURE:
        ( A ) NAME/KEY: Modified-site
        ( B ) LOCATION: 286
        ( D ) OTHER INFORMATION: /note= "This position is F or L."

( i x ) FEATURE:
        ( A ) NAME/KEY: Modified-site
        ( B ) LOCATION: 288
        ( D ) OTHER INFORMATION: /note= "This position is G or N."

( x i ) SEQUENCE DESCRIPTION: SEQ ID NO:34:

|     |     |     |     |     |     |     |     |     |     |     |     |     |     |     |     |
|---|---|---|---|---|---|---|---|---|---|---|---|---|---|---|---|
| Met 1 | Asp | Leu | Glu | Thr 5 | Ser | Glu | Ile | Ser | Asn 10 | Tyr | Lys | Ser | Ser | Ala 15 | Val |
| Leu | Ser | Lys | Leu 20 | Ala | Ser | Asn | Glu | Gln 25 | His | Gly | Glu | Asn | Ser 30 | Pro | Tyr |
| Phe | Asp | Gly 35 | Trp | Lys | Ala | Tyr | Asp 40 | Asn | Asp | Pro | Phe | His 45 | Leu | Val | Asn |
| Asn | Leu 50 | Asn | Gly | Val | Ile | Gln 55 | Met | Gly | Leu | Ala | Glu 60 | Asn | Gln | Leu | Ser |
| Val | Asp | Leu | Ile | Glu | Glu | Trp | Ile | Lys | Arg | Asn | Pro | Lys | Ala | Ser | Ile |

```
              65                        70                        75                        80
    Cys  Thr  Asn  Asp  Gly  Ile  Glu  Ser  Phe  Arg  Arg  Ile  Ala  Asn  Phe  Gln
                        85                        90                        95

Asp  Tyr  His  Gly  Leu  Pro  Glu  Phe  Thr  Asn  Ala  Ile  Ala  Lys  Phe  Met
                        100                       105                       110

Glu  Lys  Thr  Arg  Gly  Gly  Lys  Val  Lys  Phe  Asp  Ala  Lys  Arg  Val  Val
                  115                       120                       125

Met  Ala  Gly  Gly  Ala  Thr  Gly  Ala  Asn  Glu  Thr  Leu  Ile  Leu  Cys  Leu
         130                       135                            140

Ala  Asp  Pro  Gly  Asp  Ala  Phe  Leu  Val  Pro  Thr  Pro  Tyr  Tyr  Pro  Gly
    145                      150                       155                       160

Phe  Asn  Arg  Asp  Leu  Arg  Trp  Arg  Ser  Gly  Val  Gln  Leu  Leu  Pro  Ile
                        165                       170                            175

Ser  Cys  Lys  Ser  Cys  Asn  Asn  Phe  Lys  Ile  Thr  Ile  Glu  Ala  Ile  Glu
                   180                       185                            190

Glu  Ala  Tyr  Glu  Lys  Gly  Gln  Gln  Ala  Asn  Val  Lys  Ile  Lys  Gly  Leu
                   195                       200                       205

Ile  Leu  Thr  Asn  Pro  Cys  Asn  Pro  Leu  Gly  Thr  Ile  Leu  Asp  Arg  Asp
         210                       215                       220

Thr  Leu  Lys  Lys  Ile  Ser  Thr  Phe  Thr  Asn  Glu  His  Asn  Ile  His  Leu
    225                       230                       235                       240

Val  Cys  Asp  Glu  Ile  Tyr  Ala  Ala  Thr  Val  Phe  Asn  Ser  Pro  Lys  Phe
                        245                       250                       255

Val  Ser  Ile  Ala  Glu  Ile  Ile  Asn  Glu  Asp  Asn  Cys  Ile  Asn  Lys  Asp
                        260                       265                       270

Leu  Val  His  Ile  Val  Ser  Ser  Leu  Xaa  Lys  Asp  Xaa  Gly  Xaa  Pro  Xaa
                   275                       280                       285

Phe  Arg  Val  Gly  Ile  Val  Tyr  Ser  Phe  Asn  Asp  Asp  Val  Val  Asn  Cys
         290                       295                       300

Ala  Arg  Lys  Met  Ser  Ser  Phe  Gly  Leu  Val  Ser  Thr  Gln  Thr  Gln  His
    305                       310                       315                       320

Leu  Leu  Ala  Phe  Met  Leu  Ser  Asp  Asp  Glu  Phe  Val  Glu  Glu  Phe  Leu
                        325                       330                       335

Ile  Glu  Ser  Ala  Lys  Arg  Leu  Arg  Glu  Arg  Tyr  Glu  Lys  Phe  Thr  Arg
                   340                       345                       350

Gly  Leu  Glu  Glu  Ile  Gly  Ile  Lys  Cys  Leu  Glu  Ser  Asn  Ala  Gly  Val
              355                       360                       365

Tyr  Cys  Trp  Met  Asp  Leu  Arg  Ser  Leu  Leu  Lys  Glu  Ala  Thr  Leu  Asp
         370                       375                       380

Ala  Glu  Met  Ser  Leu  Trp  Lys  Leu  Ile  Ile  Asn  Glu  Val  Lys  Leu  Asn
    385                       390                       395                       400

Val  Ser  Pro  Gly  Ser  Ser  Phe  Asn  Cys  Ser  Glu  Val  Gly  Trp  Phe  Arg
                        405                       410                       415

Val  Cys  Phe  Ala  Asn  Ile  Asp  Asp  Gln  Thr  Met  Glu  Ile  Ala  Leu  Ala
                   420                       425                       430

Arg  Ile  Arg  Met  Phe  Met  Asp  Ala  Tyr  Asn  Asn  Val  Asn  Lys  Asn  Gly
              435                       440                       445

Val  Met  Lys  Asn  Lys  His  Asn  Gly  Arg  Gly  Thr  Thr  Tyr  Asp  Leu  Thr
         450                       455                       460

Pro  Gln  Met  Gly  Ser  Thr  Met  Lys  Met  Leu  Leu  Ala
    465                       470                       475
```